US012746397B2

(12) United States Patent
Rogers et al.

(10) Patent No.: US 12,746,397 B2
(45) Date of Patent: Sep. 29, 2026

(54) BIORESORBABLE CARDIOVASCULAR INSTRUMENTS, AND OPERATION AND FABRICATION METHODS OF SAME

(71) Applicants: NORTHWESTERN UNIVERSITY, Evanston, IL (US); THE GEORGE WASHINGTON UNIVERSITY, Washington, DC (US)

(72) Inventors: John A. Rogers, Wilmette, IL (US); Yeonsik Choi, Evanston, IL (US); Igor Efimov, Washington, DC (US); Rose T. Yin, Washington, DC (US)

(73) Assignees: NORTHWESTERN UNIVERSITY, Evanston, IL (US); THE GEORGE WASHINGTON UNIVERSITY, Washington, DC (US)

( * ) Notice: Subject to any disclaimer, the term of this patent is extended or adjusted under 35 U.S.C. 154(b) by 245 days.

(21) Appl. No.: 18/569,649

(22) PCT Filed: Jun. 27, 2022

(86) PCT No.: PCT/US2022/035089
§ 371 (c)(1),
(2) Date: Dec. 13, 2023

(87) PCT Pub. No.: WO2022/272164
PCT Pub. Date: Dec. 29, 2022

(65) Prior Publication Data

US 2024/0269473 A1 Aug. 15, 2024

Related U.S. Application Data

(60) Provisional application No. 63/215,070, filed on Jun. 25, 2021.

(51) Int. Cl.
*A61N 1/375* (2006.01)
*A61L 31/10* (2006.01)
(Continued)

(52) U.S. Cl.
CPC .......... *A61N 1/37229* (2013.01); *A61L 31/10* (2013.01); *A61L 31/148* (2013.01);
(Continued)

(58) Field of Classification Search
CPC ............................ A61N 1/3756; A61N 1/3787
See application file for complete search history.

(56) References Cited

U.S. PATENT DOCUMENTS

| | | | | |
|---|---|---|---|---|
| 8,019,419 B1 * | 9/2011 | Panescu | A61N 1/05 | 607/33 |
| 2008/0175885 A1 * | 7/2008 | Asgari | A61L 31/128 | 424/426 |

(Continued)

OTHER PUBLICATIONS

Choi, Y.S., Yin, R.T., Pfenniger, A. et al. Fully implantable and bioresorbable cardiac pacemakers without leads or batteries. Nat Biotechnol 39, 1228-1238 (2021). https://doi.org/10.1038/s41587-021-00948-x (Year: 2021).*

(Continued)

*Primary Examiner* — William J Levicky
(74) *Attorney, Agent, or Firm* — troutman pepper locke; Tim Tingkang Xia, Esq.

(57) ABSTRACT

A device implantable on a target of interest of a subject for pacemaker, neuromodulator, and/or defibrillator therapy comprises a wireless power harvesting unit configured to deliver power via resonant inductive coupling to the target tissue for stimulation in a manner that eliminates need for batteries and allows for externalized control without transcutaneous leads. The device relies exclusively on materials that resorb when exposed to biofluids in a time-controlled manner via metabolic action and hydrolysis. The materials and design choices create a thin, flexible, and lightweight form that maintain excellent biocompatibility and stable function throughout a desired period of use. Over a subsequent timeframe following the completion of therapy, the
(Continued)

devices disappear completely through natural biological processes. These characteristics and a miniaturized geometry facilitate full implantation into the body to eliminate the need for percutaneous hardware, which thereby minimizes the risk of device-associated infections and dislodgement.

65 Claims, 28 Drawing Sheets

(51) Int. Cl.

| | |
|---|---|
| ***A61L 31/14*** | (2006.01) |
| ***A61N 1/02*** | (2006.01) |
| ***A61N 1/05*** | (2006.01) |
| ***A61N 1/362*** | (2006.01) |
| ***A61N 1/372*** | (2006.01) |
| ***A61N 1/378*** | (2006.01) |
| ***A61N 1/39*** | (2006.01) |
| *A61L 31/02* | (2006.01) |

(52) U.S. Cl.

CPC ............ *A61N 1/025* (2013.01); *A61N 1/059* (2013.01); *A61N 1/0595* (2013.01); *A61N 1/362* (2013.01); *A61N 1/37512* (2017.08); *A61N 1/3756* (2013.01); *A61N 1/3758* (2013.01); *A61N 1/3787* (2013.01); *A61N 1/39622* (2017.08); *A61L 31/022* (2013.01)

(56) References Cited

U.S. PATENT DOCUMENTS

| | | | | |
|---|---|---|---|---|
| 2012/0296399 | A1 | 11/2012 | Cauller et al. | |
| 2013/0140649 | A1* | 6/2013 | Rogers | H10F 30/00 438/48 |
| 2014/0200626 | A1* | 7/2014 | Campbell | A61N 1/37516 607/46 |
| 2014/0323968 | A1* | 10/2014 | Rogers | A61M 5/44 29/829 |
| 2019/0139713 | A1 | 5/2019 | Choi | |
| 2020/0188657 | A1* | 6/2020 | Ray | A61N 1/0504 |
| 2021/0346693 | A1* | 11/2021 | Deslauriers | A61N 1/3603 |

OTHER PUBLICATIONS

Waldo, A. L., Wells, J. L. J., Cooper, T. B. & MacLean, W. A. Temporary cardiac pacing: applications and techniques in the treatment of cardiac arrhythmias. Prog. Cardiovasc. Dis. 23, 451-474 (1981).

Zoll, P. M. et al. External noninvasive temporary cardiac pacing: Clinical trials. Circulation 71, 937-944 (1985).

Curtis, J. J. et al. A critical look at temporary ventricular pacing following cardiac surgery. Surgery 82, 888-893 (1977).

Wilhelm, M. J. et al. Cardiac pacemaker infection: Surgical management with and without extracorporeal circulation. Ann. Thorac. Surg. 64, 1707-1712 (1997).

Choo, M. H. et al. Permanent pacemaker infections: Characterization and management. Am. J. Cardiol. 48, 559-564 (1981).

Imparato, A. M. & Kim, G. E. Electrode Complications in Patients With Permanent Cardiac Pacemakers. Arch. Surg. 105, 705 (1972).

Bernstein, V., Rotem, C. E. & Peretz, D. I. Permanent pacemakers: 8-year follow-up study. Incidence and management of congestive cardiac failure and perforations. Ann. Intern. Med. 74, 361-369 (1971).

Hartstein, A. I., Jackson, J. & Gilbert, D. N. Prophylactic antibiotics and the insertion of permanent transvenous cardiac pacemakers. J. Thorac. Cardiovasc. Surg. 75, 219-223 (1978).

Austin, J. L., Preis, L. K., Crampton, R. S., Beller, G. A. & Martin, R. P. Analysis of pacemaker malfunction and complications of temporary pacing in the coronary care unit. Am. J. Cardiol. 49, 301-306 (1982).

Lumia, F. J. & Rios, J. C. Temporary transvenous pacemaker therapy: an analysis of complications. Chest 64, 604-608 (1973).

Donovan, K. D. & Lee, K. Y. Indications for and complications of temporary transvenous cardiac pacing. Anaesth. Intensive Care 13, 63-70 (1985).

Braun, M. U. et al. Percutaneous lead implantation connected to an external device in stimulation-dependent patients with systemic infection—A prospective and controlled study. PACE—Pacing Clin. Electrophysiol. 29, 875-879 (2006).

Del Nido, P. & Goldman, B. S. Temporary epicardial pacing after open heart surgery: complications and prevention. J. Card. Surg. 4, 99-103 (1989).

Elmistekawy, E. Safety of temporary pacemaker wires. Asian Cardiovasc. Thorac. Ann. 27, 341-346 (2019).

Gutruf, P. et al. Wireless, battery-free, fully implantable multimodal and multisite pacemakers for applications in small animal models. Nat. Commun. 10, 5742 (2019).

Koo, J. et al. Wireless bioresorbable electronic system enables sustained nonpharmacological neuroregenerative therapy. Nat. Med. 24, 1830-1836 (2018).

Won, S. M. et al. Natural Wax for Transient Electronics. Adv. Funct. Mater. 28, 1801819 (2018).

Choi, Y. S., Koo, J. & Rogers, J. A. Inorganic materials for transient electronics in biomedical applications. MRS Bull. 45, 103-112 (2020).

Makadia, H. K. & Siegel, S. J. Poly Lactic-co-Glycolic Acid (PLGA) as Biodegradable Controlled Drug Delivery Carrier. Polymers (Basel). 3, 1377-1397 (2011).

Hwang, S. W. et al. Dissolution chemistry and biocompatibility of single-crystalline silicon nanomembranes and associated materials for transient electronics. ACS Nano 8, 5843-5851 (2014).

Yin, L. et al. Mechanisms for Hydrolysis of Silicon Nanomembranes as Used in Bioresorbable Electronics. Adv. Mater. 27, 1857-1864 (2015).

Yin, L. et al. Dissolvable metals for transient electronics. Adv. Funct. Mater. 24, 645-658 (2014).

Length, F. Chemical and structural characterization of Candelilla (*Euphorbia antisyphilitica* Zucc.). J. Med. Plants Res. 7, 702-705 (2013).

Winter, K. F., Hartmann, R. & Klinke, R. A stimulator with wireless power and signal transmission for implantation in animal experiments and other applications. J. Neurosci. Methods 79, 79-85 (1998).

Dinis, H., Colmiais, I. & Mendes, P. M. Extending the limits of wireless power transfer to miniaturized implantable electronic devices. Micromachines 8, 359 (2017).

Kang, S. K. et al. Bioresorbable silicon electronic sensors for the brain. Nature 530, 71-76 (2016).

Shreiner, D. P., Weisfeldt, M. L. & Shock, N. W. Effects of age, sex, and breeding status on the rat heart. Am. J. Physiol. Content 217, 176-180 (1969).

Mačianskienė, R. et al. Evaluation of Excitation Propagation in the Rabbit Heart: Optical Mapping and Transmural Microelectrode Recordings. PLoS One 10, e0123050 (2015).

T., L. P. et al. Left Ventricular Wall Thickness and the Presence of Asymmetric Hypertrophy in Healthy Young Army Recruits. Circ. Cardiovasc. Imaging 6, 262-267 (2013).

Schwartzman, D., Chang, I., Michele, J. J., Mirotznik, M. S. & Foster, K. R. Electrical Impedance Properties of Normal and Chronically Infarcted Left Ventricular Myocardium. J. Interv. Card. Electrophysiol. 3, 213-224 (1999).

Salazar, Y., Bragos, R., Casas, O., Cinca, J. & Rosell, J. Transmural versus nontransmural in situ electrical impedance spectrum for healthy, ischemic, and healed myocardium. IEEE Trans. Biomed. Eng. 51, 1421-1427 (2004).

Clauss, S. et al. Animal models of arrhythmia: classic electrophysiology to genetically modified large animals. Nat. Rev. Cardiol. 16, 457-475 (2019).

Pichorim, S. F. Design of circular solenoid coils for maximum mutual inductance. in Proceedings of the 14th International Symposium on Biotelemetry 71-77 (1998).

[34]. Kurs, A. et al. Wireless Power Transfer via Strongly Coupled Magnetic Resonances. Science 317, 83 LP-86 (2007).

(56) References Cited

OTHER PUBLICATIONS

[35]. Rahko, P. S. Evaluation of the Skin-to-Heart Distance in the Standing Adult by Two-Dimensional Echocardiography. J. Am. Soc. Echocardiogr. 21, 761-764 (2008).
[36]. IEEE Standard for Safety Levels with Respect to Human Exposure to Radio Frequency Electromagnetic Fields, 3 kHz to 300 GHz. IEEE Std C95.Jan. 2005 (Revision of IEEE Std C95.1-1991) 1-238 (2006) doi: 10.1109/IEEESTD.2006.99501.
[37]. Choi, Y. S. et al. Biodegradable Polyanhydrides as Encapsulation Layers for Transient Electronics. Adv. Funct. Mater. 30, 2000941 (2020).
[38]. Choi, Y. S. et al. Stretchable, dynamic covalent polymers for soft, long-lived bioresorbable electronic stimulators designed to facilitate neuromuscular regeneration. Nat. Commun. 11, 5990 (2020).
[39]. Koo, J. et al. Wirelessly controlled, bioresorbable drug delivery devices with active valves that exploit electrochemically triggered crevice corrosion. Sci. Adv. 6, eabb1093 (2020).
[40]. Katsura, M., Sato, J., Akahane, M., Kunimatsu, A. & Abe, O. Current and Novel Techniques for Metal Artifact Reduction at CT: Practical Guide for Radiologists. RadioGraphics 38, 450-461 (2018).
[41]. Lee, Y. K. et al. Dissolution of Monocrystalline Silicon Nanomembranes and Their Use as Encapsulation Layers and Electrical Interfaces in Water-Soluble Electronics. ACS Nano 11, 12562-12572 (2017).
[42]. Sofia, S. J., Premnath, V. & Merrill, E. W. Poly(ethylene oxide) Grafted to Silicon Surfaces: Grafting Density and Protein Adsorption. Macromolecules 31, 5059-5070 (1998).
[43]. Nakanishi, K., Sakiyama, T. & Imamura, K. On the adsorption of proteins on solid surfaces, a common but very complicated phenomenon. J. Biosci. Bioeng. 91, 233-244 (2001).
[44]. Lee, G., Choi, Y. S., Yoon, H.-J. & Rogers, J. A. Advances in Physicochemically Stimuli-Responsive Materials for On-Demand Transient Electronic Systems. Matter 3, 1031-1052 (2020).
Sperelakis, N. & Hoshiko, T. Electrical impedance of cardiac muscle. Circ. Res. 9, 1280-1283 (1961).
Fry, C. H. et al. Cytoplasm resistivity of mammalian atrial myocardium determined by dielectrophoresis and impedance methods. Biophys. J. 103, 2287-2294 (2012).
Gabriel, S., Lau, R. W. & Gabriel, C. The dielectric properties of biological tissues: II. Measurements in the frequency range 10 Hz to 20 GHz. Phys. Med. Biol. 41, 2251-2269 (1996).
Rong, C. et al. Analysis of wireless power transfer based on metamaterial using equivalent circuit. J. Eng. 2019, 2032-2035 (2019).
AU—George, S. A., AU—Brennan, J. A. & AU—Efimov, I. R. Preclinical Cardiac Electrophysiology Assessment by Dual Voltage and Calcium Optical Mapping of Human Organotypic Cardiac Slices. JoVE e60781 (2020) doi:doi:10.3791/60781.
Caverly, R. H. & Hiller, G. The frequency-dependent impedance of p-i-n diodes. IEEE Trans. Microw. Theory Tech. 37, 787-790 (1989).
Youbok Lee. Antenna Circuit Design for RFID Applications. in microID® 13.56 MHz RFID System Design Guide 210 (Microchip, 2004).
Lau, E. W. Leads and Electrodes for Cardiac Implantable Electronic Devices. Clinical Cardiac Pacing, Defibrillation and Resynchronization Therapy (Elsevier Inc., 2017). doi: 10.1016/b978-0-323-37804-8.00011-0.
Iravanian, S., Herndon, C., Langberg, J. J. & Fenton, F. H. Theoretical Modeling and Experimental Detection of the Extracellular Phasic Impedance Modulation in Rabbit Hearts. Front. Physiol. 10, 883 (2019).
Fallert, M. A. et al. Myocardial electrical impedance mapping of ischemic sheep hearts and healing aneurysms. Circulation 87, 199-207 (1993).
Korean Intellectual Property Office (ISR/KR), "International Search Report for PCT/US2022/035089", Korea, Oct. 26, 2022.

* cited by examiner

BIORESORBABLE CARDIOVASCULAR INSTRUMENTS, AND OPERATION AND FABRICATION METHODS OF SAME

CROSS-REFERENCE TO RELATED PATENT APPLICATION

This application claims priority to and the benefit of U.S. Provisional Application No. 63/215,070, filed Jun. 25, 2021, which is incorporated herein in its entirety by reference.

STATEMENT AS TO RIGHTS UNDER FEDERALLY-SPONSORED RESEARCH

This invention was made with government support under HL141470 awarded by the National Institutes of Health. The government has certain rights in the invention.

FIELD OF THE INVENTION

The present invention relates generally to healthcare, and more particularly to a bioresorbable, leadless, battery-free, and fully implantable cardiovascular instruments for control of cardiac rate and rhythm during a stable operating time-frame that subsequently undergoes complete dissolution and clearance via natural biological processes.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Implantable permanent cardiac pacemakers are the cornerstone of therapy for bradyarrhythmias and atrioventricular (AV) block. As a complement to traditional pacemakers designed as permanent implants, temporary systems provide essential demand-based atrial and/or ventricular pacing for patients where bradyarrhythmias and AV block are expected to be short-lived, such as on the orders of days or weeks. Such devices act as a bridge to permanent pacing therapy or are implemented temporarily following cardiac surgery when post-surgical bradycardia is frequently encountered. Temporary pacing systems include an external generator with one or two transcutaneous pacing leads that are placed, depending on the clinical context, either epicardially or endocardially via a transvenous approach. This hardware, however, carries significant risks of complications. First, bacteria can form biofilms on the foreign materials/devices such as pacing leads, and the transcutaneous access can serve as a route for infections. Second, because the device is not fully implanted, the externalized power supply and control system can be inadvertently dislodged when caring for or mobilizing the patient. Third, removal of temporary transcutaneous devices following completion of therapy can cause laceration and perforation of the myocardium since the pacing leads can become enveloped in fibrotic tissue at the electrode-myocardium interface. These circumstances create a unique need for an alternative temporary pacemaker technology that can deliver the necessary electrotherapy while addressing the associated physiological complications.

SUMMARY OF THE INVENTION

In one aspect, the invention relates to a device implantable on a target of interest of a subject for pacemaker, cardiac neuromodulation, and/or defibrillator therapy. In one embodiment, the device comprises a wireless power harvesting unit comprising an antenna for delivering electrical stimuli to the target of interest; and a pair of electrodes, each electrode having a first end electrically connecting to the wireless power harvesting unit and a second end attachable to the target of interest.

In one embodiment, the antenna comprises a loop antenna having at least one coil.

In one embodiment, the loop antenna is in a bilayer, dual-coil configuration having two coils electrically connected to one another in series and a dielectric interlayer positioned between the two coils.

In one embodiment, the dielectric interlayer comprises one or more of poly(lactide-co-glycolide) (PLGA), polyurethane, polyanhydride, and poly(dimethyl siloxane) (PDMS).

In one embodiment, the dielectric interlayer has a thickness in a range of about 1-800 μm.

In one embodiment, each of the two coils is formed of a metallic conductive material comprising magnesium (Mg), tungsten (W), molybdenum (Mo), iron (Fe), and/or zinc (Zn) in a single-layered structure or a multiple-layered structure, or an alloy thereof.

In one embodiment, each of the two coils comprises a two-layered structure of tungsten-coated magnesium (W/Mg).

In one embodiment, the two coils have a width in a range of about 200 nm-500 μm, and a thickness in a range of about 1-800 μm.

In one embodiment, the wireless power harvesting unit further comprises a radiofrequency (RF) PIN diode electrically coupled between the antenna and one of the pair of electrodes.

In one embodiment, the RF PIN diode comprises a doped polycrystalline or monocrystalline semiconductor material, or a two-dimensional semiconductor material, or a combination of them.

In one embodiment, the two-dimensional semiconductor material comprises transition metal dichalcogenides, and/or hexagonal boron nitride.

In one embodiment, the doped polycrystalline or monocrystalline semiconductor material comprises silicon (Si), gallium (Ga), gallium arsenide (GaAs), and/or zinc oxide (ZnO).

In one embodiment, the RF PIN diode comprises a doped monocrystalline silicon nanomembrane (Si NM) having a thickness in a range of about 20-1000 nm.

In one embodiment, the RF PIN diode is configured such that a layout of RF PIN diode tomography allows for a capacitor-free rectifier with high efficiency to realize improved power transfer to the device.

In one embodiment, the wireless power harvesting unit further comprises interconnections electrically connecting the PIN diode to the antenna and said electrode.

In one embodiment, the interconnections are formed of a composite paste comprising conductive particles including W and/or Mo, or a two-dimensional conductive material such as MXenes, or a combination of them.

In one embodiment, the pair of electrodes is flexible, such that the electrode length and/or the distance between the pair of electrodes are adjustable.

In one embodiment, the second end of each electrode includes a contact pad for attaching said electrode to the target of interest.

In one embodiment, the pair of electrodes is of a metallic conductive material comprising Mg, W, Mo, Fe, and/or Zn in a single-layered structure or a multiple-layered structure, or an alloy thereof.

In one embodiment, the device further comprises an encapsulation structure surrounding the device.

In one embodiment, the encapsulation structure comprises one or more of top and bottom layers formed of PLGA, polyurethane, polyanhydride, and/or PDMS.

In one embodiment, the encapsulation layer has a thickness in a range of about 50-500 μm.

In one embodiment, the contact pad is at least partially exposed from the encapsulation structure, so that when sutured, said electrode is in contact with the target of interest.

In one embodiment, the device is configured to be eliminable completely from the target of interest of the subject through natural chemical/biochemical processes of hydrolysis and/or metabolic actions, over a subsequent timeframe following completion of therapy.

In one embodiment, the device is compatible with computed tomography (CT) for non-invasive monitoring of the bioresorption process.

In one embodiment, the device is configured to be a thin, lightweight, flexible, bioresorbable, implantable, leadless cardiac pacemaker, cardiac neuromodulator, and/or defibrillator operating in a battery-free fashion and being externally controllable and programmable.

In another aspect, the invention relates to a device implantable on a target of interest of a subject for pacemaker and/or defibrillator therapy. The device comprises a wireless power harvesting unit configured to deliver power via resonant inductive coupling to the target of interest for stimulation in a manner that eliminates need for batteries and allows for externalized control without transcutaneous leads.

In one embodiment, the wireless power harvesting unit comprises a wireless receiver including one or more inductive coils, an RF PIN diode, and a dielectric interlayer that acts as a power harvester and control interface.

In one embodiment, in operation, electrical waveform is generated by an external waveform generator and transferred to the wireless receiver of the device, and the received waveform is transformed into a direct current output via the RF PIN diode to stimulate tissue of the target of interest.

In one embodiment, each of the one or more inductive coils is formed of a metallic conductive material comprising Mg, W, Mo, Fe, and/or Zn in a single-layered structure or a multiple-layered structure, or an alloy thereof.

In one embodiment, the RF PIN diode comprises a doped polycrystalline or monocrystalline semiconductor material, or a two-dimensional semiconductor material, or a combination of them.

In one embodiment, the two-dimensional semiconductor material comprises transition metal dichalcogenides, and/or hexagonal boron nitride.

In one embodiment, the doped polycrystalline or monocrystalline semiconductor material comprises Si, Ga, GaAs, and/or ZnO.

In one embodiment, the RF PIN diode comprises a doped monocrystalline silicon nanomembrane (Si NM).

In one embodiment, the device further comprises interconnections electrically connecting the one or more inductive coils to the RF PIN diode.

In one embodiment, the interconnections are formed of a composite paste comprising conductive particles including W and/or Mo, or a two-dimensional conductive material such as MXenes, or a combination of them.

In one embodiment, the device further comprises In one embodiment, each of the pair of flexible extension electrodes is formed of a metallic conductive material comprising Mg, W, Mo, Fe, and/or Zn in a single-layered structure or a multiple-layered structure, or an alloy thereof.

In one embodiment, each of the pair of flexible extension electrodes is provided with a contact pad at its distal end to the one or more inductive coils or the RF PIN diode for interfacing with tissue of the target of interest.

In one embodiment, the device further comprises an encapsulation structure surrounding the device, excluding the contact pad.

In one embodiment, the encapsulation structure comprises one or more of top and bottom layers formed of PLGA, polyurethane, polyanhydride, and/or PDMS.

In one embodiment, the device is flexible such that device dimensions are alterable by adjusting a length of the extension electrodes to meet requirements for a target application.

In one embodiment, the device has a miniaturized geometry that facilitates full implantation into the target of interest of the subject to eliminate the need for percutaneous hardware, thereby minimizing the risk of device-associated infections and dislodgement.

In one embodiment, the device is capable of effectively capturing and sustaining cardiac rhythms across different species and platforms.

In one embodiment, the device is eliminable completely from the target of interest of the subject through natural chemical/biochemical processes of hydrolysis and/or metabolic actions, over a subsequent timeframe following completion of therapy.

In one embodiment, the device is fully bioresorbable, implantable, leadless cardiac pacemaker operating in a battery-free fashion and being externally controllable and programmable.

In yet another aspect, the invention relates to a method of making a leadless and battery-free cardiac pacemaker and/or defibrillator. The method in one embodiment comprises forming a wireless receiver; forming an RF PIN diode electrically coupled to the wireless receiver; forming a pair of flexible electrodes electrically connecting the wireless receiver and the RF PIN diode, respectively; and assembling the wireless receiver, the RF PIN diode and the flexible electrodes on a bioresorbable encapsulation structure comprising one or more of top and bottom layers formed of PLGA, polyurethane, polyanhydride, and PDMS.

In one embodiment, the wireless receiver comprises a loop antenna in a bilayer, dual-coil configuration having two inductive coils electrically connected to one another in series and a dielectric interlayer positioned between the two coils.

In one embodiment, each of the two inductive coils is formed of a metallic conductive material comprising Mg, W, Mo, Fe, and/or Zn in a single-layered structure or a multiple-layered structure, or an alloy thereof.

In one embodiment, the dielectric interlayer comprises one or more of PLGA, polyurethane, polyanhydride, and PDMS.

In one embodiment, said forming the wireless receiver comprises: defining Mg coil structures on a temporary substrate; depositing W on the Mg coil structures to form double-layered W/Mg coils; and transferring the double-layered W/Mg coils onto the dielectric interlayer to serve as the loop antenna for power harvesting In one embodiment, said defining the Mg RF coil structure is performed by laser-cutting, and said depositing W on the Mg coil structures is performed by sputter coating.

In one embodiment, the RF PIN diode is formed of a doped polycrystalline or monocrystalline semiconductor material, or a two-dimensional semiconductor material, or a combination of them.

In one embodiment, the two-dimensional semiconductor material comprises transition metal dichalcogenides, and/or hexagonal boron nitride.

In one embodiment, the doped polycrystalline or monocrystalline semiconductor material comprises Si, Ga, GaAs, and/or ZnO.

In one embodiment, said forming the RF PIN diode comprises solid-state diffusion of boron and phosphorus through a photolithographically defined mask of $SiO_2$ to yield the PIN RF diode with monocrystalline Si nanomembranes (Si NMs) derived from a Si-on-insulator wafer.

In one embodiment, said forming the RF PIN diode further comprises: removing buried oxide by immersion in hydrofluoric acid to release and transfer printing of the Si NMs onto a sacrificial layer of diluted poly(pyromellitic dianhydride co-4,4'-oxydianiline) (DPI) on a film of poly (methyl methacrylate) on the silicon wafer; photolithographic patterning and reactive ion etching to determine the lateral dimensions of the doped Si NMs for integration into the PIN diode; lift-off procedures applied with Mg deposited by electron beam evaporation to define electrical contacts; and spin casting an overcoat of DPI and dry etching through the underlying DPI and poly(methyl methacrylate) to define an open mesh layout, followed by immersion in acetone, to release the PIN diode for its transfer on the PLGA substrate.

In one embodiment, said forming the RF PIN diode further comprises oxygen reactive ion etching to remove the DPI layer during/after the transfer printing.

In one embodiment, said forming electrodes comprises laser-cutting a piece of Mg foil into the electrodes.

In one aspect, the invention relates to a method of transcutaneous pacing a target of interest of a subject for pacemaker and/or defibrillator therapy. The method comprises implanting a device in the target of interest, wherein the device comprises a wireless power harvesting unit comprising a receiver antenna for receiving electrical stimuli, and a pair of electrodes electrically coupled to the wireless power harvesting unit for delivering the electrical stimuli from the receiver antenna to the target of interest; and wirelessly transmitting the electrical stimuli to the receiver antenna. The electrical stimuli are delivered by the implanted device to pace the target of interest at frequency, rate, stimulation strength, and/or time period that are adjustable based on the need of the pacemaker, neuromodulator, and/or defibrillator therapy.

In one embodiment, the electrical stimuli are adapted such that the implanted device operates at a minimum power that can pace the target of interest in order to minimize voltage-induced electroporation damage to the target of interest and to limit electrochemical degradation of the electrodes.

In one embodiment, said transmitting the electrical stimuli is performed by an external transmitter antenna that is placed at a distance from the receiver antenna of the implanted device.

In one embodiment, the distance between the external transmitter antenna and the receiver antenna of the implanted device is up to about 50 cm.

In one embodiment, the external transmitter antenna and the receiver antenna are optimized for operation at a fixed input frequency in a range of about 10-15 Mhz, preferably about 13.56 MHz.

In one embodiment, the wireless power harvesting unit further comprises a radiofrequency (RF) PIN diode electrically coupled to the receiver antenna for rectifying the received electrical stimuli to DC-like pulses that are delivered by the pair of electrodes to the target of interest.

In one embodiment, the device is eliminable completely from the target of interest of the subject through natural chemical/biochemical processes of hydrolysis and/or metabolic actions, over a subsequent timeframe following completion of therapy.

In one embodiment, the device is fully bioresorbable, implantable, leadless cardiac pacemaker operating in a battery-free fashion and being externally controllable and programmable.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
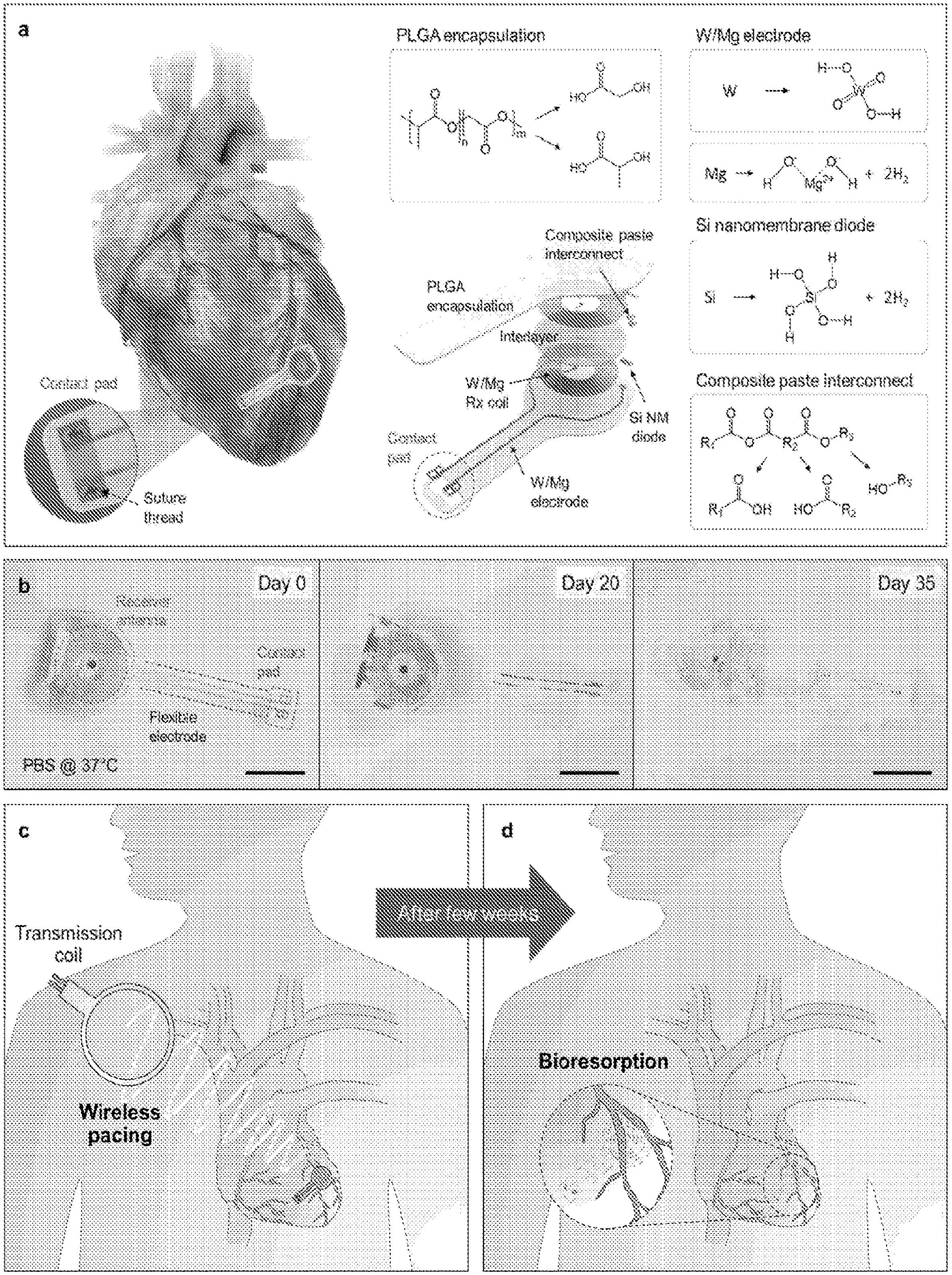
FIG. 1 shows materials, design and proposed utilization of a bioresorbable, implantable, leadless, battery-free cardiac pacemaker, according to embodiments of the invention. Panel a: (Left) Schematic illustration of the device mounted on the myocardial tissue. (Middle) The electronic component is composed of three functional parts: i) a wireless receiver, which includes an inductive coil (W/Mg; ~700 nm/~50 μm thick), a radiofrequency PIN diode (Si NM active layer, 320 nm thick), and a dielectric interlayer (PLGA, 50 μm thick) that acts as a power harvester and control interface; ii) flexible extension electrodes (W/Mg; ~700 nm/~50 μm thick); and iii) a contact pad with exposed electrodes at the ends to interface with the myocardial tissue (inset). A composite paste of W in Candelilla wax serves as an electrical interconnect. The entire system, excluding the contact pad, rests between two encapsulation layers of PLGA (~100 μm thick). (Right) All components of the device naturally bioresorb via hydrolysis and metabolic action in the body. PLGA degrades into its monomers, glycolic and lactic acid; the W/Mg electrode degrades into $WO_x$ and $Mg(OH)_2$ respectively. The Si NM degrades into non-toxic $Si(OH)_4$. Dissolution of Candelilla wax occurs by cleavage of the ester, anhydride, and moieties via hydrolysis. Panel b: Images of dissolution of a device associated with immersion in PBS (pH=7.4) at physiological temperature (37° C.). Scale bar, 10 mm. Panel c: Schematic illustration of the wireless and battery-free operation of an implanted device via inductive coupling between an external transmission coil (Tx) and the receiver (Rx) coil on the device. Panel d: Bioresorption thereby eliminates the device after a period of therapy to bypass the need for device removal.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Whenever a range is given in the specification, for example, a temperature range, a time range, or a composition or concentration range, all intermediate ranges and subranges, as well as all individual values included in the ranges given are intended to be included in the invention. It will be understood that any subranges or individual values in a range or subrange that are included in the description herein can be excluded from the claims herein.

It will be understood that, as used in the description herein and throughout the claims that follow, the meaning of "a", "an", and "the" includes plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as “lower” or “bottom” and “upper” or “top,” may be used herein to describe one element’s relationship to another element as illustrated in the figures. It will be understood that relative terms are intended to encompass different orientations of the device in addition to the orientation depicted in the figures. For example, if the device in one of the figures is turned over, elements described as being on the “lower” side of other elements would then be oriented on “upper” sides of the other elements. The exemplary term “lower”, can therefore, encompasses both an orientation of “lower” and “upper,” depending of the particular orientation of the figure. Similarly, if the device in one of the figures is turned over, elements described as “below” or “beneath” other elements would then be oriented “above” the other elements. The exemplary terms “below” or “beneath” can, therefore, encompass both an orientation of above and below.

It will be further understood that the terms “comprises” and/or “comprising”, or “includes” and/or “including”, or “has” and/or “having”, or “carry” and/or “carrying”, or “contain” and/or “containing”, or “involve” and/or “involving”, “characterized by”, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used in the disclosure, “around”, “about”, “approximately” or “substantially” shall generally mean within 20 percent, preferably within 10 percent, and more preferably within 5 percent of a given value or range. Numerical quantities given herein are approximate, meaning that the term “around”, “about”, “approximately” or “substantially” can be inferred if not expressly stated.

As used in the disclosure, the phrase “at least one of A, B, and C” should be construed to mean a logical (A or B or C), using a non-exclusive logical OR. As used herein, the term “and/or” includes any and all combinations of one or more of the associated listed items.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Temporary cardiac pacemakers provide critical functions in pacing through periods of need during post-surgical recovery. The percutaneous leads and externalized hardware associated with these systems present, however, risks of infection and constraints on patient mobility. Furthermore, the pacing leads can become enveloped in fibrotic tissue at the electrode-myocardium interface, which thereby increases the potential for myocardial damage and perforation during lead removal.

One of the objectives of the invention is to provide a bioresorbable, leadless, and fully implantable cardiac pacemaker for post-operative control of cardiac rate and rhythm during a stable operating timeframe that subsequently undergoes complete dissolution and clearance via natural biological processes. A combined set of in vitro, ex vivo, and in vivo studies across mouse, rat, rabbit, canine, and human cardiac models demonstrates that these devices provide an effective, battery-free means for pacing hearts of various sizes with tailored geometries and timescales for operation and bioresorption. These features enable programmable cardiac pacing in a manner that overcomes all of the key disadvantages of traditional temporary pacing devices. As such, this novel cardiac pacemaker may serve as the basis for the next generation of post-operative temporary pacing technology.

In one aspect, the invention relates to a device implantable on a target of interest of a subject for pacemaker neuromodulator, and/or defibrillator therapy. Neuromodulation targets autonomic nervous system aiming to prevent heart diseases such as heart failure and arrhythmias. In some embodiments, the device comprises a wireless power harvesting unit comprising an antenna for delivering electrical stimuli to the target of interest; and a pair of electrodes, each electrode having a first end electrically connecting to the wireless power harvesting unit and a second end attachable to the target of interest.

In some embodiments, the antenna comprises a loop antenna having at least one coil. In some embodiments, the loop antenna is in a bilayer, dual-coil configuration having two inductive coils electrically connected to one another in series and a dielectric interlayer positioned between the two coils.

In some embodiments, each of the two inductive coils is formed of a metallic conductive material comprising magnesium (Mg), tungsten (W), molybdenum (Mo), iron (Fe), and/or zinc (Zn) in a single-layered structure or a multiple-layered structure, or an alloy thereof. In some embodiments, each of the two coils comprises a two-layered structure of tungsten-coated magnesium (W/Mg). In some embodiments, the two coils have a width in a range of about 200 nm-500 μm, and a thickness in a range of about 1-800 μm.

In some embodiments, the dielectric interlayer comprises one or more of poly(lactide-co-glycolide) (PLGA), polyurethane, polyanhydride, and poly(dimethyl siloxane) (PDMS). In some embodiments, the dielectric interlayer has a thickness in a range of about 1-800 μm.

In some embodiments, the wireless power harvesting unit further comprises a radiofrequency (RF) PIN diode electrically coupled between the antenna and one of the pair of electrodes.

In some embodiments, the RF PIN diode comprises a doped polycrystalline or monocrystalline semiconductor material, or a two-dimensional semiconductor material, or a combination of them. In some embodiments, the two-dimensional semiconductor material comprises transition metal dichalcogenides, and/or hexagonal boron nitride. Transition-metal dichalcogenides are atomically thin semiconductors of the type $MX_2$, with M a transition-metal atom (Mo, W, etc.) and X a chalcogen atom (S, Se, or Te), e.g., $MoS_2$, $WS_2$, $MoSe_2$, $WSe_2$, $MoTe_2$, where one layer of M atoms is sandwiched between two layers of X atoms.

In some embodiments, the doped polycrystalline or monocrystalline semiconductor material comprises silicon (Si), gallium (Ga), gallium arsenide (GaAs), and/or zinc oxide (ZnO). In some embodiments, the RF PIN diode comprises a doped monocrystalline silicon nanomembrane (Si NM) having a thickness in a range of about 20-1000 nm.

In some embodiments, the RF PIN diode is configured such that a layout of RF PIN diode tomography allows for a capacitor-free rectifier with high efficiency to realize improved power transfer to the device.

In some embodiments, the wireless power harvesting unit further comprises interconnections electrically connecting the PIN diode to the antenna and said electrode. In some embodiments, the interconnections are formed of a composite paste comprising conductive particles including W and/or Mo, or a two-dimensional conductive material such as MXenes, or a combination of them. MXenes are a class of two-dimensional inorganic compounds. These materials include a-few-atoms-thick layers of transition metal carbides, nitrides, or carbonitrides.

In some embodiments, the pair of electrodes is flexible, such that the electrode length and/or the distance between the pair of electrodes are adjustable, whereby the device is flexible such that device dimensions are alterable by adjusting a length of the extension electrodes to meet requirements for a target application.

In some embodiments, the second end of each electrode includes a contact pad for attaching said electrode to the target of interest. In some embodiments, the pair of electrodes is of a metallic conductive material comprising Mg, W, Mo, Fe, and/or Zn in a single-layered structure or a multiple-layered structure, or an alloy thereof.

In some embodiments, the device further comprises an encapsulation structure surrounding the device. In some embodiments, the encapsulation structure comprises one or more of top and bottom layers formed of PLGA, polyurethane, polyanhydride, and/or PDMS. In some embodiments, the encapsulation layer has a thickness in a range of about 50-500 μm.

In some embodiments, the contact pad is at least partially exposed from the encapsulation structure, so that when sutured, said electrode is in contact with the target of interest.

In some embodiments, the device has a miniaturized geometry that facilitates full implantation into the target of interest of the subject to eliminate the need for percutaneous hardware, thereby minimizing the risk of device-associated infections and dislodgement.

In some embodiments, the device is capable of effectively capturing and sustaining cardiac rhythms across different species and platforms.

In some embodiments, the device is eliminable completely from the target of interest of the subject through natural chemical/biochemical processes of hydrolysis and/or metabolic actions, over a subsequent timeframe following completion of therapy.

In some embodiments, the device is compatible with computed tomography (CT) for non-invasive monitoring of the bioresorption process.

In some embodiments, the device is configured to be a thin, lightweight, flexible, bioresorbable, implantable, leadless cardiac pacemaker and/or defibrillator operating in a battery-free fashion and being externally controllable and programmable.

In another aspect, the invention relates to a method of making a leadless and battery-free cardiac pacemaker and/or defibrillator. The method in one embodiment comprises forming a wireless receiver; forming an RF PIN diode electrically coupled to the wireless receiver; forming a pair of flexible electrodes electrically connecting the wireless receiver and the RF PIN diode, respectively; and assembling the wireless receiver, the RF PIN diode and the flexible electrodes on a bioresorbable encapsulation structure comprising one or more of top and bottom layers formed of PLGA, polyurethane, polyanhydride, and PDMS.

In some embodiments, the wireless receiver comprises a loop antenna in a bilayer, dual-coil configuration having two inductive coils electrically connected to one another in series and a dielectric interlayer positioned between the two coils. In some embodiments, each of the two inductive coils is formed of a metallic conductive material comprising Mg, W, Mo, Fe, and/or Zn in a single-layered structure or a multiple-layered structure, or an alloy thereof. In some embodiments, the dielectric interlayer comprises one or more of PLGA, polyurethane, polyanhydride, and PDMS.

In some embodiments, said forming the wireless receiver comprises: defining Mg coil structures on a temporary substrate; depositing W on the Mg coil structures to form double-layered W/Mg coils; and transferring the double-layered W/Mg coils onto the dielectric interlayer to serve as the loop antenna for power harvesting In some embodiments, said defining the Mg RF coil structure is performed by laser-cutting, and said depositing W on the Mg coil structures is performed by sputter coating.

In some embodiments, the RF PIN diode is formed of a doped polycrystalline or monocrystalline semiconductor material, or a two-dimensional semiconductor material, or a combination of them. In some embodiments, the two-dimensional semiconductor material comprises transition metal dichalcogenides, and/or hexagonal boron nitride. In some embodiments, the doped polycrystalline or monocrystalline semiconductor material comprises Si, Ga, GaAs, and/or ZnO.

In some embodiments, said forming the RF PIN diode comprises solid-state diffusion of boron and phosphorus through a photolithographically defined mask of $SiO_2$ to yield the PIN RF diode with monocrystalline Si nanomembranes (Si NMs) derived from a Si-on-insulator wafer.

In some embodiments, said forming the RF PIN diode further comprises: removing buried oxide by immersion in hydrofluoric acid to release and transfer printing of the Si NMs onto a sacrificial layer of diluted poly(pyromellitic dianhydride co-4,4'-oxydianiline) (DPI) on a film of poly (methyl methacrylate) on the silicon wafer; photolithographic patterning and reactive ion etching to determine the lateral dimensions of the doped Si NMs for integration into the PIN diode; lift-off procedures applied with Mg deposited by electron beam evaporation to define electrical contacts; and spin casting an overcoat of DPI and dry etching through the underlying DPI and poly(methyl methacrylate) to define an open mesh layout, followed by immersion in acetone, to release the PIN diode for its transfer on the PLGA substrate.

In some embodiments, said forming the RF PIN diode further comprises oxygen reactive ion etching to remove the DPI layer during/after the transfer printing.

In some embodiments, said forming electrodes comprises laser-cutting a piece of Mg foil into the electrodes.

In one aspect, the invention relates to a method of transcutaneous pacing a target of interest of a subject for pacemaker and/or defibrillator therapy. The method comprises implanting a device in the target of interest, wherein the device comprises a wireless power harvesting unit comprising a receiver antenna for receiving electrical stimuli, and a pair of electrodes electrically coupled to the wireless power harvesting unit for delivering the electrical stimuli from the receiver antenna to the target of interest; and wirelessly transmitting the electrical stimuli to the receiver antenna. The electrical stimuli are delivered by the implanted device to pace the target of interest at frequency, rate, stimulation strength, and/or time period that are adjustable based on the need of the pacemaker and/or defibrillator therapy. In some embodiments, the device is eliminable completely from the target of interest of the subject through natural chemical/biochemical processes of hydrolysis and/or metabolic actions, over a subsequent timeframe following completion of therapy. In some embodiments, the device is fully bioresorbable, implantable, leadless cardiac pacemaker operating in a battery-free fashion and being externally controllable and programmable.

In some embodiments, the electrical stimuli are adapted such that the implanted device operates at a minimum power that can pace the target of interest in order to minimize voltage-induced electroporation damage to the target of interest and to limit electrochemical degradation of the electrodes.

In some embodiments, said transmitting the electrical stimuli is performed by an external transmitter antenna that is placed at a distance from the receiver antenna of the implanted device.

In some embodiments, the distance between the external transmitter antenna and the receiver antenna of the implanted device is up to about 50 cm.

In some embodiments, the external transmitter antenna and the receiver antenna are optimized for operation at a fixed input frequency in a range of about 10-15 Mhz, preferably about 13.56 MHz.

In some embodiments, the wireless power harvesting unit further comprises an RF PIN diode electrically coupled to the receiver antenna for rectifying the received electrical stimuli to DC-like pulses that are delivered by the pair of electrodes to the target of interest.

These and other aspects of the present invention are further described below. Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Fully Bioresorbable, Leadless, Battery-Free Cardiac Pacemaker

This exemplary example discloses a bioresorbable, leadless, and fully implantable cardiac pacemaker for post-operative control of cardiac rate and rhythm during a stable operating timeframe that subsequently undergoes complete dissolution and clearance via natural biological processes. A combined set of in vitro, ex vivo, and in vivo studies across mouse, rat, rabbit, canine, and human cardiac models demonstrates that these devices provide an effective, battery-free means for pacing hearts of various sizes with tailored geometries and timescales for operation and bioresorption. These features enable programmable cardiac pacing in a manner that overcomes all of the key disadvantages of traditional temporary pacing devices. As such, this novel cardiac pacemaker may serve as the basis for the next generation of post-operative temporary pacing technology.

The fully bioresorbable, implantable, leadless cardiac pacemaker operates in a battery-free fashion and is externally controlled and programmable. The device relies exclusively on materials that resorb when exposed to biofluids in a time-controlled manner via metabolic action and hydrolysis. The materials and design choices create a thin, flexible, and lightweight form that maintain excellent biocompatibility and stable function throughout a desired period of use. Over a subsequent timeframe following the completion of therapy, the devices disappear completely through natural biological processes. Wireless energy transfer via resonant inductive coupling delivers power to the system in a manner that eliminates the need for batteries and allows for externalized control without transcutaneous leads. These characteristics and a miniaturized geometry facilitate full implantation into the body to eliminate the need for percutaneous hardware, which thereby minimizes the risk of device-associated infections and dislodgement. A set of systematic animal studies reported below highlights aspects in bioresorbability, biocompatibility, and electrical functionality of this type of temporary pacemaker technology. The device can effectively capture and sustain cardiac rhythms across different species and platforms, including human cardiac slices and mouse, rat, rabbit, and canine hearts. Demonstrations in mouse models illustrate capabilities in the treatment of atrioventricular (AV) nodal heart block, a common indication for pacemaker therapy. In vivo tests with canine models suggest the feasibility of this pacemaker system for adult human patients. Device implantation in rats highlights functionality for several days without degradation followed by complete resorption within 3 months. Taken together, these results establish the foundations for a bioresorbable electronics technology designed to address unmet needs in important areas of care for cardiac patients.

Methods

Preparation of bioresorbable components and integration into leadless and battery-free cardiac pacemakers. Laser-cutting defined the Mg (50 μm thick; Solution Materials) radio frequency (RF) coil structures on temporary substrates of poly(dimethylsiloxane) (PDMS, 9:1). A sputter coating of W (700 nm thick) deposited on the Mg coil improves the contrast in CT images to allow for non-invasive imaging of the bioresorption process. The double-layered W/Mg RF coil was transferred onto a substrate of PLGA (65:35 (lactide:glycolide); Sigma-Aldrich) to serve as a receiving antenna for the power harvesting unit. Solid-state diffusion of boron (tube furnace at 1,050° C. with $N_2$ flow) and phosphorus (tube furnace at 1,000° C. with $N_2$ flow) through a photolithographically defined mask of $SiO_2$ formed by plasma-enhanced chemical vapor deposition yielded PIN RF diodes with monocrystalline Si nanomembranes (Si NMs) derived from a Si-on-insulator wafer (top silicon ~320 nm thick, p-type; Soitec). Removing the buried oxide by immersion in hydrofluoric acid allowed release and transfer printing of the Si NMs onto a sacrificial layer of diluted poly (pyromellitic dianhydride co-4,4'-oxydianiline) (DPI; ~200 nm) on a film of poly(methyl methacrylate) (~300 nm) on a silicon wafer. Photolithographic patterning and reactive ion etching determined the lateral dimensions of the doped Si NMs for integration into the PIN diodes. Lift-off procedures applied with Mg deposited by electron beam evaporation (~300 nm thick; Kurt J. Lesker Company) defined the electrical contacts. Spin casting an overcoat of DPI and dry etching through the underlying DPI and poly(methyl methacrylate) to define an open mesh layout, followed by immersion in acetone, released the PIN diodes and allowed their transfer on the PLGA substrate (~50 μm thick). Oxygen reactive ion etching removed the DPI layers during/after the transfer printing. Finally, these bioresorbable components (RF coil, PIN diode) were collected on a PLGA substrate and electrically interconnected with a biodegradable conductive W paste. Covering the coils with PLGA and stacking the system yielded a compact, double coil structure with openings for interconnections. In addition, laser-cutting a piece of Mg foil (50 μm thick) into 150-μm-wide electrodes and embedding them in PLGA produced electrical extension to the pads for the cardiac tissue interface.

Electric field distribution in heart tissue. Finite element analysis (FEA) was implemented on the commercial software COMSOL 5.2a by using the electrical current module (AC/DC Module User's Guide) to determine the electric field distribution in the heart tissue for voltages applied to magnesium electrodes with thicknesses of 50 μm. The partial differential equation for the current is $$\nabla \cdot J = Q_j \tag{1}$$

where $Q_j$ is the current source and J is the current defined as $J=\sigma E$. The electric field is given by $E=-\nabla V$, where σ is the electric conductivity and V is the electric potential in the electrode pads. The effective volume, i.e., volume with an electric field >100 mV/mm shown in panels b-c of FIG. 2, was determined from a triple integral (volume integration) over the heart tissue in the parametric study for electrode spacing (0.1-5 mm) and applied voltage (0.5-2.5V). The electrode pads and heart tissue were modeled using 4-node tetrahedral elements. Convergence tests of the mesh size were performed to ensure accuracy. The total number of elements in the models was approximately ~400,000. The material properties used in the simulation were $\varepsilon_{Mg}=1$, $\sigma_{Mg}=2.25\times10^7$ S/m for magnesium and $\varepsilon_{heart}=8\times10^6$, $\sigma_{heart}=0.1$ S/m for the heart tissue.

Figure 10:
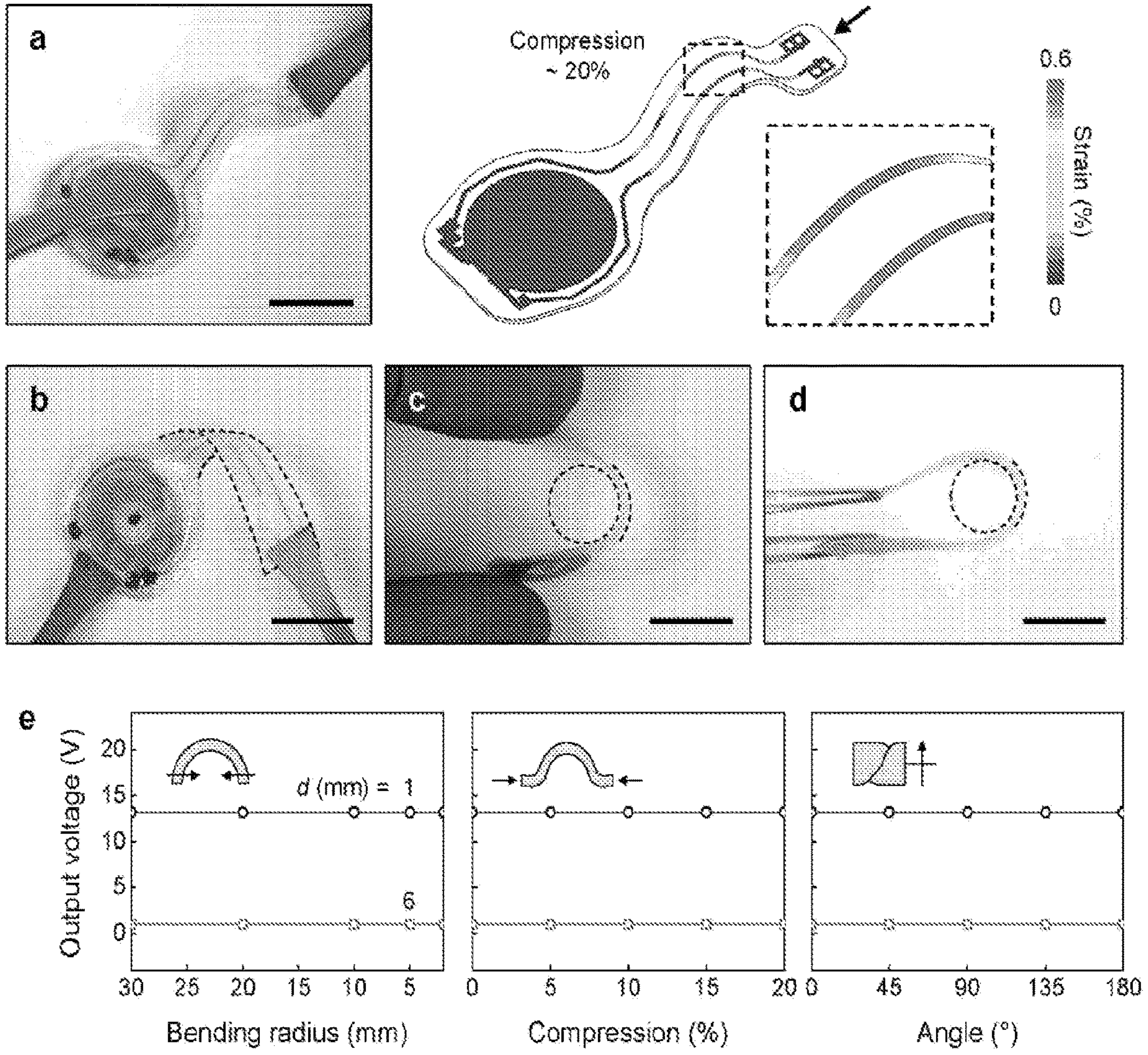
FIG. 10 shows modeling and experimental studies of mechanical reliability of the bioresorbable, leadless cardiac pacemaker, according to embodiments of the invention. Panel a: Photograph (left) and FEA (right) results for devices during compressive buckling (20%). Panels b, c, d: Photograph of twisted (180°) and bent (bend radius=4 mm) devices. Panel e: Output voltage of a device as a function of bending radius (left), compression (middle), and twist angle (right) at different distances between the Rx and Tx coils (black, 1 mm; red 6 mm). n=3 independent samples. Scale bar, 10 mm.

Simulation of mechanical characteristics. Commercial FEA software (ABAQUS, Analysis User's Manual 2016) was used to study the mechanical behaviors of the flexible Mg electrodes after deformations of physiological relevance, i.e., those associated with the surface of the heart. The electrode can experience up to ~20% compression before the strain in the metal layer reaches the yield strain (0.6%) and initiates plastic deformation (FIG. 10). The PLGA was modeled by hexahedron elements (C3D8R) while the thin Mg layer (50 μm thick) was modeled by shell elements (S4R). The minimal element size was $1/8^{th}$ of the width of the Mg wires (300 μm), which ensured the convergence of the mesh and the accuracy of the simulation results. The elastic modulus (E) and Poisson's ratio (ν) used in the analysis were $E_{Mg}=45$ GPa, $\nu_{Mo}=0.35$, $E_{PLGA}=16$ MPa, and $\nu_{PLGA}=0.5$.

Figure 21:
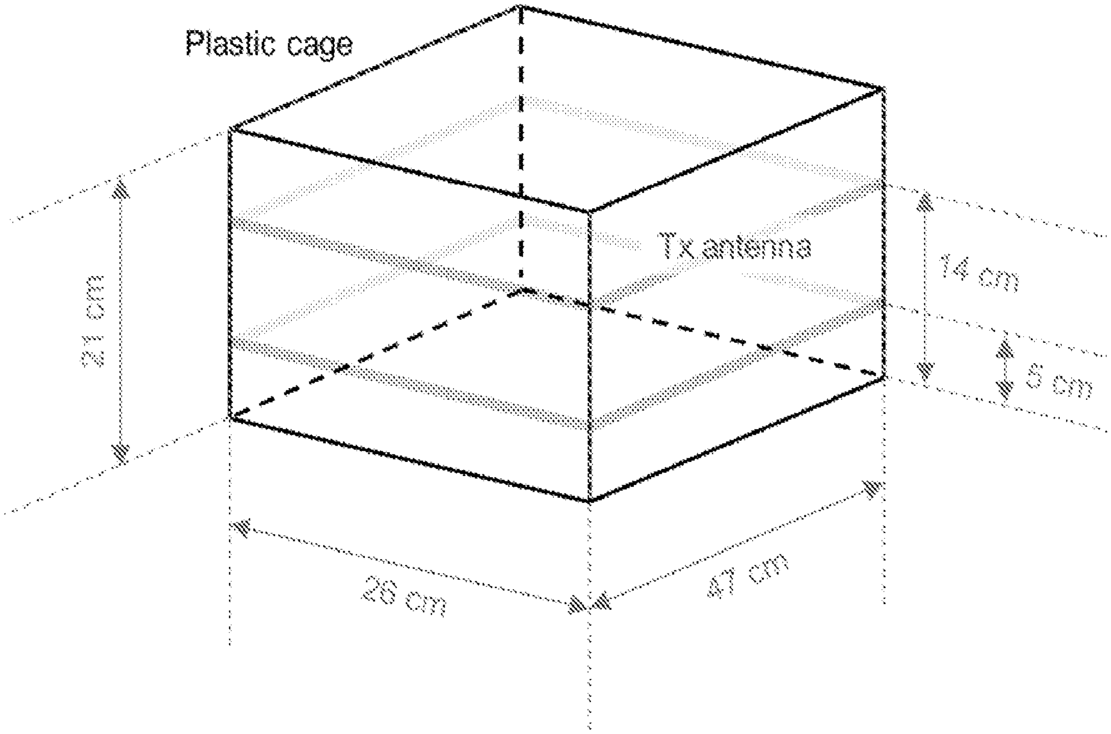
FIG. 21 shows setup for continuous, in vivo stimulation, with dimensions, according to embodiments of the invention. A custom-built plastic cage outfitted with Tx antennas provides a region within which the animal outfitted with an implanted device can freely move about for continuous in vivo pacing of the heart.

Electromagnetic simulation. The commercial software package ANSYS HFSS (ANSYS) was used to perform electromagnetic (EM) finite element analysis to 1) determine the inductance, Q factor, and scattering parameters $S_{11}$, and $S_{21}$ of the bioresorbable implantable double-layer Rx coils with outer diameters of 8 mm, 12 mm, 18 mm, and 25 mm and its corresponding matching Tx coil of the same diameter and 2) quantify the influence of Rx and Tx coil size on the power transfer efficiency and output voltage. The receiver coils with outer diameters of 8 mm, 12 mm, 18 mm, and 25 mm are tuned to operate at a resonant frequency f of 17.3 MHz, 13.91 MHz, 8.03 MHZ, and 4.24 MHz respectively, where the Q factor is maximum (panel b of FIG. 11 and panel b of FIG. 18). Lumped ports were used to obtain the scattering parameters $S_{nm}$ (panel a of FIG. 18) and port impedances $Z_{nm}$ of both the Rx and Tx coils. An adaptive mesh (tetrahedron elements) and a spherical radiation boundary (radius 1000 mm) were adopted to ensure computational accuracy. The inductance (I) and Q factor (Q) (panel b of FIG. 11 and panel b of FIG. 18), were obtained for all coils as $L_n=\mathrm{Im}\{Z_{nn}\}/(2\pi\ f)$ and $Q_n=|\mathrm{Im}\{Z_{nn}\}/\mathrm{Re}\{Z_{nn}\}|$, where $\mathrm{Re}\{Z_{nn}\}$, $\mathrm{Im}\{Z_{nn}\}$, and f represent the real and imaginary parts of $Z_{nm}$, and the working frequency, respectively. The power transfer efficiency η is related to the magnitude of the scattering parameter $S_{21}$ as $$\eta = |S_{21}|^2 \times 100\% \tag{2}$$

and the output voltage V can be calculated as $$V = \frac{S_{21} V_s}{2}\sqrt{\frac{R_L}{R_S}} \tag{3}$$

where $V_S$ and $R_S$ are the input voltage and resistance at the source and $R_L$ is the resistance of the load in the Rx coil. The relationship between power transfer efficiency and working distance was calculated for a separation of 1-30 mm (panel d of FIG. 18) between the Rx and Tx coil in all four scenarios; similarly, the relationship between the output voltage/power and working distance was obtained in panels e-f of FIG. 4. The dielectric constant (ε) and electrical conductivity (σ) used in the model are $\varepsilon_{Mg}=1$, $\sigma_{Mg}=2.25\times10^7$ S/m for the Mg coil trances in the Rx coils; $\varepsilon_{Cu}=1$, $\sigma_{Cu}=5.8\times10^7$ S/m, $\delta_{Cu}=0$ for the Cu traces in the Tx coils. Lastly, the specific absorption rate (SAR), a measure of RF energy absorption in the body, was calculated for a mouse with a 25 mm diameter Rx implant in a plastic cage with a double loop Cu wire (AWG 12) Tx antenna operating at 13.56 MHz (FIG. 21). The simplified mouse mesh ellipsoid body with major (half) axes 8, 14, and 52 mm (FIG. 22) was used to demonstrate that the SAR is well below the safety guidelines of RF exposure. The dielectric constant (ε), electrical conductivity (σ) and density (ρ) used in the mouse model are $\varepsilon_{Mouse}=40$, $\sigma_{Mouse}=0.5$ S/m, and $\rho_{Mouse}=1000$ kg/m$^3$.

In vivo studies of rat models. All procedures were performed according to protocols (A364) approved by The George Washington University Institutional Animal Care and Use Committee (IACUC) and conforming with guidance from the Guide for Care and Use of Laboratory Animals published by the National Institutes of Health (NIH). Adult male and female Sprague-Dawley rats (Hilltop Animals, Scottsdale, PA) were used. All procedures were performed under general anesthesia using inhaled isoflurane vapors (1-3%). Throughout the surgery, ventilation was provided by the VentElite small animal ventilator (Harvard Apparatus, Holliston, MA). The heart was exposed via left thoracotomy, and the pacemaker electrodes were implanted on the myocardial surface of the left ventricle using 6-0 non-resorbable monofilament sutures. The pacemaker receiver was placed within the subcutaneous pocket on the ventral surface of the rat. Subsequent layers of thoracic cavity, muscle, and skin were closed. Pacemakers were tested at the end of the procedure to verify their function and confirm adequate placement. Animals were then taken off of general anesthesia and allowed to recover. Appropriate post-operative monitoring and care were provided following surgery. For analgesia, an intraperitoneal dose of buprenorphine (0.5-1.0 mg/kg) was administered before incision and once every 12 hours for 48 hours following surgery.

Optical mapping of whole heart cardiac pacing. All procedures were performed according to protocols (Mouse: A367; Rat: A364; Rabbit: A327) approved by The George Washington University Institutional Animal Care and Use Committee (IACUC). Optical mapping was performed on ex vivo mouse and rabbit hearts. For mice, the adult mice were anesthetized with isoflurane vapors. For rabbits, the adult rabbit was anesthetized using a mixture of 50 mg/kg ketamine and 10 mg/kg xylazine. The following procedure for optical mapping was performed for both mouse and rabbit hearts: Cessation of pain was confirmed by toe pinch, the heart was excised, and the aorta was cannulated in cardioplegic solution. The heart was then placed into a constant-pressure Langendorff system where the perfused solution was a modified Tyrode's solution (128.2 mM NaCl, 4.7 mM KCl, 1.05 mM $MgCl_2$, 1.3 mM $CaCl_2$, 1.19 mM $NaH_2PO_4$, 20 mM $NaHCO_3$, 11.1 mM glucose) which was maintained at 37° C. and was bubbled with 95% $O_2$/5% $CO_2$. The pressure of the heart was maintained between 60-80 mmHg throughout the experiment. Far-field ECG signals were acquired with two sensing electrodes and one ground electrode placed into the bath around the heart and recorded using LabChart software (ADInstruments, Sydney, Australia). Mechanical motion of the heart was arrested using blebbistatin (5-10 μM), an electromechanical uncoupler. The tissue was stained with di-4-ANEPPS (125 nM), a voltage-sensitive fluorescent dye, to optically map voltage changes in the membrane potential. Signals were recorded at 1-2 kHz using a high-speed CMOS camera with the MiCAM Ultima acquisition system (SciMedia, Costa Mesa, CA). The electrode of the bioresorbable pacemaker was placed on the anterior myocardial surface of the heart. Using a function generator, the frequency (~10 MHz) and stimulating duration (1-5 msec) were set to match the settings of the device for wireless inductive power transfer. The heart was paced at a range of increasing frequencies. Capture of the heartbeat was verified by far-field ECG measurements, and the spatiotemporal dynamics of the activation of the transmembrane potential were recorded by optical mapping. To induce atrioventricular (AV) block, ischemic reperfusion was performed until $2^{nd}$ degree AV block was confirmed by ECG.

Optical mapping was also performed on ex vivo human hearts. All tissue procurement, preparation, and experiments are performed according to protocols approved by the Institutional Review Board (IRB) of The George Washington University and international guidelines for human welfare. Donor human hearts rejected for organ transplant were acquired from the Washington Regional Transplant Community (WRTC) as de-identified discarded tissue with approval from IRB of The George Washington University. Human ventricular heart slices were created according to methods previously described. The heart slice was then transferred and placed into a system perfused with a modified Tyrode's solution (NaCl 140 nN; KCl 4.5 mM; glucose 10 mM; HEPES 10 mM; $MgCl_2$ 1 mM; $CaCl_2$ 1.8 mM; pH 7.4) which was maintained at 37° C. and was bubbled with $O_2$. Optical mapping of the human ventricular heart slice was performed as previously detailed. In brief, the optical mapping methods involve the following: Mechanical motion of the slice was arrested using blebbistatin (5-10 μM), an electromechanical uncoupler. The tissue was stained with di-4-ANEPPS (125 nM), a voltage-sensitive fluorescent dye, to optically map voltage changes in the membrane potential. Signals were recorded at 1 kHz using a high-speed CMOS camera with a MICAM Ultima acquisition system (SciMedia, Costa Mesa, CA). The electrode of the bioresorbable pacemaker was placed on top of the slice in the central area. Using a function generator, the frequency (~10 MHz) and stimulating duration (1-5 msec) were set to match the settings of the device for wireless inductive power transfer. The heart slice was paced at a range of frequencies. Capture of the heartbeat was verified by evoked optical action potentials, and the spatiotemporal dynamics of the activation of the transmembrane potential were recorded by optical mapping.

Processing of data from optical mapping. Optical signals were processed using a custom MATLAB software (RHYTHM) that is openly available at https://github.com/optocardiography. Each pixel was spatially filtered with a 3×3 uniform average bin. A Finite Impulse Response filter was used to filter each temporal sequence with a cutoff frequency of 100 Hz. Baseline drift was removed using a polynomial subtraction, and the magnitude of the signals was normalized. Activation times across the membrane were determined by the time of $dV/dt_{max}$ of the recorded optical action potentials.

Chronic in vivo pacing. Pacemakers in all animals were tested daily post-procedure. Each day, animals were anesthetized with inhaled isoflurane vapors (2-3%) per protocols approved by the Institutional Animal Care and Use Committee (IACUC) at The George Washington University. The Tx antenna was placed parallel to the receiver of the implanted device to power the pacemaker and pace the heart. The frequencies of the pacing stimulation were adjusted such that the stimulation frequency was greater than that of the intrinsic rhythm of the heart. Three-lead ECG was monitored by subdermal needle electrodes in the Lead I configuration (positive electrode on the right arm, negative electrode on the left arm, ground electrode on the leg) using a PowerLab data acquisition system with the LabChart software (ADInstruments, Sydney, Australia). The heart rate was calculated from the R-R interval associated with the ECG. Daily testing in the same manner continued until the pacemaker failed to capture the heart.

Wireless operation of the bioresorbable pacemaker. A commercial RF system (Neurolux, Inc., Evanston, IL) was used to wirelessly deliver power to the bioresorbable cardiac pacemaker for whole heart stimulation. The system included the following: (1) a laptop with custom software (Neurolux, Inc., Evanston, IL) to control and command the data center, (2) a Power Distribution Control box to supply wireless power and communicate with the devices through interactive TTL inputs, (3) an antenna tuner box to maximize power transfer and match the impedance of the source and the antenna, and (4) an enclosed cage with customizable loop antenna designs for in vivo operation of the devices.

Weight monitoring, Masson's trichrome staining, and immunohistochemistry. Devices were implanted into both male and female Sprague Dawley adult rats. Animals were weighed every 3 days to monitor their weight post-surgery. n=3-6 independent animals. The hearts of animals without implanted devices (control) and those with implanted device for 3 weeks and 6 weeks were analyzed. n=3 biologically independent animals per group. Animals were euthanized using 5% isoflurane vapors at 2 mL/min oxygen flow with an EZ anesthesia machine (EZ Systems Inc.) until loss of consciousness. Once the cessation of pain was confirmed by toe pinch, the heart was excised for euthanasia by exsanguination. The excised hearts were immediately cannulated and retrograde-perfused first with cardioplegic solution and then with neutral-buffered formalin. After 24 hours, the hearts were transferred to a 70% ethanol solution and embedded in paraffin. Cross-sections underwent either Masson's trichrome staining for assessment of fibrosis or immunohistochemical staining to visualize localization of CD45 in the myocardium.

For Masson's trichrome-stained samples, cross-sections of the anterior left ventricle were imaged at 4× magnification using an EVOS XL light microscope (Thermo Fisher Scientific). A custom MATLAB code was used to quantify the percent volume of myocytes, collagen, and interstitial space in these images. The region of interest was selected along the left ventricular free wall near the site of device implantation. Color deconvolution was performed to identify pink, blue, and white pixels which represent myocytes, collagen, and interstitial space, respectively. The percent volume encompassed by each of these structures was quantified by calculating the relative number of pixels per color in the selected region of interest.

For immunohistochemistry, sections were stained using the peroxidase/avidin-biotin-complex method. Briefly, the procedure was performed as follows: Sections were deparaffinized using xylene and dehydrated using a gradient of concentration of ethanol. Antigen retrieval was performed using citrate buffer (pH=6.0) in a pressure cooker for 10 minutes. Slides were washed 3 times with ultra-pure deionized $H_2O$ (3 min/wash). Endogenous peroxidase activity was blocked with BLOXALL solution (SP-6000, Vector Laboratories) for 10 minutes. Slides were again washed 3 times with ultra-pure de-ionized $H_2O$ (3 min/wash). Samples were blocked for another 30 minutes with normal goat blocking buffer (PBS, 0.15% Triton X-100, 1% BSA, 3% goat serum (005000121, Jackson ImmunoResearch)) and incubated with the CD45 primary antibody overnight at 4° C. (1:50; ab 10558, Abcam). Next, the samples were washed in PBS with 0.5% Triton X-100 and 2 times in PBS (3 min/wash). Slides were incubated at room temperature with a biotinylated goat anti-rabbit IgG secondary antibody (1:500; 65-6140, Invitrogen) for 60 minutes and with an avidin biotin complex (ABC) reagent (PK-6100, Vector Laboratories) for 30 minutes. Samples were rinsed 3 times in PBS (3 min/wash) before and after application of the ABC reagent. Chromogenic development was achieved using the DAB Peroxidase Substrate Kit (SK-4100, Vector Laboratories). Samples were counterstained with hematoxylin (6765007, Thermo Scientific) for 10 minutes, rinsed with tap water until colorless, and dehydrated in an increasing gradient of ethanol followed by xylene. Slides were mounted with DPX mountant (13512, Electron Microscopy Sciences), and the images near the site of pacemaker implantation were taken using brightfield microscope (DMi8, Leica Microsystems) in a tiled manner at 20× and 40× magnification using the Leica Application Suite (LAX) X software (Leica Microsystems). $CD45^+$ cells were manually quantified in a blinded manner using ImageJ (v2.1.0, National Institutes of Health). Each counted cell was marked so that no cell was counted twice. A custom MATLAB code quantified the myocardial volume in each image using color deconvolution and calculated the frequency of $CD45^+$ cells per $mm^2$. To determine statistical differences, a non-parametric Kruskal-Wallis one-way analysis of variance with Dunn's test for pairwise comparison was performed across each condition between the 0-week (control), 3-week, and 6-week endpoints at a significance level of $p<0.05$.

Evaluation of hematology and blood chemistry of rats. All procedures followed protocols approved by The George Washington University Institution Animal Care and Use Committee (IACUC). Blood was collected from adult rats with bioresorbable pacemakers implanted using the aforementioned surgical procedures. At 1, 3, 5, and 7-week endpoints, blood was collected from animals via the tail vein into K-EDTA and gel tubes for blood counts and blood chemistry tests, respectively. Charles River Laboratories conducted the assays.

In vivo canine model study. Retired breeder female hound dogs (age 1.2-3.5 years, weight 27-36 kg) used in this study were maintained in accordance to the Guide for the Care and Use of Laboratory Animals published by the U.S. National Institutes of Health (NIH Publication No. 85-23, revised 1996) as approved by the IACUC of Northwestern University. Prior to surgery, all animals were premedicated with acepromazine (0.01-0.02 mg/kg) and were induced with propofol (3-7 mg/kg). General anesthesia (inhaled) was achieved with isoflurane (1-3%) after intubation. Adequacy of anesthesia was assessed by toe pinch and palpebral reflex. Surface electrodes were applied to the limbs and continuous 6-lead ECG was recorded at a sampling rate of 977 Hz (Prucka CardioLab). A lateral thoracotomy was performed, and the heart was exposed by pericardiectomy. The electrodes of implanted bioresorbable pacemakers were sutured to the myocardial surface of the right ventricle with 4-0 monofilament non-resorbable sutures. For in vivo long-range tests of wireless operation, the thoracotomy was closed in 4 layers (ribcage, deep fascia and muscles, subcutaneous tissue, and skin). A chest tube was placed prior to closing. The chest was evacuated of air and fluid, and lungs re-expanded. The chest tube was clamped. The antenna was applied at various distances from the receiver, and the selected pacing cycle length was 30-60 ms shorter than the intrinsic ventricular cycle length. Effective ventricular capture was confirmed by surface ECG. Upon finishing the in vivo portion of the study and after confirming a very deep plane of anesthesia, the heart was removed, and euthanasia was achieved by exsanguination.

In vivo bioresorption study. Rats were anesthetized during imaging, with a preclinical microCT imaging system (nanoScan PET/CT, Mediso-USA, Boston, MA). Data was acquired with a 2.2× magnification, <60 μm focal spot, 1×4 binning, with 720 projection views over a full circle, using 70 kVp/240 μA, with a 300 ms exposure time. The projection data was reconstructed with a voxel size of 68 μm (in all directions) and using filtered (Butterworth filter) back projection software from Mediso. Amira 2020.1 (FEI Co, Hilsboro, OR) was used to segment the device and skeleton, followed by 3D rendering.

Statistical analysis. Results are reported as mean±6 SD, unless otherwise noted. Statistical analyses were performed using Statistical software (Version 6.0, Statsoft, Tulsa, Oklahoma) followed by a t-test. *$p<0.05$, $p<0.01$, *$p<0.001$. All experiments were performed with at least 3 biological replicates per condition. For quantitative histology and immunohistochemistry analysis, significance in column comparisons was calculated with a non-parametric Kruskal-Wallis test with Dunn's multiple comparison test at a significance level of $p<0.05$. For echocardiography data, significance in column comparisons was calculated using a Friedman test in conjunction with Dunn's multiple comparison test at a significance level of $p<0.05$.

Results and Discussion

Figure 9:
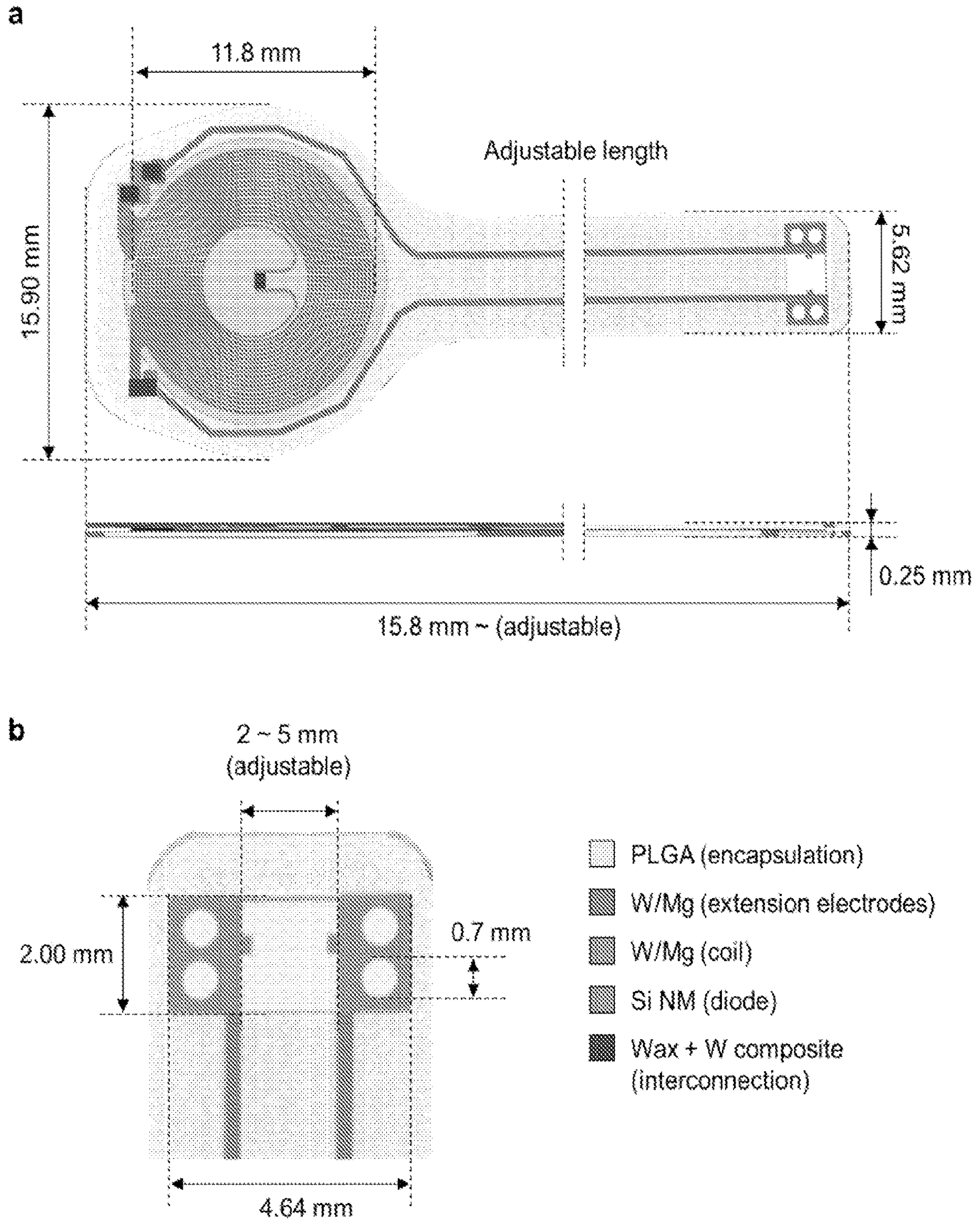
FIG. 9 shows design of bioresorbable, implantable, leadless, battery-free cardiac pacemaker, according to embodiments of the invention. Panel a: Dimensions of the device: (top) x,y-view; (bottom) x,z-view. The minimum length of the device is 15.8 mm. The total length can be altered to meet requirements for the target application, simply by changing the length of the extension electrode. Panel b: Dimensions of the contact pad. PLGA encapsulation covers the top surface of the contact electrode to leave only the bottom of contact electrode exposed.

Design and Battery-Free Operation of a Bioresorbable Cardiac Pacemaker. The schematic illustration in panel a of FIG. 1 (left) shows a thin, flexible, bioresorbable, leadless cardiac pacemaker on the surface of a heart. As part of the surgical implantation process, an integrated contact pad that contains two dissolvable metallic electrodes (i.e., bipolar channels) is attached to the myocardium. As shown in panel a of FIG. 1 (middle), the wireless power harvesting part of the system includes a loop antenna with a bilayer, dual-coil configuration (tungsten-coated magnesium (W/Mg); ~700 nm/~50 μm thick), a film of a poly(lactide-co-glycolide) (PLGA) 65:35 (lactide:glycolide) as a dielectric interlayer (~50 μm thick), and a radiofrequency (RF) PIN diode based on a doped monocrystalline silicon nanomembrane (Si NM; ~320 nm thick). A strip of double layered electrode (W/Mg; ~700 nm/~50 μm thick) with an opening at the end serves as an electrical extension and connector to deliver electrical stimuli from this receiver (Rx) antenna to the myocardium. This W/Mg electrode design enables compatibility with computed tomography (CT) for non-invasive monitoring of the bioresorption process. The layout of the PIN diode tomography allows for a capacitor-free rectifier with high efficiency to realize improved power transfer to the device (EXAMPLE 2). CT-compatibility for non-invasive monitoring and low frequency PIN diode for efficient capacitor-free device further enhance the device's ability for effective electrotherapy are key advancements from analogous peripheral nerve stimulators reported previously. The exposed pair of electrodes (2.0×1.4 $mm^2$) includes adjacent holes (700 μm diameter) as points for suturing to the heart with bioresorbable suture (Ethicon, MV-J451-V), as shown in panel a of FIG. 1 (inset). A composite paste of Candelilla wax and tungsten (W) micro-particles provides electrical interconnections. Two layers of PLGA 65:35 define a top and bottom encapsulation (100 μm thickness) structure around the entire system to isolate the active materials from the surrounding biofluids during the period of implantation. The geometry of the entire system is small, thin (~0.05 cc; width: ~16 mm; length: >15 mm; thickness: ~250 μm), and lightweight (~0.3 g), as shown in FIG. 9.

The key defining characteristic of this system is that all of the constituent materials are bioresorbable. The designs support stable function over a relevant time frame with eventual complete disappearance into the surrounding biofluids and eventually from the body itself by natural chemical/biochemical processes of hydrolysis and metabolic action (panel a of FIG. 1, right). For example, PLGA dissolves by hydrolysis into its monomers, glycolic and lactic acid. The Mg, Si NM and W disappear into non-toxic products, according to ($Mg+2H_2O \rightarrow Mg(OH)_2+H_2$), ($Si+4H_2O \rightarrow Si(OH)_4+2H_2$), and ($2W+2H_2O+3O_2 \rightarrow 2H_2WO_4$), respectively. The Candelilla wax, which contains long-chain poly- and mono-unsaturated esters, fatty acids, anhydrides, short-chain hydrocarbons, and resins, undergoes hydrolysis and resorbs into the body. Panel b of FIG. 1 shows photographs of a typical device at various time points following immersion in a phosphate-buffered saline (PBS, pH 7.4) solution at physiological temperature (37° C.). The constituent materials largely dissolve within five weeks, and the remaining residues completely disappear after seven weeks.

Panels c-d of FIG. 1 illustrate the mode of use for this bioresorbable technology. Electrical stimulation is delivered by the implanted device to pace the heart at various rates, stimulation strengths, and time periods by wireless power transfer according to the clinical need throughout the post-operative period (panel c of FIG. 1). After resolution of bradycardia or insertion of a permanent device, temporary pacing is no longer necessary. Here, processes of bioresorption naturally eliminate the device completely without need for surgical extraction, as shown in panel d of FIG. 1. The current clinical device of pacemakers presents complications associated with external and percutaneous hardware as well as the risk related to removal. In comparison, this novel device disclosed herein allows for a new clinical implementation scheme where the device is fully implanted because of its battery-free leadless geometry and its self-elimination by bioresorption.

Optimized mechanical layouts ensure conformal contact against the curved surface of the heart for effective and reliable pacing. Three-dimensional finite-element modeling (FEM) reveals distributions of principal strain for compression-induced buckling perpendicular to the length of the interconnects, as shown in panel a of FIG. 10. On the basis of the layouts and the mechanical moduli, the maximum strains in the Mg electrodes and PLGA encapsulation are less than 0.6% for a compression of 20%, corresponding to the linear elastic regime for each of these materials. Images of the device during twisting (180°) and bending (bend radius=4 mm) highlight additional features of the flexible mechanics, as shown in panels a-d of FIG. 10. Wireless electrical measurements before and after twisting, compressing (i.e., buckling), and bending show negligible differences in output voltage, consistent with expectations based both on FEM and analytical modeling results, as shown in panel e of FIG. 10.

Figure 11:
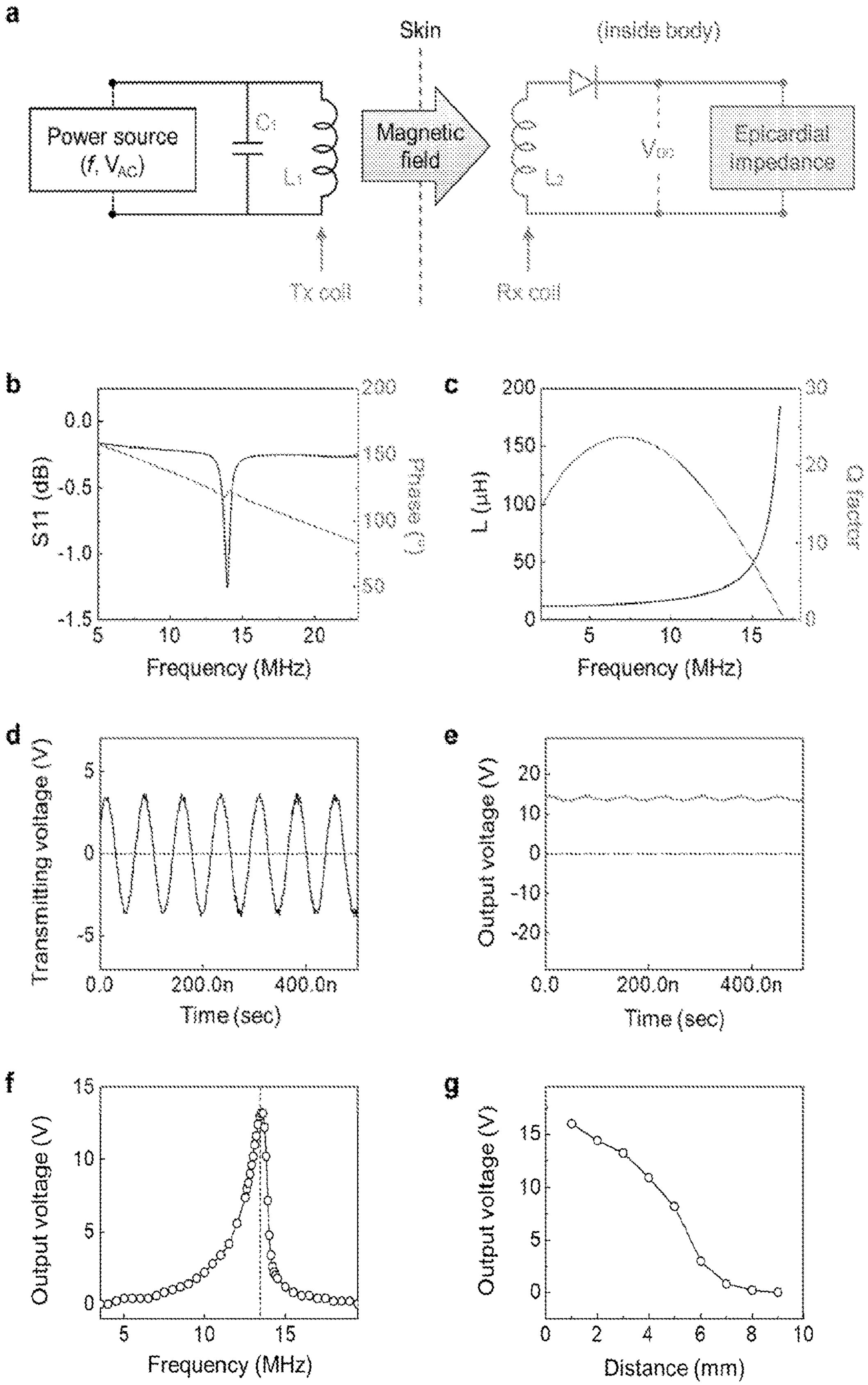
FIG. 11 shows electrical performance characteristics of the wireless power transfer system, according to embodiments of the invention. Panel a: Schematic illustration of the circuit diagram for the transmission of RF power. Monophasic electrical pulses (programmed duration; alternative current) are generated by a waveform generator at ~13.5 MHz (Agilent 33250A, Agilent Technologies, USA). The voltage can be further increased with an amplifier (210L, Electronics & innovation, Ltd., USA). The generated waveforms (i.e., input power) are delivered to the Tx coil (3 turns, 20 mm diameter). This RF power is transferred to the Mg Rx coil (17 turns, 12 mm diameter) of an implanted bioresorbable cardiac pacemaker. The received waveform is transformed into a direct current output via the RF diode to stimulate the targeted tissue. Panel b: Measured RF behavior of the stimulator (black, $S_{11}$; red, phase). The resonance frequency is ~13.5 MHz. Panel c: Simulation results for inductance (L) and Q factor as a function of frequency. Panel d: An alternating current (sine wave) applied to the Tx coil. The resonance frequency and input voltage (i.e., transmitting voltage) are ~13.5 MHz and 7 $V_{pp}$, respectively. Panel e: Example direct current output of ~13.2 V wirelessly generated via the Rx coil of the bioresorbable device. Panel f: Output voltage as a function of transmitting frequency. At the resonance frequency (~13.5 MHZ) of the receiver coil (transmitting voltage=7 V), the device produces a maximum output voltage of ~13.2 V. Panel g: Output voltage as a function of the distance between the Tx and Rx coils (transmitting voltage=10 $V_{pp}$; transmitting frequency=~13.5 MHz).

FIG. 11 summarizes the electromagnetic characteristics of the bioresorbable device for wireless and battery-free operation. Alternating currents (sine wave) generated by a function generator provide a source of monophasic RF power to a transmission (Tx) antenna (i.e., primary coil) placed near the harvester component of the device. The Rx coil (i.e., secondary coil) transforms the received waveform to an approximately direct current output via the RF diode and delivers it to the interface with the myocardium (panel a of FIG. 11) as a cathodic direct current pulse through the electrode pads. An applied electrical stimulus above a threshold value initiates cardiac excitation as a result of depolarization of the transmembrane potential (i.e., the difference in voltage between the inside and outside of the cell). This type of inductive scheme is common for wireless power transfer in implanted medical devices because the magnetic coupling that occurs in this megahertz frequency regime (panels b-c and f of FIG. 11; ~13.5 MHz) avoids absorption by biofluids or biological tissues. Panels d-e of FIG. 11 illustrate the continuous RF transmitting power (~7 $V_{pp}$ at a 1 mm coupling distance) applied to the Tx antenna and the resultant monophasic output (13.2 V) at the contact pad.

Figure 13:
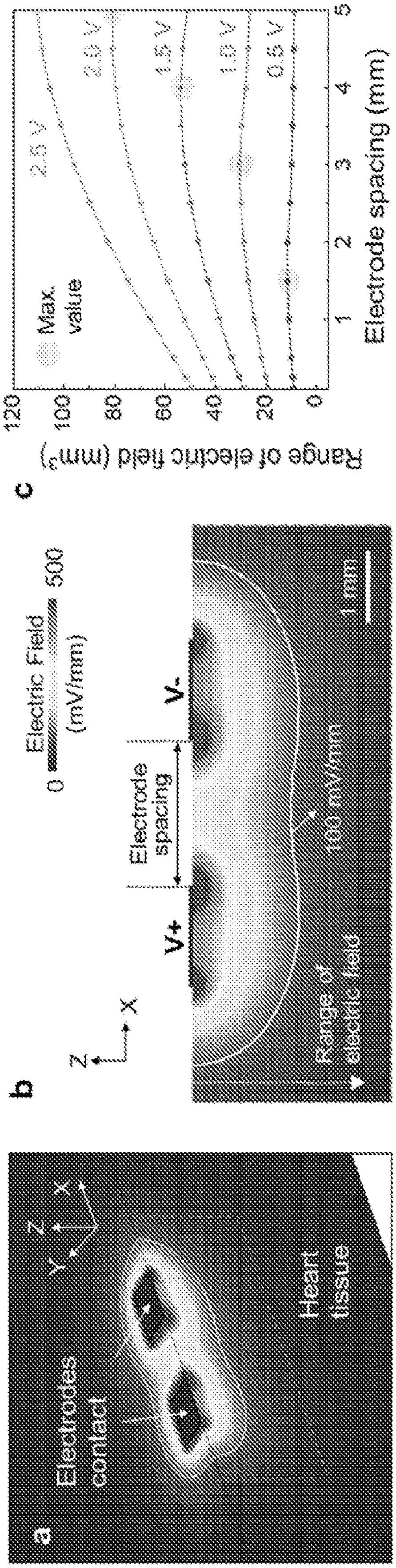
FIG. 13 shows finite element analysis (FEA) simulations of the electric field distributions near the electrode-myocardium interface upon electrical stimulation, according to embodiments of the invention. Panels a, b: Computational results for distributions of the electric field within the cardiac tissue and relationships to design parameters associated with the contact electrodes in three-dimensional (3D) and two-dimensional (2D; x, z-axis) space, respectively. Panel c: Simulated range of electric field as a function of electrode spacing with different input voltages at an electric field strength of 100 mV/mm (black, 0.5 V; red, 1.0 V; blue, 1.5 V; green, 2.0 V; violet, 2.5 V). The yellow circles indicate the maximum range of electric field and the corresponding electrode spacing at the specific input voltage. These results show that this bipolar electrode design generates a strong electric field and that transmitting voltages and interelectrode distance influence the range, and therefore strength, of the produced electric field.

Ex Vivo Electrical Pacing in Various Cardiac Systems: Mouse, Rabbit ad Human. Various ex vivo tests establish the operating features of the device and its efficacy in pacing. Three different cardiac systems with various wall thicknesses (mouse, ~0.7 mm; rabbit, ~5.0 mm; human, ~10 mm) reflect the span of different impedances observed in human hearts depending on size and health status. Finite element analysis (FEA) simulations reveal the electric field distributions near the electrode-myocardium interface upon electrical stimulation (electrode spacing=2 mm; applied voltage=0.75 V) in three-dimensional (3D) and two-dimensional (2D; x, z-axis) space, as shown in panels a-b of FIG. 13, respectively. The results show that this bipolar electrode design induces a strong electric field in cardiac tissue and that different transmitting voltages and interelectrode distance influence the range, and therefore strength, of the electric field delivered by the pacemaker (panel c of FIG. 13). In practice, the desired operating point is at the minimum power that can pace the heart in order to minimize voltage-induced electroporation damage to the myocardium and to limit the electrochemical degradation of the bioresorbable electrodes. For this reason, choices of electrode spacing (from 1 mm to 5 mm) depend on the impedance, and therefore the size, of the targeted cardiac tissue (EXAMPLE 3).

Figure 2:
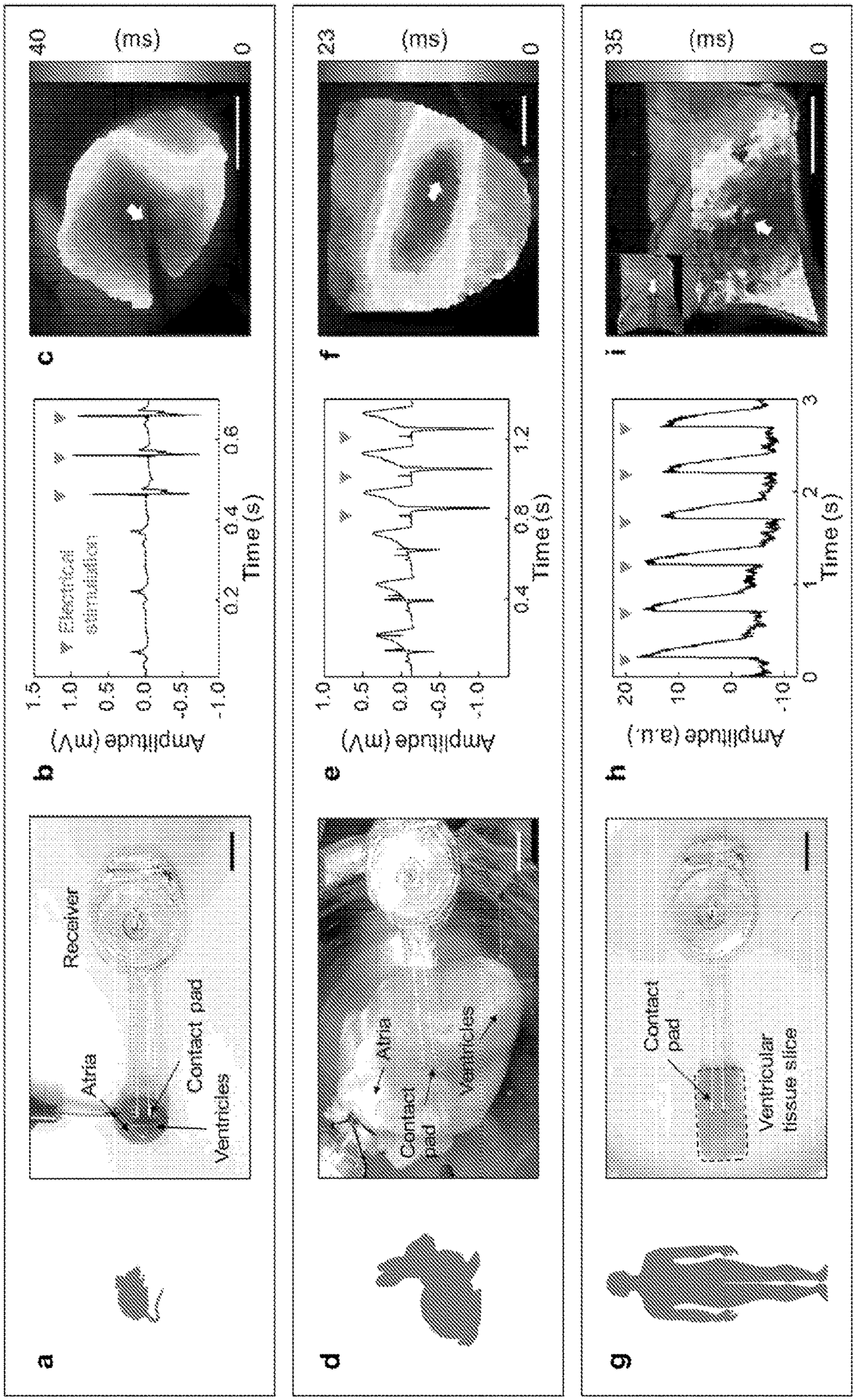
FIG. 2 shows ex vivo demonstrations of bioresorbable cardiac pacemakers on mouse and rabbit hearts, and human cardiac tissue, according to embodiments of the invention. Panels a, d, g: Images of bioresorbable cardiac pacemakers on mouse (panel a) and rabbit (panel d) hearts and a human ventricular cardiac tissue slice (panel g). Positioning of the electrode of the bioresorbable pacemaker on the anterior ventricular myocardium (panels a, d) and the surface of the human ventricular cardiac tissue slice (panel g). Scale bar, 10 mm. Panels b, e, h: Far-field ECG recordings (panels b, e) and optical action potential maps (panel h) before (white background) and during (yellow background; red arrows indicate delivered electrical stimuli) electrical stimulation using bioresorbable devices. Panels c, f, i: Activation map of membrane potential for mouse, rabbit, and human myocardium show activation originating from the location of the electrode pad of the device as indicated by the white arrow. Scale bar, 5 mm.
Figure 15:
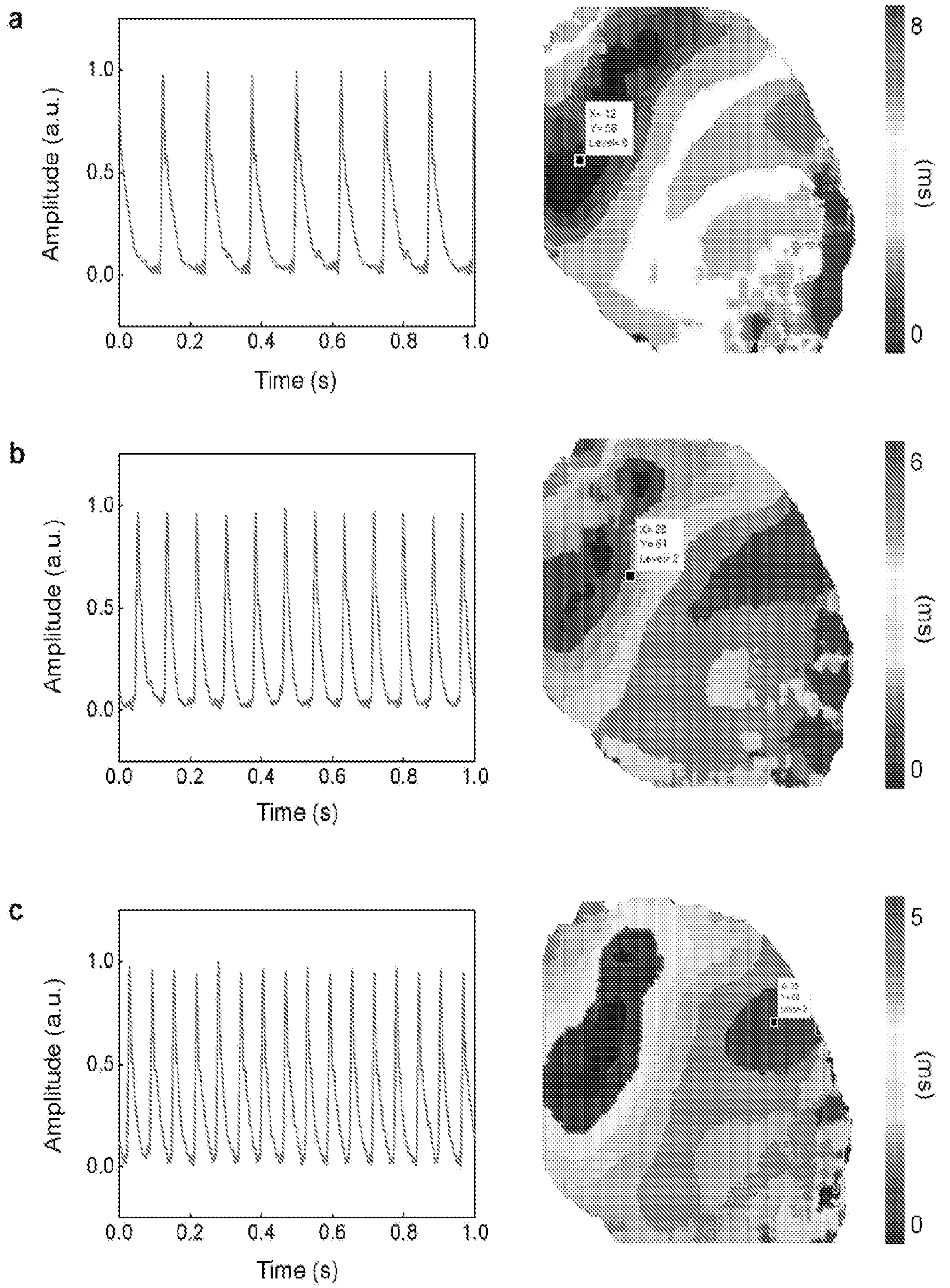
FIG. 15 shows ex vivo demonstration of bioresorbable, leadless cardiac pacemaker on mouse at different pacing frequencies, according to embodiments of the invention. Panels a, b, c: Representative optical action potential (left) and activation map (right) of a mouse heart during pacing with different pacing frequencies of 8, 12, and 16 Hz. Increasing the stimulation frequency maintains a 1 to 1 capture rate of stimulus to evoked action potential response with an appropriate increase in overall ventricular rate.

Images shown in panels a and d of FIG. 2 show the contact pads (electrode spacing ~2 mm) of devices placed onto the anterior myocardium of ex vivo Langendorff-perfused mouse and rabbit hearts, respectively. Activating the device by passing RF power (transmitting voltage=1 $V_{pp}$) through a nearby Tx antenna (12 mm diameter; 3 turns) generates cathodal impulses that are sufficient to initiate pacing. Far-field electrocardiography (ECG) recordings of the mouse (panel b of FIG. 2) and rabbit (panel e of FIG. 2) hearts show a transition from narrow QRS complexes to widened, high amplitude complexes that are consistent with ventricular capture by the pacemaker. Optical imaging yields action potential maps (panels c and f of FIG. 2) that show anisotropic activation of the membrane potential originating from the site of placement of the electrode pad that clearly propagates throughout the ventricular myocardium, as expected. FIG. 15 summarizes optical action potentials and activation map data obtained from pacing a mouse heart at different rates. The results indicate effective ventricular capture across a range of frequencies. Panel g of FIG. 2 shows a human ventricular heart slice (~400 μm thick) in a constant-flow, temperature-controlled perfusion system. The optical action potentials and activation maps in this case demonstrate successful pacing and activation of human cardiac tissue (panels h and i of FIG. 2). Taken together, these ex vivo tests indicate that this bioresorbable, leadless, battery-free cardiac pacemaker technology applies well across a range of sizes of mammalian cardiac tissues, including human hearts.

Figure 3:
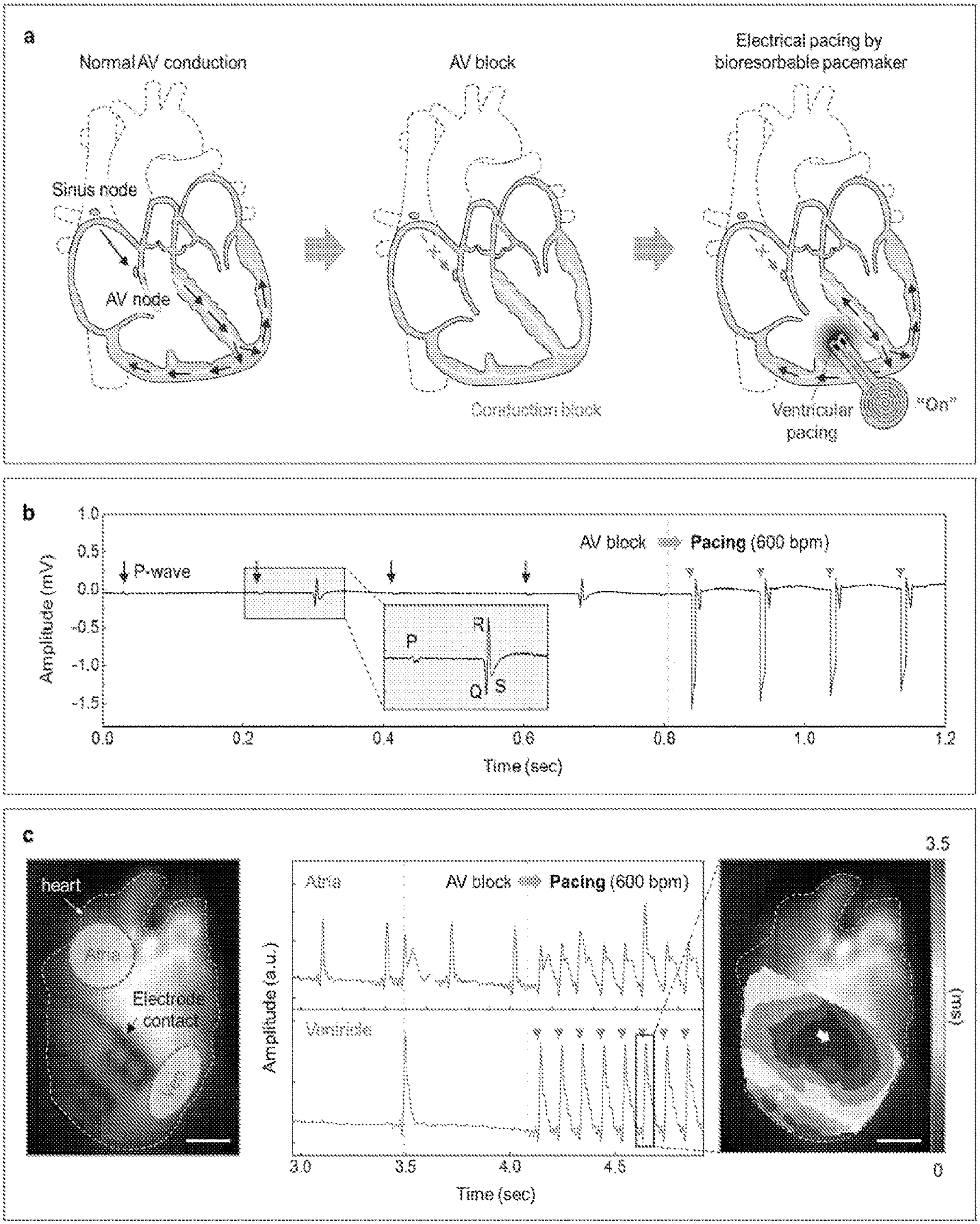
FIG. 3 shows treatment of AV block using a bioresorbable, leadless cardiac pacemaker in an ex vivo Langendorff-perfused mouse model, according to embodiments of the invention. Panel a: Schematic illustration of the nature of AV block and its treatment. In complete AV block, the conduction signal does not properly propagate from the atria to the ventricles. The pacemaker provides an electric impulse to restore activation of the ventricles. Panel b: Far-field ECG monitoring of a mouse heart with $2^{nd}$ degree AV block (white background). Ventricular capture via electrical stimulation using a bioresorbable device, as shown in the far-field ECG signal (yellow background; red arrows indicate delivered electrical stimuli). Magnified inset presents a representative P wave and QRS complex observed during $2^{nd}$ degree AV block. Panel c: (Left) Bright field image of mouse heart. The electrode of the bioresorbable pacemaker is positioned onto the anterior myocardial surface. Red and blue circles indicate the locations in the atria and ventricles, respectively, which correspond to the presented optical action potentials. (Middle) Simultaneous measurements of atrial and ventricular optical action potentials before (white background) stimulation show asynchronous activation between the atria and ventricles indicating $2^{nd}$ degree AV block. When electrical stimulation is delivered by the pacemaker (yellow background; red arrows indicate delivered electrical stimuli), the device restores activation of the ventricles. (Right) Activation map of the membrane potential during electrical stimulation by the device presents activation originating from the location of the contact pad as indicated by the white arrow. Scale bars, 2 mm.

Treating AV Block in an Ex Vivo Mouse Model. High-grade AV block corresponds to an interruption in the transmission of an impulse from the atria to the ventricles due to an anatomical or functional impairment in the conduction system. This intermittent or absent AV conduction can be transient or permanent. For the past 6 decades, electrical pacemakers have been critical for the treatment of patients with AV block. The bioresorbable, leadless cardiac pacemaker introduced here is an attractive potential alternative to conventional pacemakers for such patients, particularly if AV block appears transient. Panel a of FIG. 3 illustrates treatment of AV block with this type of device. The demonstration begins with ischemic reperfusion to induce second-degree AV block in an ex vivo Langedorff-perfused mouse heart. Healthy hearts exhibit a 1:1 association between the P wave (atrial depolarization) and QRS complex (ventricular depolarization). In the far-field ECG in panel b of FIG. 3, the first and third P waves are not followed by an associated QRS complex. This behavior is consistent with ventricular bradycardia arising from 2:1 conduction block between the atria and the ventricles (panel b of FIG. 3). Ventricular pacing using the bioresorbable pacemaker (transmitting voltage=1 $V_{pp}$; frequency=10 Hz) promptly generates widened, amplified QRS complexes at a normal mouse heart rate of 10 Hz (600 beats per minute (BPM)) in the ECG, which is consistent with effective ventricular pacing and prevention of bradycardia. Measurements of optical action potentials also confirm the efficacy for treatment of AV block. Panel c of FIG. 3 (left) shows the placement of the electrodes on the myocardial surface relative to the position of the atria and ventricles during optical recording. The results in panel c of FIG. 3 (middle) clearly show the conduction block between the atria and ventricles, with a 2:1 AV conduction. Electrical stimulation of the ventricles with the device restores ventricular activation that is critical for ventricular mechanical function and cardiac output. The activation map shows clear anisotropic activation originating from the contact electrode and propagation of the action potential throughout the entire ventricular myocardium (panel c of FIG. 3, right), consistent with the activation of the ventricles by the pacemaker.

Figure 16:
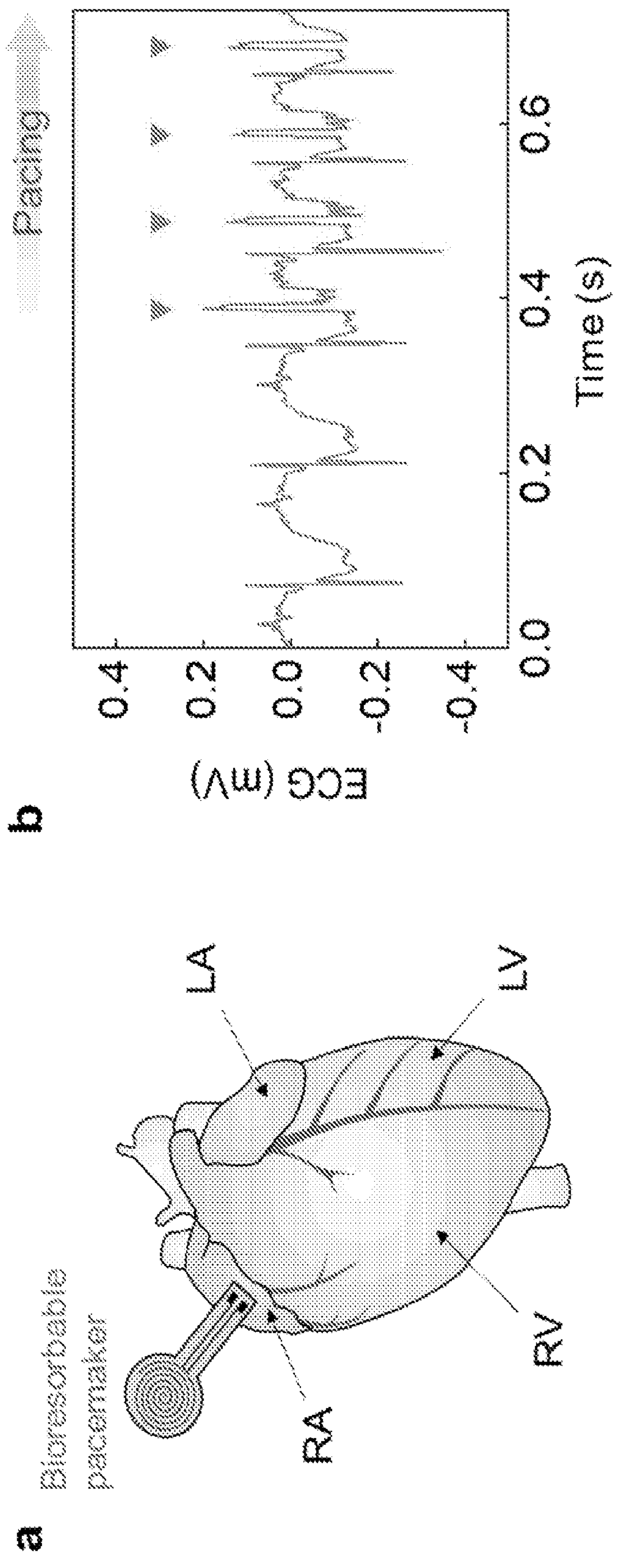
FIG. 16 shows in vivo demonstrations of atrial pacing by the bioresorbable cardiac pacemakers in a rat model, according to embodiments of the invention. Panel a: Schematic illustration of the rat's heart and position of the bioresorbable pacemaker. Panel b: ECG signals before (white background) and during electrical stimulation on right atrium (RA) (yellow background; red arrows indicate delivered electrical stimuli). n=3 biologically independent animals.

Placing the electrode on the right atrium (RA) near the sinoatrial (SA) node enables electrical stimulation of the atria in a mode that closely matches the physiological conduction system of the heart for native AV conduction. The schematic illustration in panel a of FIG. 16 shows the electrode pad of the bioresorbable pacemaker that attached to the RA. ECG signals before and after electrical stimulation confirm the capture of the P wave (panel b of FIG. 16). This result confirms that atrial pacing also can drive the rhythm of the heart for treatment of AV block.

Figure 4:
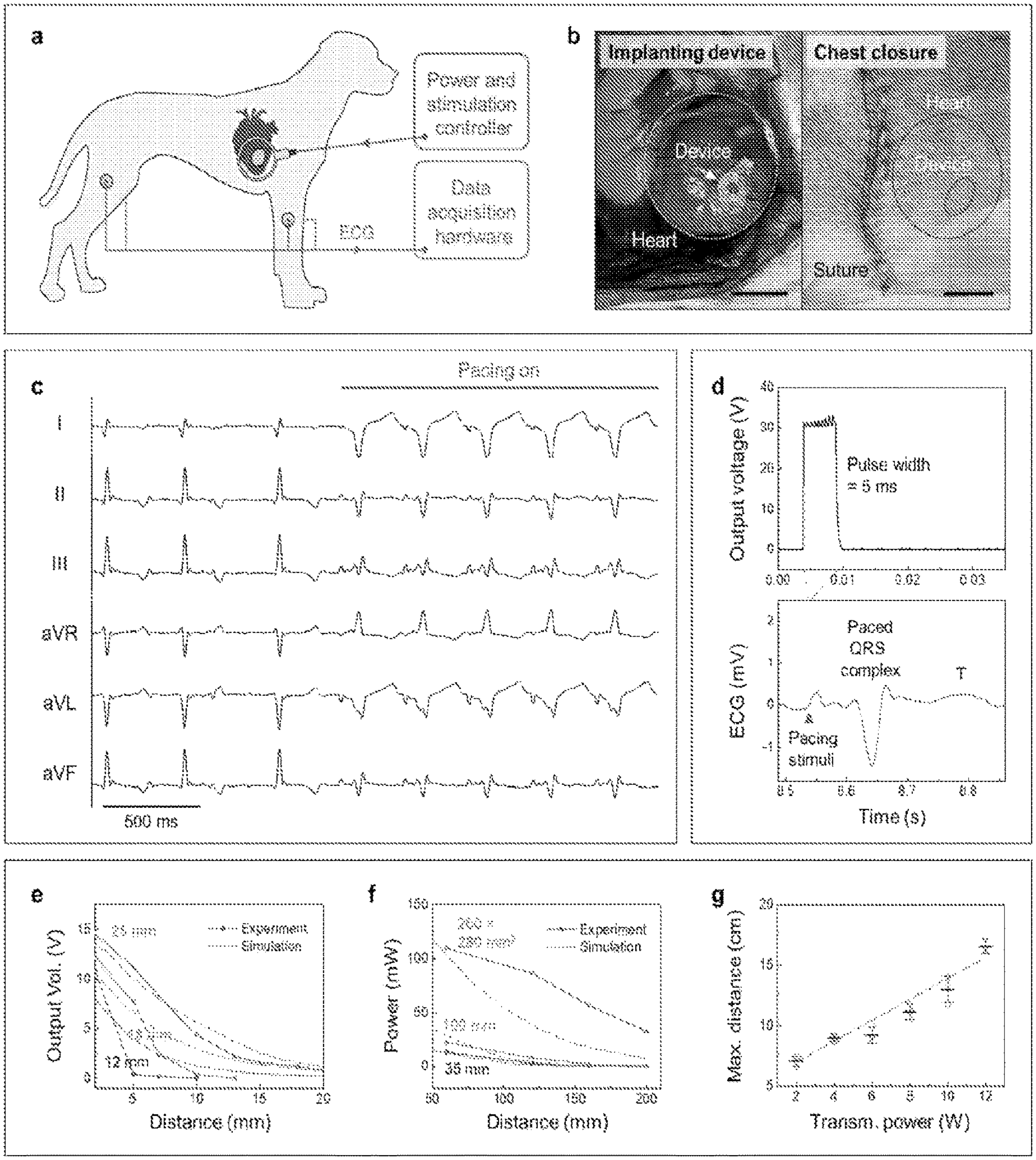
FIG. 4 shows demonstration of a bioresorbable, leadless cardiac pacemaker in an in vivo canine model, according to embodiments of the invention. Panel a: Schematic diagram of the setup for these tests. Panel a: Photographs of (panel a) an open chest procedure with the device sutured to the ventricular epicardium and (panel b) a sutured incision after chest closure. Scale bar, 5 cm. Panel c: 6-lead ECG recording of intrinsic rhythm (white background; ~120 bpm) and ventricular capture (yellow background; ~200 bpm) using the device. n=3 biologically independent animals per group. Panel d: Time dependence of the output voltage generated by the device (30 V; 5 ms) and corresponding ECG recordings from the dog's heart. Panel e: Output voltage as a function of the distance between the Rx and Tx coils (transmitting voltage=3.6 V). Three different colors indicate three different sizes of Rx coils: black, 12 mm; red, 18 mm; blue, 25 mm. Panel f: Output power as a function of the distance between the Rx and Tx coils (diameter of Rx coil=25 mm; input frequency=13.56 MHz; input power=12 W; load resistance=5000Ω). Three different colors indicate three different designs for the Tx coils: black (solenoid type; 4 turns; 35 mm diameter); red (solenoid type; 4 turns; 100 mm diameter); blue (square; 1 turn; 260×280 $mm^2$). Panel g: In vivo (canine model with fully closed chest) studies of the maximum pacing distance (i.e., the largest distance between the two coils that enables consistent ventricular capture) as a function of transmitted power (input frequency=13.56 MHz). The tests use Tx coils III (square; 1 turn; 260×280 $mm^2$) and an Rx coil with a diameter of 25 mm. n=3 biologically independent animals per condition. In panel g, the results are shown as means±s.e.m.

In Vivo Pacing in a Large Animal Model. In vivo studies with a canine whole heart model at a scale that recapitulates human physiology are of high relevance to the envisioned clinical implementation since the canine cardiovascular system bears high resemblance to that of a human. Here, in vivo testing in a canine model (adult hound dogs, female, 27-36 kg) during open chest surgery demonstrates the feasibility of this bioresorbable, leadless, battery-free pacemaker in a large animal. The illustration in panel a of FIG. 4 shows the setup. Electrical pulses generated using a power and stimulation controller, including a waveform generator and amplifier, pass through a Tx coil to the Rx coil of the device. A 6-lead ECG system with adhesive-backed electrodes on the limbs monitors cardiac activity throughout the period of the experiments. The photographs in panel b of FIG. 4 show the device sutured onto the myocardial surface of the right ventricle and the sutured incision after chest closure. Panel c of FIG. 4 presents ECG recordings of the intrinsic rhythm (white background; ~120 bpm) and ventricular capture (yellow background; 200 bpm) with clear pacing spikes and ventricular pacing morphologies of the QRS complex after placing the Tx coil in proximity to the Rx coil. Panel d of FIG. 4 shows the applied voltage (top) to the contact electrode (i.e., output voltage) and the corresponding ECG signal (bottom). Upon cathodal stimulation (output voltage=30 V; pulse width=5 ms; burst period=300 ms), capture occurs at the onset of the impulse (i.e., leading edge). Here, a widened, high amplitude QRS complex appears following the epicardial pacing stimulus, which indicates ventricular capture. A 50-60 ms latency exists between the ventricular pacing stimulus and the QRS complex, as well as a low amplitude delta wave at the onset of each QRS complex in panel c of FIG. 4. The latency indicates that it takes ~50 ms for epicardial excitation to cross the ventricular wall and engage the endocardial Purkinje system. The low amplitude delta wave is also due to epicardial pacing. A delta wave represents pre-excitation where the ventricles are excited earlier than expected in the normal cardiac conduction pathway. Because we are performing epicardial pacing at a rate that is faster than the intrinsic sinus rhythm, overdrive epicardial pacing causes a pre-excitation in the ventricles so that a delta wave inflection is seen at the onset of each QRS complex. Therefore, these observations of a 50-60 ms latency and a delta wave at the onset of each QRS complex confirm that the bioresorbable pacemaker successfully delivering epicardial stimuli for pacing in a large animal model.

Figure 17:
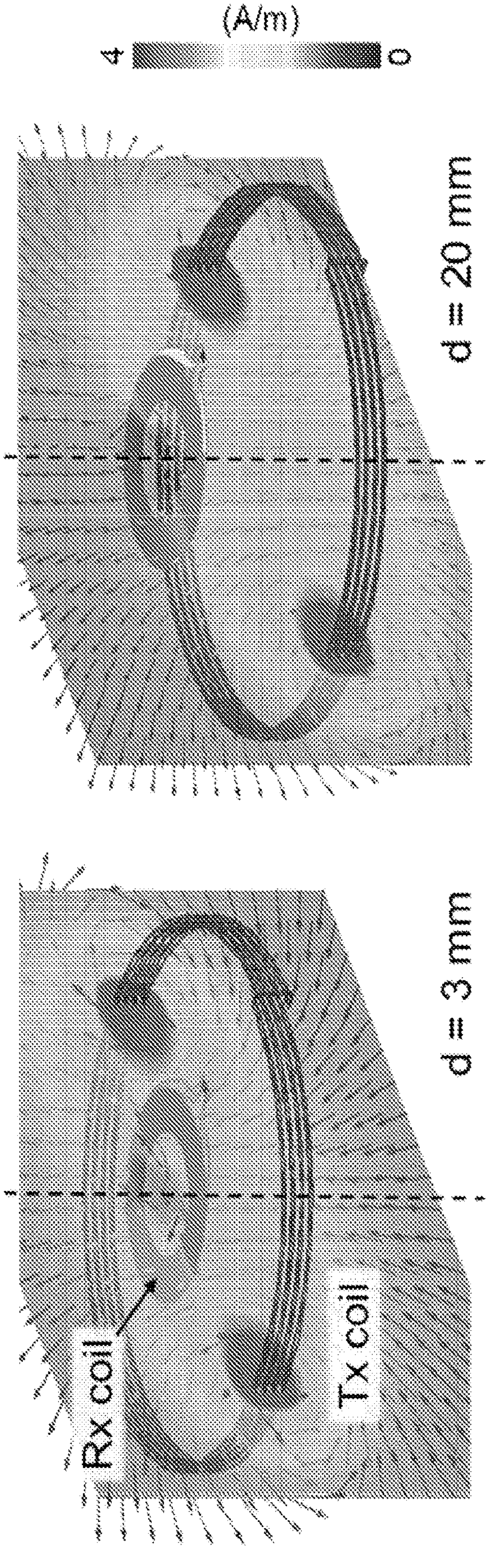
FIG. 17 shows long-range electromagnetic characteristics of bioresorbable, leadless cardiac pacemakers, according to embodiments of the invention. Simulated electromagnetic field distribution near the coupled Rx and Tx coils for a separation distance of (left) 3 mm and (right) 20 mm (transmitting power=1 W).

The power transfer for device operation depends on the mutual inductance between the Rx and Tx coils. This relationship is represented by $M=k\sqrt{L_{Tx}L_{Rx}}$, where the individual coil inductances are $L_{Rx}$ and $L_{Tx}$. The coupling coefficient k defines the linkage of the magnetic flux, and the value mainly depends on the distance and relative angle between the coils. Proper design choices ensure operation for average skin-to-heart distances in adult patients (parasternal 32.1±7.9 mm; apical 31.3±11.3 mm; subcostal 70.8±22.3 mm). FIG. 17 shows the magnetic field strength distribution for the coupling between a planar spiral Rx coil (25 mm diameter) and a 3D spiral Tx coil (64 mm diameter; 4 turns; Power=1 W). As the distance between the coils increases from 3 mm to 20 mm, the coupling coefficient decreases, which consequently lowers the strength of the magnetic field in the receiver coil to result in a reduced output voltage (panel g of FIG. 11). From Faraday's law of induction, the time rate of change of the magnetic flux through the Rx coil scales with its enclosed area to induce an output voltage. Thus, Rx coils with diameters smaller than 25 mm fail to meet the thresholds output voltage that required for pacing the canine heart at 20 mm (panel e of FIG. 4). The magnetic field strength increases with the square root of the transmitting power. The use of increased powers (2-12 W) and optimized (i.e., larger area and high coupling coefficient) Rx and Tx coil geometries increase the working distance to more than 200 mm, as demonstrated in in vitro tests summarized in panel f of FIG. 4 and FIG. 19. In vivo pacing tests in a canine model validate the long-range wireless energy transfer capability of the bioresorbable pacing system. Here, the maximum pacing distance (i.e., distance between skin and Tx coil) is 17 cm, excluding the distance between Rx coil and the skin (panel g of FIG. 4 and FIG. 20) (Details are in EXAMPLE 4). Continuous pacing experiments in a fully equipped operation room for cardiac surgeries also confirm the absence of interference effects with standard electronic equipment, either due to or originating from the wireless, bioresorbable pacing system (panel c of FIG. 20). The near field (~13.56 MHz) wireless energy transfer mechanisms lead to negligible changes in pacing signals during the continuous operation with skin-to-Tx coil distances of 10 cm. Overall, these in vivo tests suggest that the wireless power transfer system employed in the canine model can achieve the power transfer necessary for operation of bioresorbable pacemakers in human adult patients (Clinical case scenario are in EXAMPLE 5).

Figure 5:
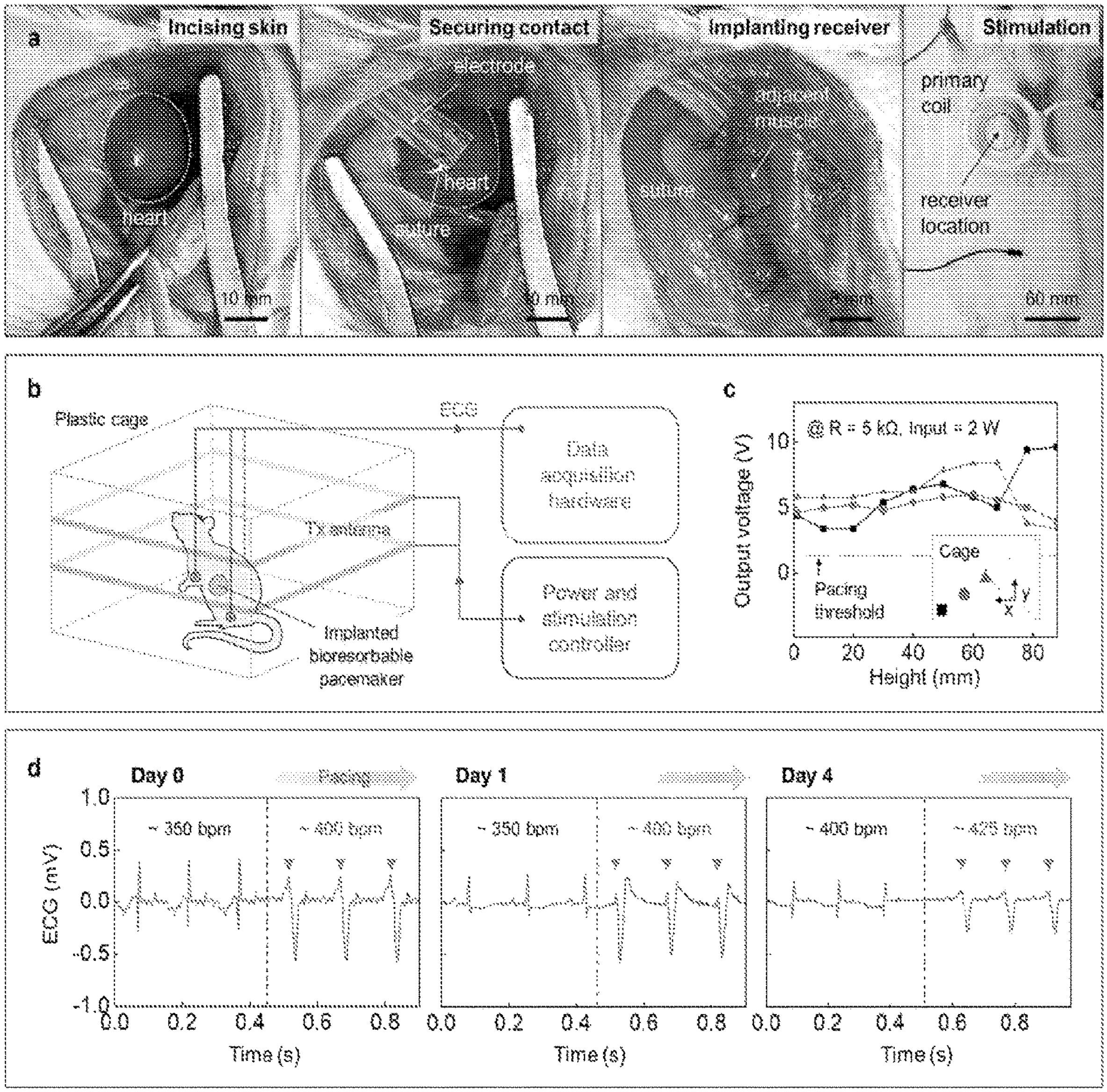
FIG. 5 shows implantation and operation of a bioresorbable, leadless cardiac pacemaker in a chronic in vivo rat model, according to embodiments of the invention. Panel a: Surgical procedure for implanting the device. The electrodes laminate onto the surface of cardiac tissue where they are sutured onto the anterior left ventricular myocardium. A small primary coil facilitates rapid testing of the functionality of the device. Panel b: Schematic diagram of a wireless pacing system setup that supports operation across a cage environment. Panel c: Spatially resolved wireless output voltage in a cage with an RF power of 2 W applied to the coils around the perimeter of the cage (load resistance=5 kΩ; input frequency=13.56 MHz). Output voltage of bioresorbable pacemaker exceeds a threshold of 1 V regardless of the height and position of the device. Panel d: ECG signals before (white background) and during electrical stimulation (yellow background; red arrows indicate delivered electrical stimuli) with the implanted bioresorbable cardiac pacemaker for 4 days. n=5 biologically independent animals.
Figure 22:
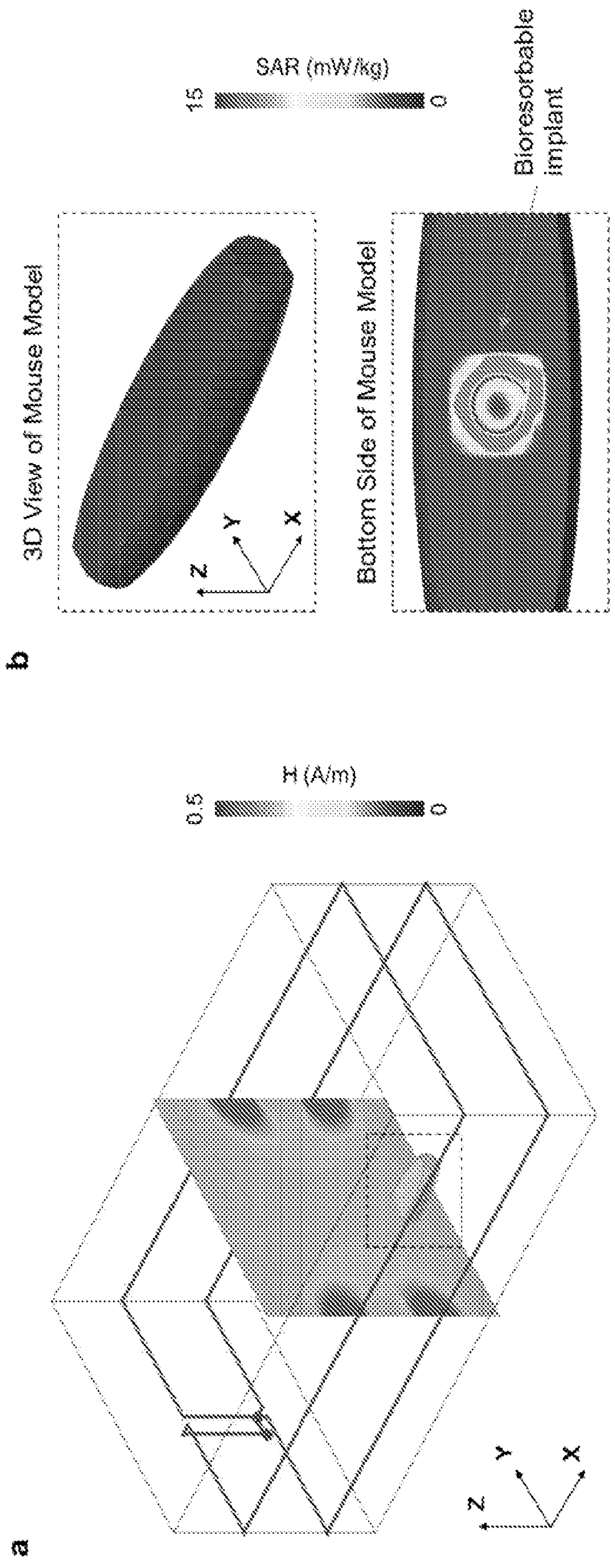
FIG. 22 shows results of simulation of the distribution of the electromagnetic field, according to embodiments of the invention. Panel a: Magnetic field distribution inside the cage at a cross sectional plane that intersects a simple model of a mouse. Panel b: Simulated specific absorption rate (SAR; a measure of the rate at which RF energy is absorbed by the body) as a function of position across a mesh model of a mouse body. (top) 3D and (bottom) 2D (x,y-axis) view of the mouse model.

Chronic Pacing Capability. Panel a of FIG. 5 summarizes the surgical procedures for implanting a bioresorbable, leadless pacemaker in a small animal (rat) model for chronic studies. Here, the pacemaker is inserted through an incision in the intercostal space to access the thoracic cavity and interface to the ventricles of the heart. The Rx part of the system remains in the subcutaneous space. The electrode pads laminate to the anterior myocardial surface of the left ventricle and are secured by a suture. Operation relies on a Tx antenna (12 mm diameter, 3 turns) that is applied and activated before and after closing the chest to confirm proper function and placement. Continuous, user-controlled operation is possible with an RF powering system (panel b of FIG. 5) and a large antenna that provides coverage throughout a location of interest (e.g., the home cage or testing arena) at field strengths that lie below IEEE and Federal Communications Commission (FCC) guidelines. Here, the RF system (i.e., power and stimulation controller) connects to two Tx loop antennas outfitted on the outer surface of a plastic cage to deliver power to the implanted bioresorbable cardiac pacemaker (FIG. 21). This RF setup with input power of 2 W (input frequency=13.56 MHz) provides output voltages that exceed the threshold for pacing (~1 V at load resistance of 5 kΩ) at any location (position and height) within the cage (panel c of FIG. 5). Under these conditions, the specific absorption rate (SAR; a measure of the rate at which RF energy is absorbed by the body) remains below safety guidelines (FIG. 22).

Figure 23:
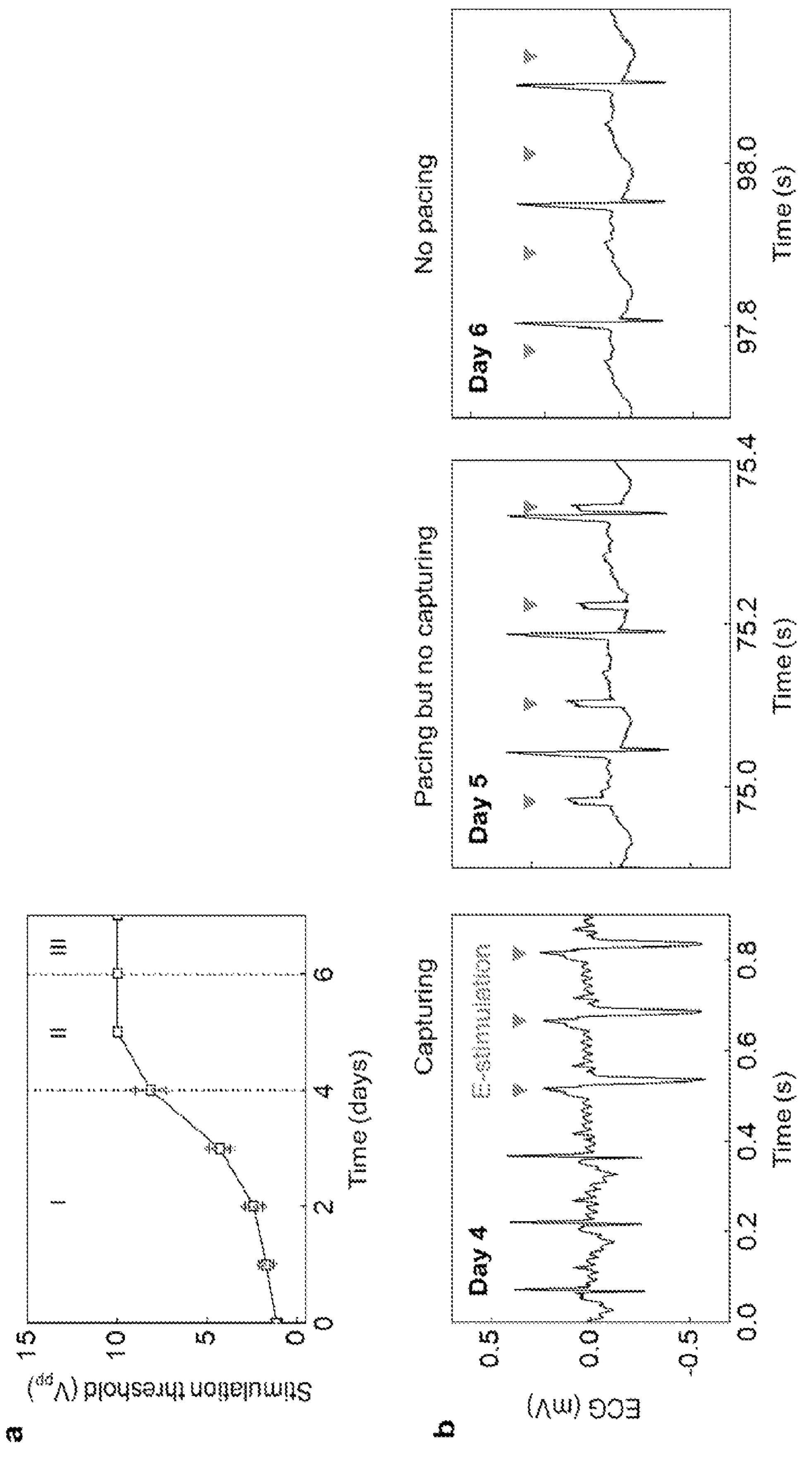
FIG. 23 shows changes in wireless pacing behavior during in vivo chronic tests in a rat model, according to embodiments of the invention. Panel a: Changes in stimulation threshold (i.e., minimum input voltage to Tx coil for pacing) as a function of time after implantation. Phase I, II, and III indicate the pacing behavior: capture, pacing but no capture, and no pacing, respectively. n=5 biologically independent animals. Panel b: ECG signals from rats with implanted bioresorbable cardiac pacemakers at 4, 5 and 6 days after device implantation. Red triangles indicate the timing of wireless electrical stimulation. n>10 biologically independent animals per group. In panel a, the results are shown as means±s.e.m.

Daily pacing trials occur on all animals while awake or under light sedation using optimized parameters (transmitting power ~6 W; pulse width=7 ms; heart rate=400-430 bpm). Data acquisition hardware monitors the ECG signal through subdermal needle electrodes positioned in the Lead I configuration (positive electrode on the right arm, negative electrode on the left arm, ground electrode on the leg). As before, pacing induces a transition of ECG signals from a narrow QRS complex, consistent with normal rate sinus rhythm (350-400 bpm), to a widened, amplified QRS complex with shortened R-R intervals, consistent with a paced rhythm (400-450 bpm). This change in ECG signal morphology indicates successful ventricular capture (panel d of FIG. 5, Day 0). Trials with programmable pacing parameters (transmitting voltage ~10 $V_{pp}$; pulse width=7 ms; heart rate=400-430 bpm) supports the capability for long-term in vivo pacing (panel d of FIG. 5). These studies rely on a small Tx antenna (12 mm diameter, 3 turns) to pace the animals during light sedation. The stimulation threshold (i.e., minimum transmitting voltage for pacing) increases from 1 $V_{pp}$ at a rate of 1-2 $V_{pp}$/day (panel a of FIG. 23). Successful operation of the device for pacing in this small animal model extends to post-operative day 4 (panel d of FIG. 5, Day 4). At day 5, the energy delivered by the device is strong enough to produce pacing spikes in the ECG but is insufficient to capture the ventricular myocardium (panel b of FIG. 23). At day 6, the device fails to pace the heart even at transmitting voltages >10 $V_{pp}$. The functional lifetime depends on the encapsulation materials and thicknesses, along with the overall device layout (Details are in EXAMPLE 6). These features can be adjusted to meet requirements specific to each clinical case.

Figure 6:
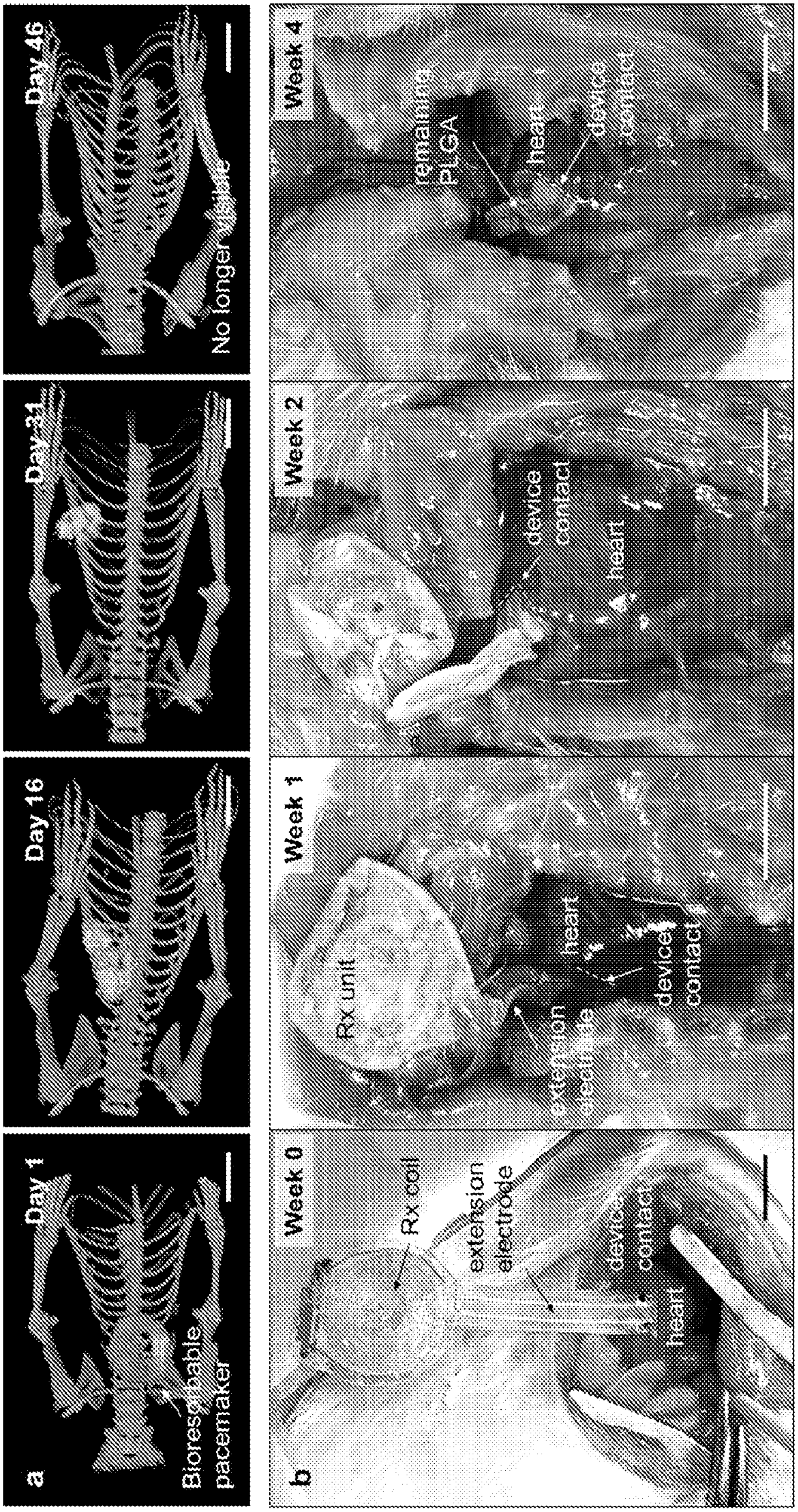
FIG. 6 shows bioresorbability studies of the leadless cardiac pacemaker, according to embodiments of the invention. Panel a: Three-dimensional-rendered computed tomography (CT) images of rats collected over 7 weeks after the implantation of bioresorbable cardiac pacemakers. The images indicate the gradual disappearance of the devices to the stage where they are no longer visible on day 46. Scale bar, 10 mm. n=3 biologically independent animals. Panel b: Images of devices implanted in a rat model, at different stages of bioresorption over the course of 4 weeks. The results reveal the mechanisms of bioresorption of the device after a therapeutic period. Scale bar, 5 mm. n=3 biologically independent animals.
Figure 26:
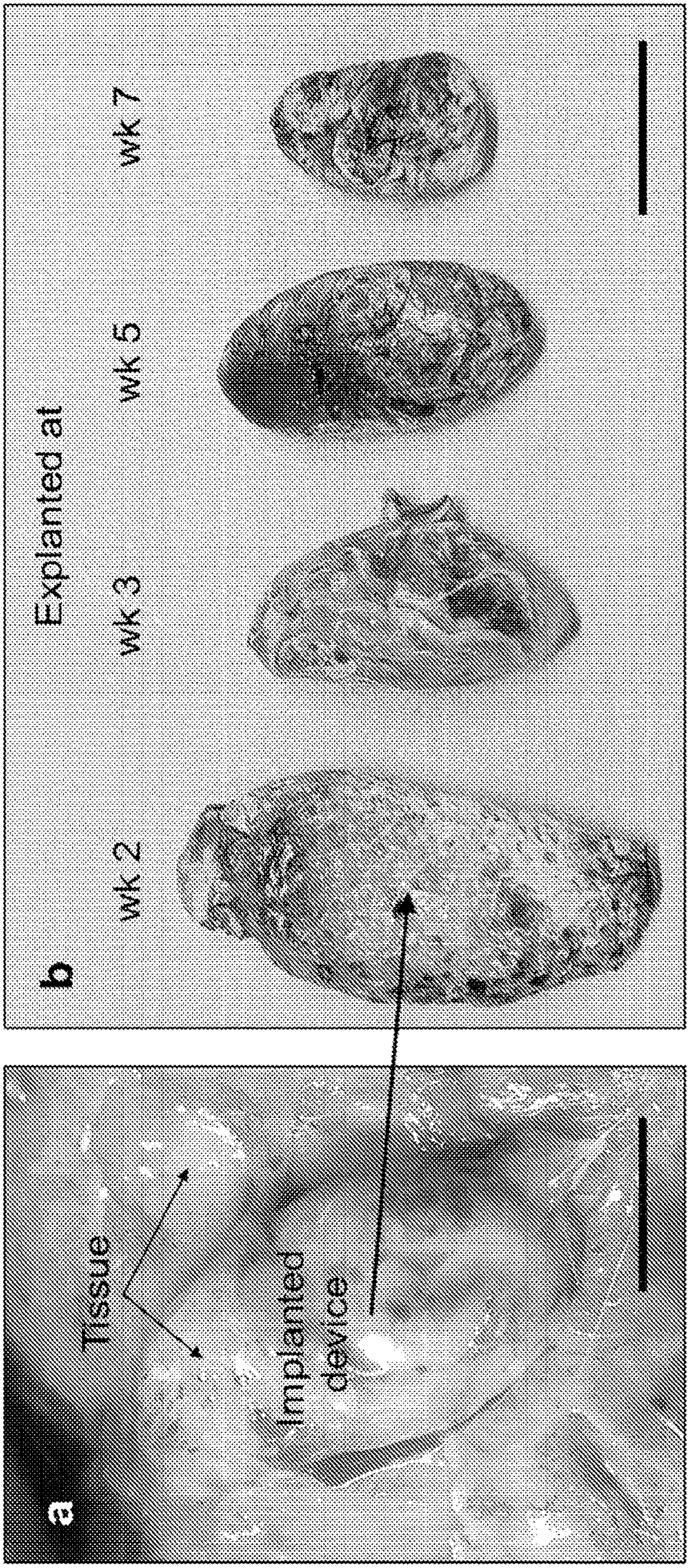
FIG. 26 shows in vivo studies of degradation of the bioresorbable, leadless cardiac pacemaker, according to embodiments of the invention. Panel a: Image of device after 2 weeks of implantation in a rat model. Scale bar, 10 mm. Panel b: Images of explanted devices at different stages of bioresorption over the course of 7 weeks. Scale bar, 10 mm.

In Vivo Bioresorbability and Biocompatibility of Bioresorbable, Implantable Pacemaker. Here, the processes of bioresorption can be monitored non-invasively and at high resolution using computed tomography (CT). Typically, the bioresorbable Mg features have low visibility in the CT image due to the low radiocontrast of Mg. However, an additional coating of high radiocontrast bioresorbable metal (W; ~700 nm thick) on the Mg (~50 μm thick) eliminates this limitation. Since the rate of dissolution of W is much smaller (96 nm/day) than that of Mg (7200 nm/day), this thin coating allows imaging over a timeframe similar to that of in vivo bioresorption of the device. Panel a of FIG. 6 presents the results of non-invasive monitoring of bioresorption, indicating the gradual disappearance of the device to its complete disappearance from the image on week 7. Panel b of FIG. 6 confirms these bioresorption processes in rats. At 1 week after implantation, the device maintains its shape, and the contact with the heart also remains intact. There is some reduction in size associated with resorption as seen in the image taken at 2 weeks, and the device maintains its connection to the heart. At 4 weeks, fibrotic tissue envelops the diminished Rx coil and extension electrode, and the device completely decouples from the heart. This fibrotic tissue limits diffusive access of biofluids to the surface of the bioresorbable materials, thereby decreasing the rates of chemical reactions that lead to bioresorption. Images of explanted devices at 1, 3, 5, and 7 weeks provide additional insights into the resorption of the implanted Rx coil over time (FIG. 26). The device largely dissolves within three weeks, and remaining residues completely disappear after twelve weeks. Overall, the structure of the pacemaker shrinks and collapses over time to resorb into the surrounding tissues and biofluids for self-elimination of the device.

Figure 7:
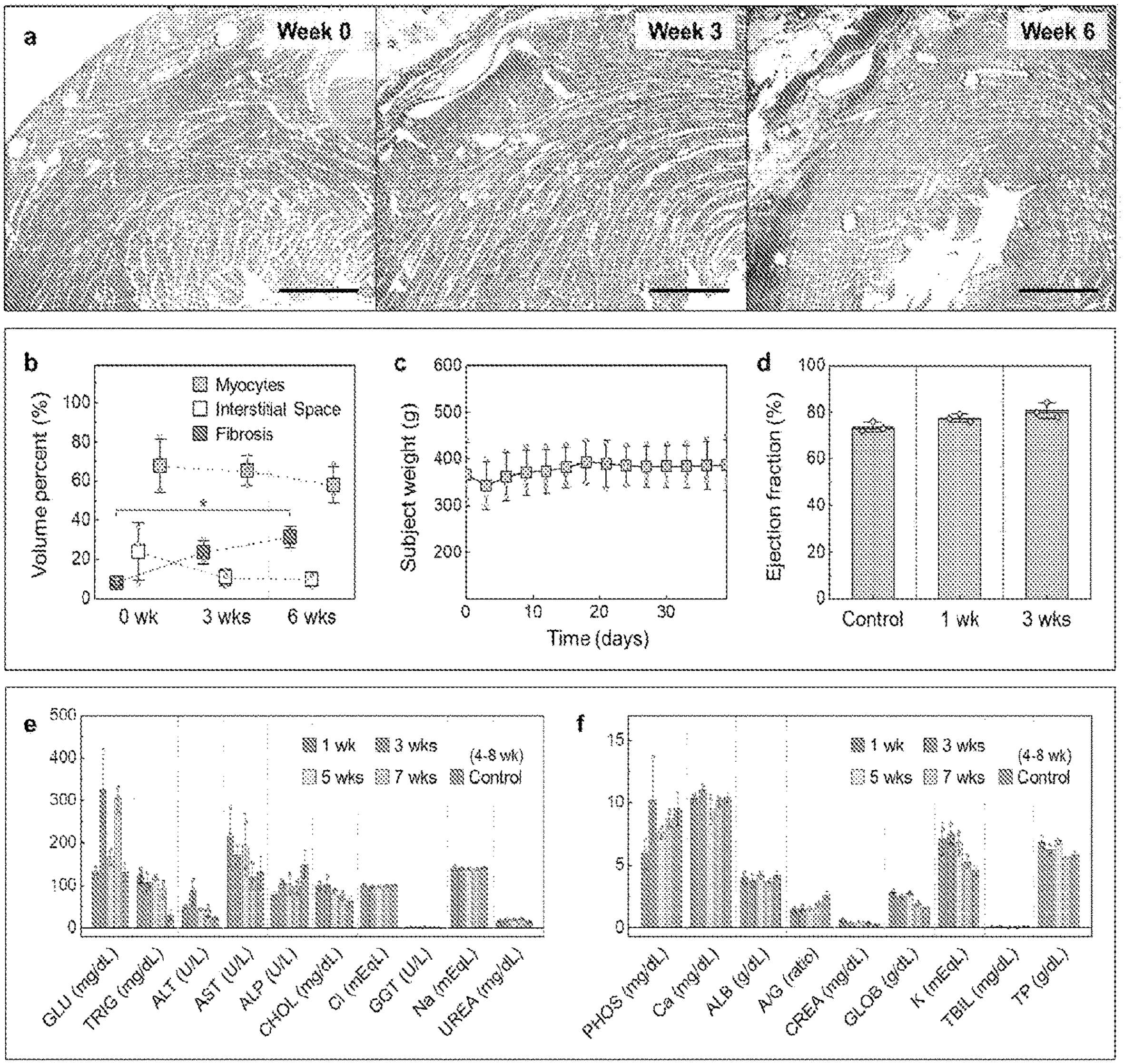
FIG. 7 shows biocompatibility and toxicity studies of bioresorbable, leadless cardiac pacemaker, according to embodiments of the invention. Panel a: Representative image of Masson's trichrome stain of the cross-sectional area of the anterior left ventricle of a rat (left) without (0 weeks) and with an implanted device after (middle) 3 weeks and (right) 6 weeks near the site of implantation. Scale bar, 1 mm. Panel b: Percent volume of myocytes (pink), interstitial space (white), and fibrosis (blue) in the transmural cardiac cross-section of rats without implants, 3 weeks following implantation, and 6 weeks following implantation (*$p<0.05$). n=3 biologically independent animals per group. Panel c: Weights of the animals measured every 3 days following surgery show initial decrease as anticipated after a major surgery but increase appropriately with age as expected in healthy animals. n=3-6 biologically independent animals per group. Panel d: No significant changes in ejection fraction in rats before device implantation (control) and 1 and 3 weeks after implantation demonstrates preservation of mechanical cardiac function (paired data; *$p<0.05$). n=3 biologically independent animals per group. Panels e, f: Analysis of complete blood counts and blood chemistry for rats with and without implantation of bioresorbable pacemaker reveals maintenance of overall healthy physiology in the animals. n=3 biologically independent animals. Control data were provided by Charles River Laboratories. GLU, glucose (mg $dL^{-1}$); TRIG, triglycerides (mg $dL^{-1}$); ALT, alanine aminotransferase (U $L^{-1}$); AST, aspartate transaminase (U $L^{-1}$), ALP, alkaline phosphatase (U $L^{-1}$); CHOL, cholesterol (mg $dL^{-1}$); Cl, chloride (mEqL); GGT, gamma-glutamyl transferase (U $L^{-1}$); Na, sodium (mEqL); UREA, urea (mg $dL^{-1}$); PHOS, phosphorus (mg $dL^{-1}$); Ca, calcium (mg $dL^{-1}$); ALB, albumin (g $dL^{-1}$); A/G, albumin/globulin ratio; CREA, creatinine (mg $dL^{-1}$); GLOB, globulin (g $dL^{-1}$); K, potassium (mEqL); TBIL, total bilirubin (mg $dL^{-1}$); TP, total protein (g $dL^{-1}$). In panels b, c, d, e, and f, the results are shown with error bars as means±S.D.
Figure 8:
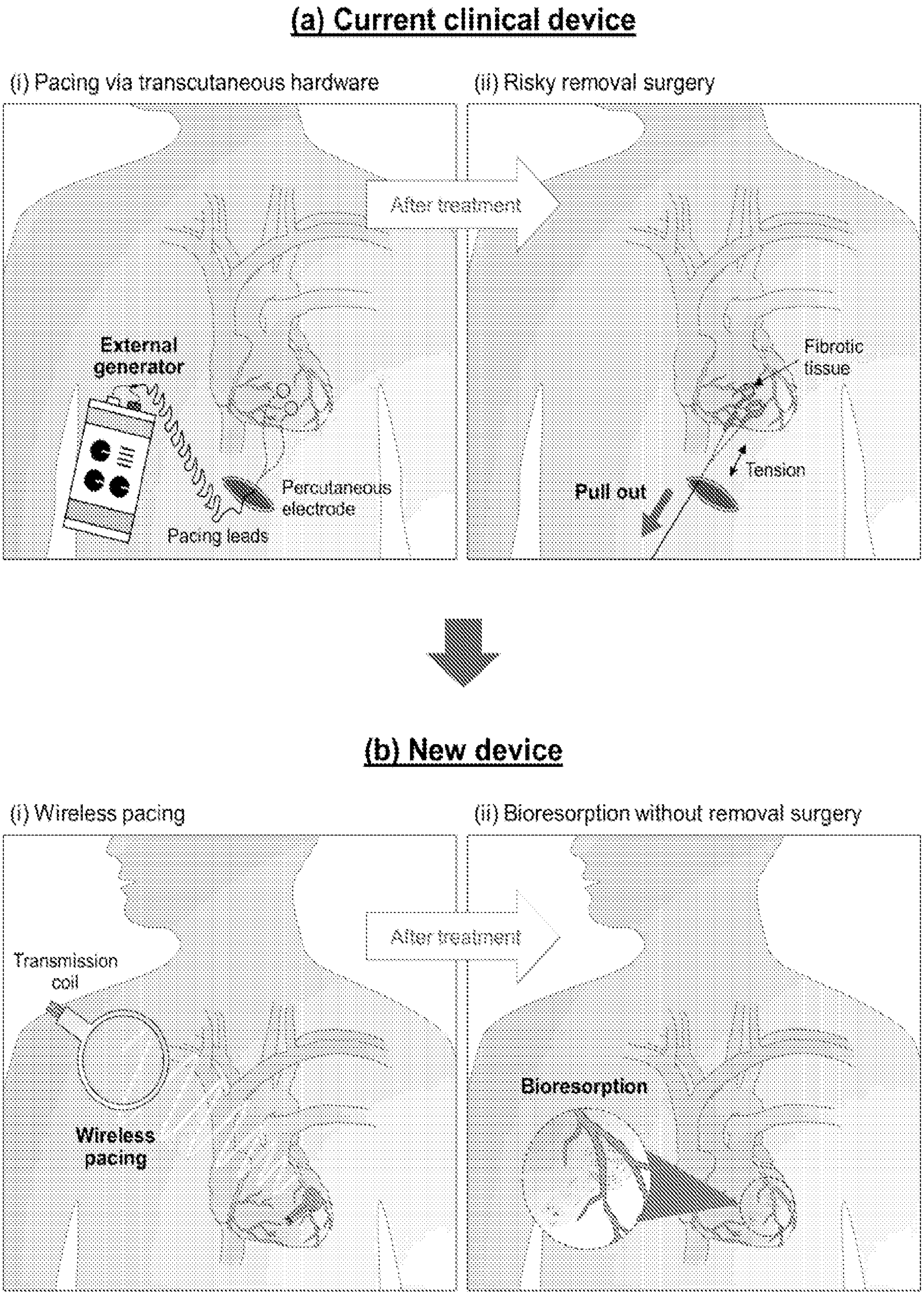
FIG. 8 shows illustrations that compare use scenarios of conventional temporary pacemakers and the bioresorbable, implantable, leadless, battery-free devices reported here, according to embodiments of the invention. Panel a: Schematic illustration that demonstrates the existing clinical approach for using conventional temporary pacemakers. (i) An external generator connects through wired, percutaneous interfaces to pacing electrodes attached to the myocardium. Temporary transvenous leads are affixed to the myocardium either passively with tines or actively with extendable/retractable screws. (ii) The pacing leads can become enveloped in fibrotic tissue at the electrode-myocardium interface, which increases the risk of myocardial damage and perforation during lead removal. As a result, temporary epicardial leads placed at the time of open heart surgery are often cut and allowed to retract to avoid the risk of removal by traction. Panel b: The proposed approach is uniquely enabled by the bioresorbable, leadless device introduced here. (i) Electrical stimulation paces the heart via inductive wireless power transfer, as needed throughout the post-operative period. (ii) Following resolution of pacing needs or insertion of a permanent device, the implanted device dissolves into the body, thereby eliminating the need for extraction.
Figure 27:
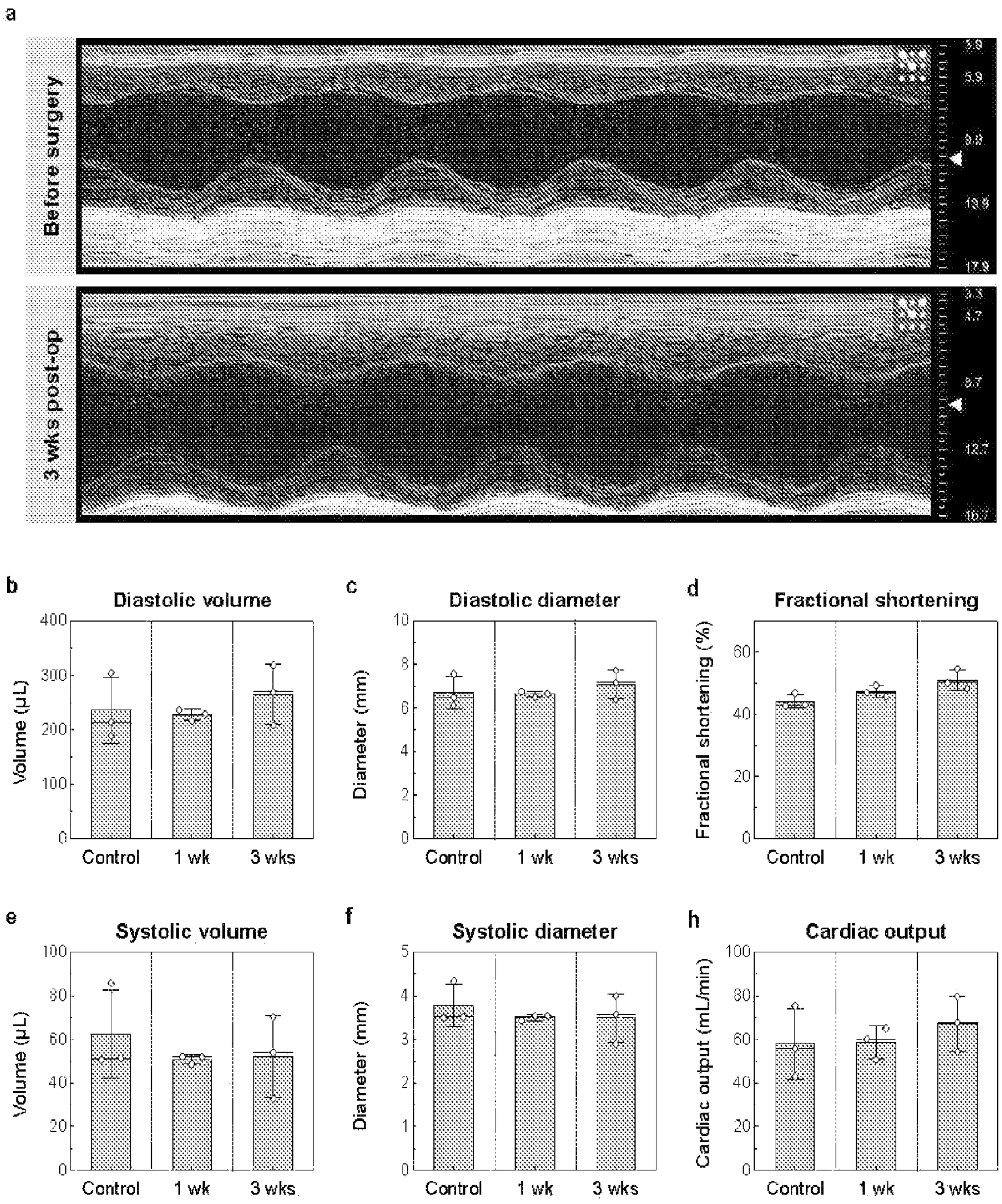
FIG. 27 shows echocardiographic assessment of animals following pacemaker implantation, according to embodiments of the invention. Panel a: M-mode echocardiogram (top) before and (bottom) after surgery. Panels b-h: No significant changes in diastolic volume, diastolic diameter, fractional shortening, systolic volume, systolic diameter, or cardiac output when compared before or at 1 or 3 weeks following operation (paired data; $*p<0.05$). n=3 biologically independent animals. These measurements show that implementation of the device does not impair the mechanical function of the heart.
Figure 28:
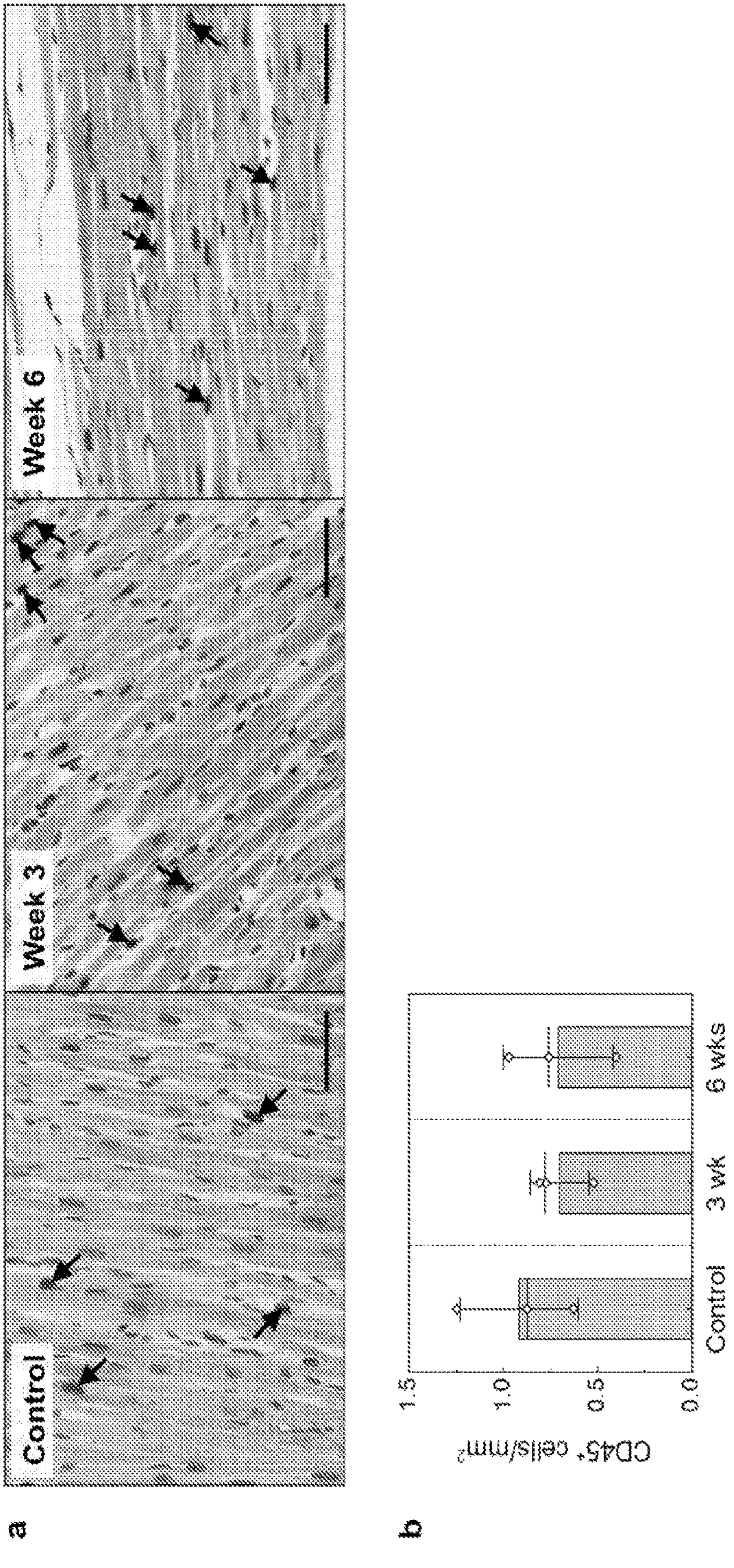
FIG. 28 shows inflammatory response of myocardium following pacemaker implantation, according to embodiments of the invention. Panel a: Representative images of the stained cross-sectional area of the left ventricle of a rat without (control) and with an implanted device after 3 weeks and 6 weeks near the site of implantation. Arrowheads indicate $CD45^+$ cells. Scale bar, 50 μm. Panel b: Frequency of $CD45^+$ cells in the ventricular myocardium near the site of implantation. No significant difference in $CD45^+$ cells in the myocardium following pacemaker implantation ($*p<0.05$). n=3 biologically independent animals per group.

Histological examination of the myocardial tissue near the site of pacemaker attachment up to 6 weeks after implantation supports the biocompatibility of the device, its constituent materials, and the products of their dissolution. At the 0, 3, and 6-week endpoints after implantation, histological analysis using Masson's trichrome staining quantifies the volume of myocardium, fibrotic tissue, and interstitial space in the transmural ventricular tissue near the site of device attachment (panel a of FIG. 7). Images of stained cross-sections reveal normal cardiac tissue structure with fibrosis restricted to the outer boundaries of the epicardium. Quantitative analysis reveals no significant changes in the composition of the myocardial wall 3 weeks following implantation (*$p<0.05$) (panel b of FIG. 7). Tracking of the weights of the animals following implantation (panel c of FIG. 7) shows significant reductions immediately post-operatively, as anticipated for any major surgery. Subsequently, weights normalized to pre-operative values and gradually increased with time, also as expected. These results, taken together with previously reported findings, provide strong evidence of the biocompatibility of the system. Echocardiograms provide real-time, dynamic outlines of the walls of the heart for measurement of myocardial morphology and various hemodynamic parameters. Echocardiograms collected at 0, 1, and 3 weeks after device implantation show no evidence of differences in ejection fraction (panel d of FIG. 7) or other hemodynamic parameters (diastolic volume, diastolic diameter, fractional shortening, systolic volume, systolic diameter, cardiac output) (FIG. 27) between these time points. The results indicate that the implanted device negligibly affect the native mechanical function of the heart. To assess the level of inflammation in the heart following the open-chest surgery and pacemaker implantation, we employed immunohistochemistry to visualize immunoreactivity of pan-leukocyte marker CD45 in the myocardium at the 0 (control), 3, and 6-week endpoints (FIG. 28). The quantification of CD45 immunoreactivity in the transmural ventricular tissue near the site of device attachment shows no significant difference in the frequency of $CD45^+$ cells after pacemaker implantation, which indicates that the pacemaker and the associated implantation surgery do not provoke a significant inflammatory response. The results of serology tests provide a comprehensive understanding of the health status of rats with implanted pacemakers as the devices resorb (panels e-f of FIG. 7). Blood levels of enzymes and electrolytes, as indicators of organ-specific diseases, fall within confidence intervals of control values. Specifically, normal levels of alanine aminotransferase, cholesterol and triglyceride, phosphorus and urea nitrogen, calcium, albumin, and total proteins indicate the absence of disorders in the liver, heart, kidney, bone and nerve, and good overall health, respectively. Taken together, these histology, echocardiography, immunohistochemistry, and serology results illustrate that the implantation and resorption of the novel bioresorbable pacemaker do not impact the natural physiology of the body system.

The exemplary example reported here introduce a bioresorbable, leadless class of temporary cardiac pacemakers and demonstrate its efficacy in a comprehensive series of small and large animal models. The material compositions and design choices of the device support the electrical performance characteristics necessary for temporary cardiac pacing applications in a thin, flexible platform and offer timescales for stable operation and complete bioresorption that can be tailored to specific therapeutic timelines. This miniaturized device receives power and control commands through wireless inductive power transfer. This scheme circumvents the need for batteries and their associated mass, physical bulk, and hazardous constituent materials. These fully implanted devices also minimize complications associated with infections by eliminating any percutaneous hardware and bypass requirements for secondary device removal by self-elimination through bioresorption. Although the application evaluated in this series of experiments primarily addresses the need for temporary leadless epicardial pacing, future versions have the potential for transvenous applications of temporary, leadless pacing in patients with AV block due to myocarditis or anti-tachycardia pacing in patients with AF associated with cardiac surgery. Promising directions for future research also include multisite pacing using different RF frequencies, introducing stimuli-responsive materials for active control of process of degradation, and coupling with sensors for closed-loop operation.

Example 2

Low Frequency PIN Diode for Capacitor-Free Design

Figure 12:
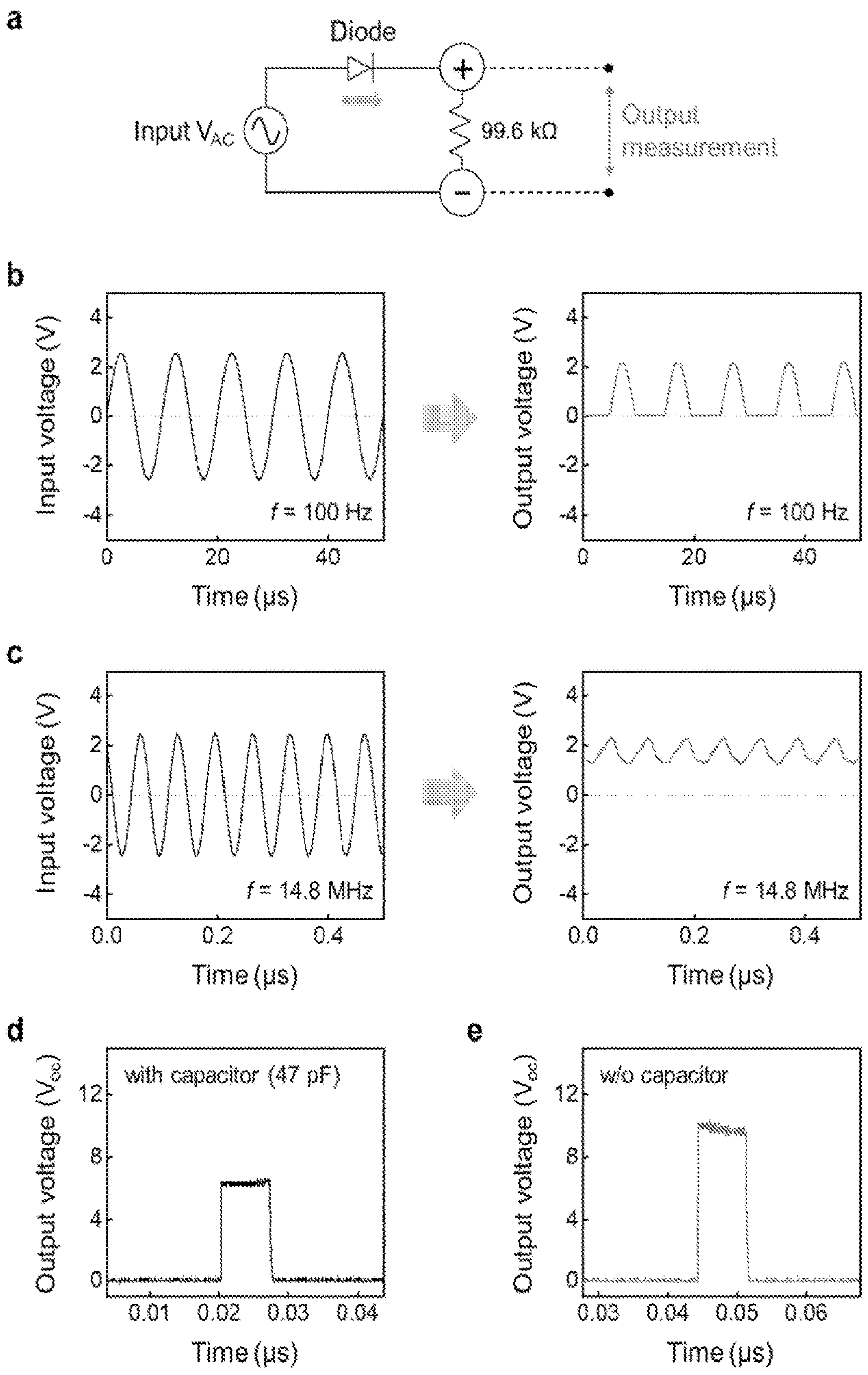
FIG. 12 shows input frequency dependent behavior of a bioresorbable diode, according to embodiments of the invention. Panel a: Schematic illustration of the circuit diagram for the characterization of the bioresorbable diode. Load resistance, 99.6 kΩ. Panel b: Low frequency signal rectification performance of the bioresorbable diode: (left) input AC signal with frequency of 100 Hz; (right) rectified AC-like half-cycle signal. Panel c: High frequency signal rectification performance of the bioresorbable diode: (left) input AC signal with frequency of 14.8 MHz; (right) rectified DC-like signal. Panel d: Pulse output signal (open circuit voltage, $V_{oc}$) from the bioresorbable cardiac pacemaker with bioresorbable a capacitor (47 pF) (input voltage=2 $V_{pp}$; input frequency=6.1 MHz; frequency=400 BPM; pulse width=7 ms). Panel e: Pulse output signal ($V_{oc}$) from the bioresorbable cardiac pacemaker without capacitor (input voltage=2 $V_{pp}$; input frequency=13.5 MHz frequency=400 BPM; pulse width=7 ms).

In the exemplary example, a bioresorbable low-frequency PIN diode with high parasitic capacitance yields a capacitor-free bioresorbable electrical stimulator with enhanced output performance. With the PIN structured diode in reverse bias, charge accumulates at the PI and IN junctions, thereby creating a diode capacitance ($C_t$) where the I region acts as a parasitic capacitor with capacitance proportional to the area (A) and inversely proportional to the distance (d). When forward biased, the PIN diode acts as a variable resistor. Switching between reverse and forward bias at timescales much larger than the carriers' lifetime leads to the typical behavior of a diode. However, the diodes have a reverse-recovery time, corresponding to a time for changing its response to a forward-biased from a reverse-biased state. Such switching results in some current flow in the reverse direction, and the reverse-recovery time is proportional to the size of $C_t$. Based on this mechanism, the bioresorbable PIN diode can be designed with a reverse-recovery time of the order of microseconds. At high-frequency (>1 MHz), the diode cannot fully recover during switching, thereby yielding DC-like output (with ripples) without the need for a smoothing capacitor. To illustrate the electrical characteristics of capacitor-free device with low-frequency PIN diode, we implemented the circuit shown in panel a of FIG. 12. At low input frequency (100 Hz), the voltage at the load resistor shows a typical AC-like half-cycle signal (panel b of FIG. 12) representative of a half-wave rectifier. However, at high input frequency (14.8 MHz), the output voltage at the load shows a low amplitude AC-signal on a DC offset (panel c of FIG. 12). The transition from an AC-like half-cycle to DC-like ripples occurs at around 1 MHz input frequency. The device with a bioresorbable capacitor (47 pF) shows an open circuit voltage ($V_{oc}$) of ~6 V at a resonance frequency of 6.1 MHz (panel d of FIG. 12), while capacitor-free device shows $V_{oc}$ of ~10 V at a resonance frequency of 13.5 MHz (panel e of FIG. 12). This result indicates that the capacitor-free device supports improved performance since the output voltage ($V_0$) is as follows:

$$V_o = 2\pi fNSQB_o\cos\alpha$$

where f is the frequency of the input signal, N is the number of turns of coil in the loop, S is the area of the loop, Q is the quality factor of circuit, $B_O$ is the strength of the input signal, and α is the angle of arrival of the signal. In addition, eliminating the capacitor component, simplifying the fabrication process, and reducing the number of interconnections further improves the yields and mechanical reliability of the device.

Example 3

Electrode Spacing Optimization Using a Cable Model

Figure 14:
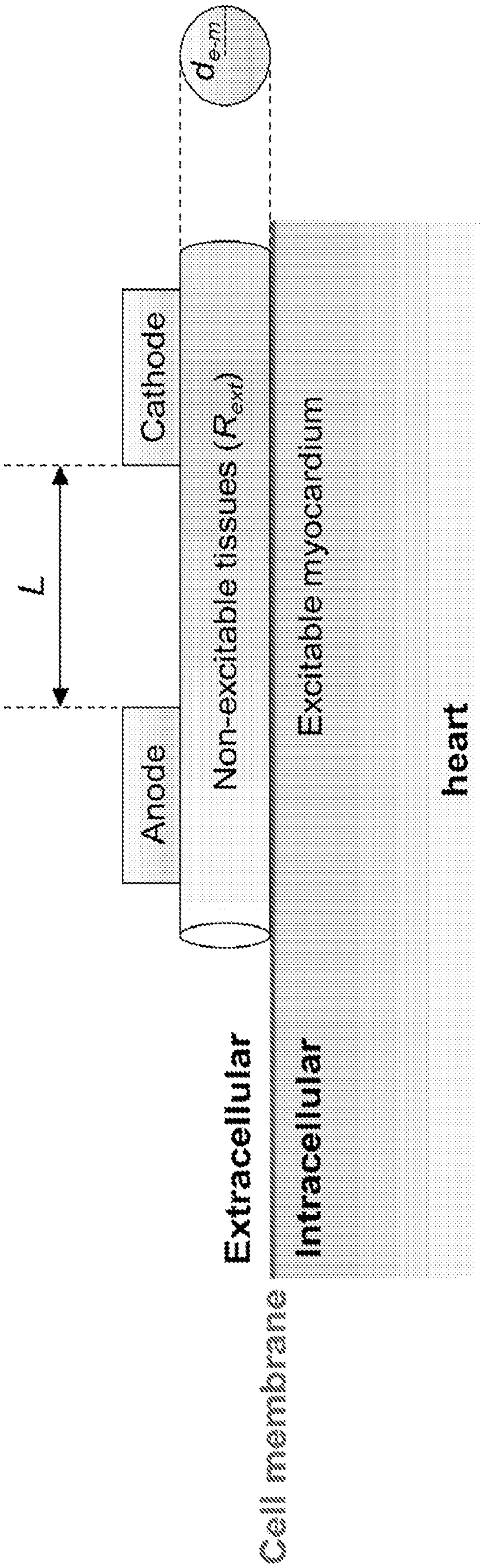
FIG. 14 shows cable model of the process for stimulating excitable cells, according to embodiments of the invention. The cable model approximates a strip of cardiac tissue as a cable composed of resistors and capacitors to match specific electrical properties of the myocardium. The extracellular space that surrounds the excitable myocytes can be modeled as a cylinder with diameter $d_{e-m}$ and a resistance of $R_{ext}$. The potential difference of the interelectrode extracellular fluid is the minimum voltage that must be applied in order to capture the heart. Employment of this model determines the optimal distance (L) between contact electrodes for capture of the heart rhythm with minimum voltage input.

The one-dimensional cable theory is a useful mathematical model where a "cable" with specific electrical properties approximates the dynamics of a "strip" of myocardium. Using the cable theory model, we can garner some qualitative insights into the optimal electrode design for electrode-induced myocardial excitation. According to cable theory, we can model the extracellular space around the myocyte as a cylinder of radius of $d_{e-m}$, or the distance between the electrode and the excitable myocardium (FIG. 14). Only a small portion of the electric current applied at the electrodes passes through to the cell membrane and into the cell, and the magnitude of the transmembrane current flow depends on the relative resistance of the intracellular and extracellular fluids. Here, the extracellular resistance ($R_{ext}$) can be defined as follows:

$$R_{ext} = \frac{1}{\pi d_{e-m}^2 G_{out}}$$

where $G_{out}$ is the extracellular fluid conductivity. The inter-electrode extracellular fluid potential difference ($\Delta\Psi_{out}$) is also the minimum voltage that must be applied across the electrodes to achieve myocardial capture which can be expressed by $$\Delta\Psi_{out} = I_0 R_{ext} L = \frac{I_0 L}{\pi d_{e-m}^2 G_{out}} \Rightarrow L = \frac{\Delta\Psi_{out}\pi d_{e-m}^2 G_{out}}{I_0}$$

where $I_0$ is the threshold current and L is the interelectrode distance. For the same minimum input voltage for pacing ($\Delta\Psi_{out}$) where $G_{out}$ and $I_0$ are relatively constant across scenarios, this equation suggests that the interelectrode distance (L) primarily depends the distance between the electrode and excitable myocardium ($d_{e-m}$). Since animals with larger hearts have a greater $d_{e-m}$ as evidenced by a greater tissue impedance, a greater L is required for large animals compared to small animals. Based on this approximation, we tune the electrode spacing between 1 mm to 5 mm depending on the size of the hearts.

Example 4

Device Design Optimization for Long-Range Wireless Operation

Figure 18:
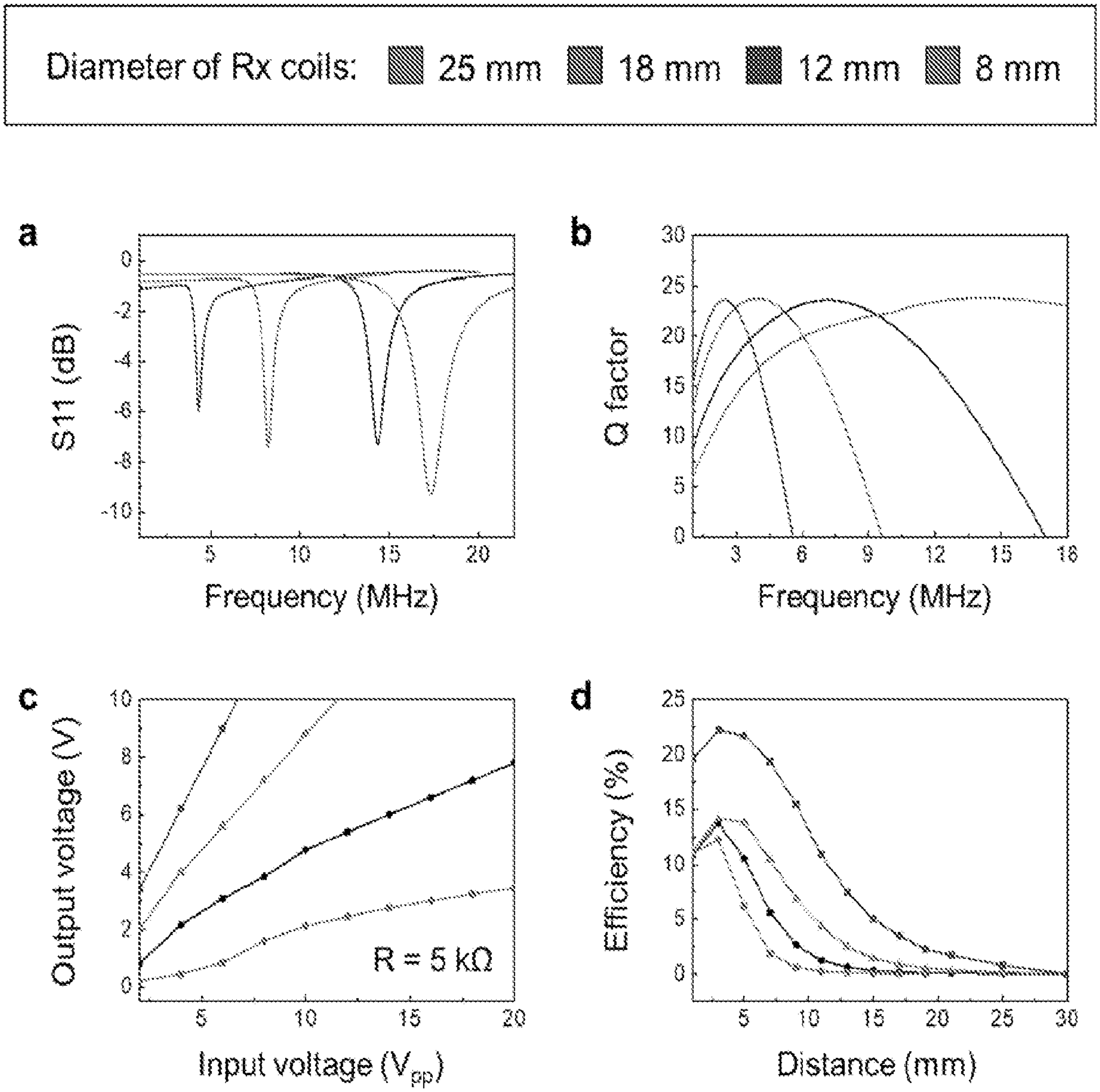
FIG. 18 shows electromagnetic characteristics of bioresorbable, leadless cardiac pacemakers with various sizes of wireless power harvesting units, according to embodiments of the invention. The sizes of the Rx coils are 25 (blue), 18 (red), 12 (black), and 8 mm (green). Panel a: Simulated scattering parameters (S11) of the wireless power harvesting units with different sizes of receiver coils. The resonance frequency of each coil is 4.24, 8.03, 13.91, 17.33 MHz, respectively. Panel b: Simulated Q factors of the wireless power harvesting units, respectively. Panel c: Experimental results for the output voltage as a function of input voltage at a coil-to-coil distance of ~1 mm and load resistance of 5 kΩ. Panel d: Simulated power transfer efficiency as a function of changes in coil-to-coil distance.
Figure 19:
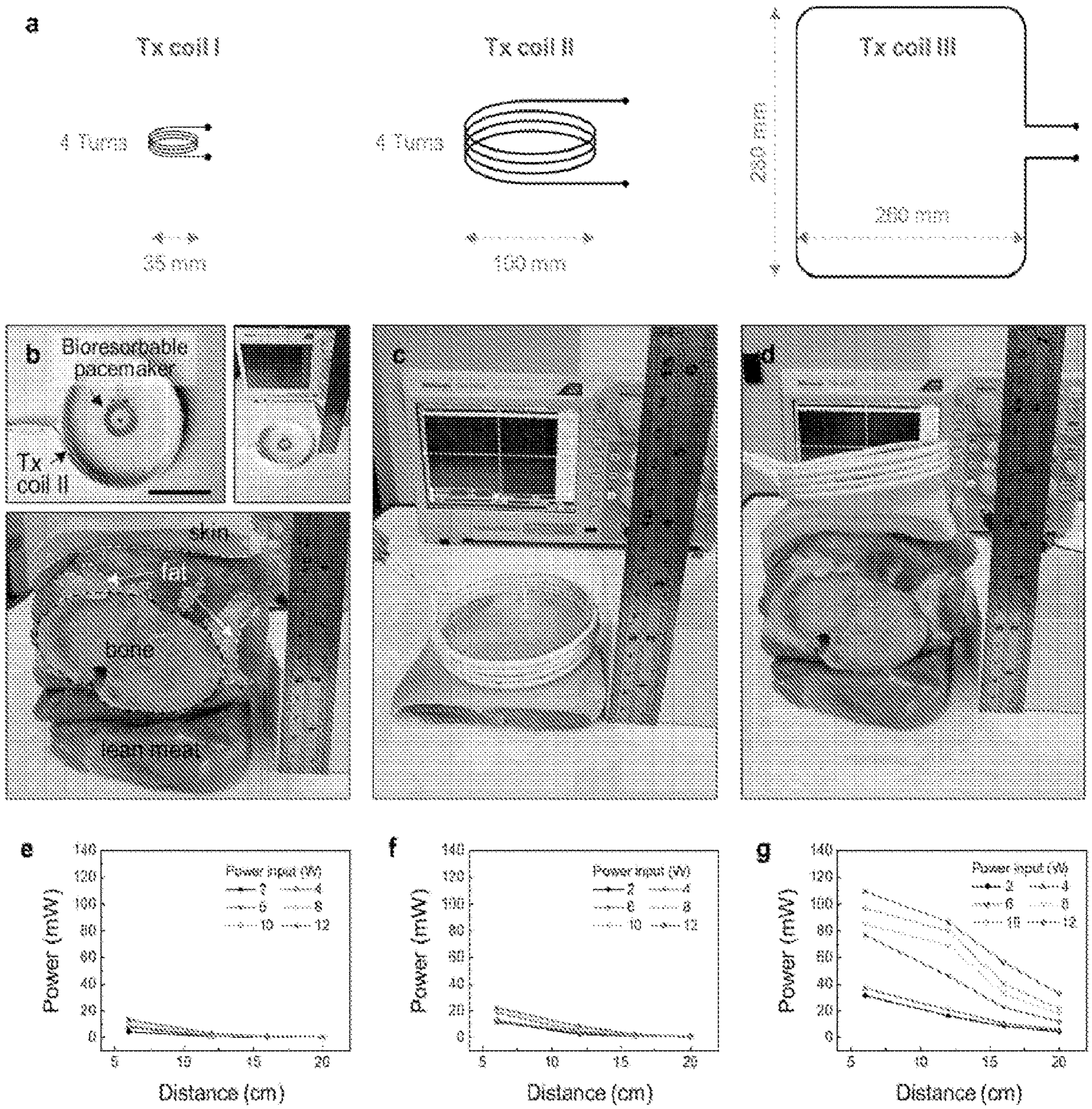
FIG. 19 shows in vitro long-range wireless operation test of a bioresorbable cardiac pacemaker system, according to embodiments of the invention. Panel a: Schematic illustrations of three different designs of Tx coil: (i) Tx coil I (solenoid type; 4 turns; 35 mm diameter); (ii) Tx coil II (solenoid type; 4 turns; 100 mm diameter); Tx coil III (square; 1 turn; 260×280 $mm^2$). Panel b: (top left) Photograph of bioresorbable pacemaker (diameter of Rx coil=25 mm) and Tx coil II. Scale bar, 50 mm. (top right) Experimental setup for measurement of long-range operation. Fixing the position of the bioresorbable pacemaker and changing the position of the Tx coil represents the method used to change the coil-to-coil distance. (bottom) Cross-sectional image of a slice of porcine tissue (~120 mm thick) that includes skin, fat, bone, and muscle. Panel c: Wireless energy transfer through slices of porcine tissue with thicknesses of 20 mm. The oscilloscope indicates an open circuit voltage of 16.8 V (Input power=2 W; input frequency=13.56 MHz). Panel d: Wireless energy transfer through slices of porcine tissue with thicknesses of 120 mm. The oscilloscope indicates an open circuit voltage of 16.8 V (Input power=12 W; input frequency=13.56 MHz). Panels e-g: Changes in output power of the bioresorbable pacemaker as a function of coil-to-coil distance (input frequency=13.56 MHz; Input power=2-12 W; load resistance=5000 (2): (panel e) Tx coil I; (panel f) Tx coil II; (panel g) Tx coil III.
Figure 20:
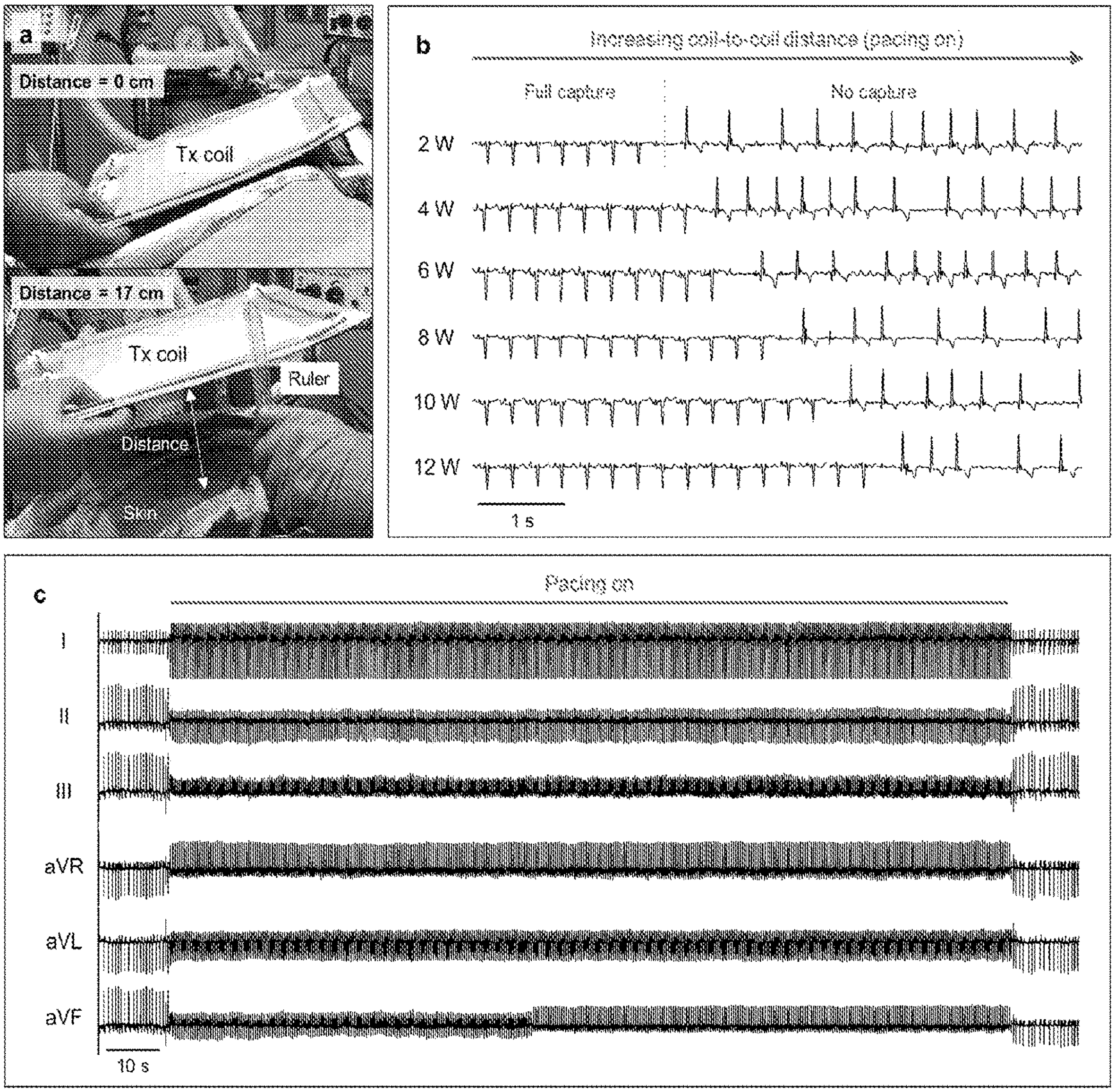
FIG. 20 shows in vivo demonstration of a long-range wireless operation capabilities of bioresorbable cardiac pacemaker system in an in vivo canine model, according to embodiments of the invention. Panel a: Photograph of long-range operation test setup with coil-to-coil distance of (top) 0 cm and (bottom) 17 cm. Measuring the maximum distance for pacing between the surface of skin and the Tx coil (Tx coil III; square; 1 turn; 260×280 $mm^2$) defines the long-range wireless energy transfer capability of this system. Panel b: Changes in ECG with increasing coil-to-coil distance and input power (2-12W; burst period=300 ms; pulse width=5 ms). Transition of ECG signal from ventricular capture (yellow background; ~200 bpm) to intrinsic rhythm (atrial fibrillation; white background; ~120 bpm) defines the maximum distance for pacing. n=3 biologically independent animals per group. Panel c: 6-lead ECG recording of continuous pacing (pacing time=~2 min.; input power=4 W; skin-to-Tx coil distance=10 cm) in the operation room. n=3 biologically independent animals per group.

The coil-to-coil distance is a critical factor that affects the power transfer efficiency in a wireless induction scheme. For example, for a fixed input voltage (i.e., transmitting voltage) of 10 $V_{pp}$ at the Tx coil, the output voltage at the Rx coil decreases from 16 V to 0.2 V with respect to distances from 1 mm to 8 mm (panel g of FIG. 11). Panels a-b of FIG. 18 show simulated scattering parameters (S11) and Q factors of the wireless power harvesting units with four different sizes of Rx coils: 25 (blue), 18 (red), 12 (black), and 8 mm (green). Panel c of FIG. 18 shows that the largest coil (25 mm) generates much higher output voltage (~14.8 V) than the smallest (8 mm) coils (~2.12 V) at the same input voltage of 10 $V_{pp}$ and load resistance of 5 kΩ, as expected with scaling with the area defined by the coil. The results in panel d of FIG. 18 show that increasing the size of the Rx coil proportionally increases energy transfer efficiency. The design of the Tx coil is also important for enhancing wireless power transfer. FIG. 19 shows the results of in vitro tests of the energy transfer capabilities of the bioresorbable pacemaker system with various Tx coils (panel a of FIG. 19): (i) Tx coil I (solenoid type; 3 turns; 12 mm diameter); (ii) Tx coil II (solenoid type; 4 turns; 100 mm diameter); Tx coil III (square; 1 turn; 260×280 $mm^2$). Slices of pig tissue with thicknesses between 20 and 120 mm, including skin, fat, bone, and muscle, served as a mock compound inserted between the Tx coil and the device (panels b-d of FIG. 19). As shown in panel e of FIG. 19, Tx coil I can deliver a power of 13.5 mW (input power=12 W; resonance frequency=13.56 MHz; load resistance=5 kΩ) at a distance of up to 6 cm. In contrast, Tx coil III can deliver a much higher power (32.8 mW) at much large distances (up to 20 cm) in otherwise similar testing conditions (panel g of FIG. 19). These results indicate that this system can support long-range operation in cardiac pacing. In vivo acute pacing tests in a canine model shows results that are consistent with in vitro tests (FIG. 20). As shown in panels a-b of FIG. 20, we monitor the changes in the ECG as a function of coil-to-coil distance to define the maximum pacing distance (i.e., the largest distance between the skin and the Tx coil that enables consistent ventricular capture) at various input powers between 2 and 12 W. Panel c of FIG. 20 shows that the maximum distance is around 17 cm at input power of 12 W. Considering that the distance between the implanted Rx coil and the surface of the skin around 3 cm, the maximum distance between Rx and Tx coils can be 20 cm. Taken together, these results show that the Rx to Tx coil distance and design of the Tx coil impact the parameters for optimal power transfer. In consideration of the translation of these results for patients, these parameters can be selected to tailor to clinical case needs for optimal power transfer at the minimum transmitting voltages.

Example 5

Clinical Case Scenario

Although many parameters contribute to stable pacing, including input frequency, input power, pulse width, burst period, and coil-to-coil distance, optimization of the wireless energy transfer system simplifies the operation. The designs of the Rx and Tx coils are optimized for operation at a fixed input frequency of 13.56 MHz. Studies using the canine model provide guidelines for the maximum pacing distance for a given input power. The pulse width and burst period can be predefined or manipulated during pacing using insights from the patient's ECG signals and therapeutic treatment strategy. Since the cardiac pacing follows an all-or-nothing threshold behavior, users can change one parameter, such as input power or coil-to-coil distance, until changes in ECG signal indicate a transition from intrinsic to pacing rhythm.

Example 6

Encapsulation Materials for Long-Term Operation

Figure 24:
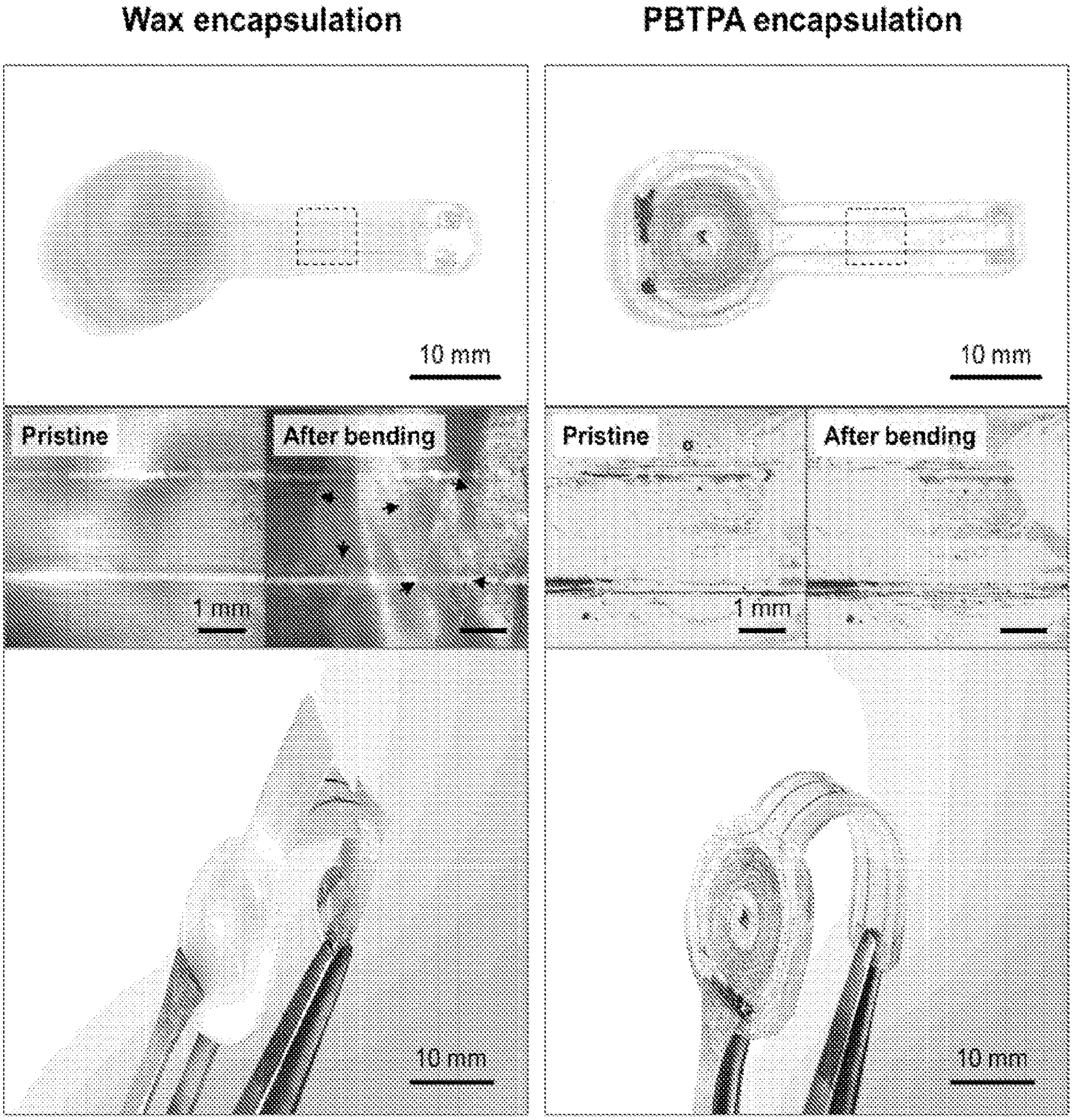
FIG. 24 shows experimental studies of mechanical reliability of polymer-encapsulated bioresorbable, leadless cardiac pacemakers, according to embodiments of the invention. The devices are encapsulated by (left) Candelilla wax and (right) polybuthanedithiol 1,3,5-triallyl- 1,3,5-triazine-2,4,6(1H,3H,5H)-trione pentenoic anhydride (PBTPA). (top) Photographs of encapsulated devices after fabrication. (middle) Optical microscope images of the polymer encapsulated extension electrode (left) before and (right) after bending (bend radius=10 mm). Arrows indicate cracks. (bottom) Photographs of polymer encapsulated devices under mechanical deformation (bend radius=5 mm).
Figure 25:
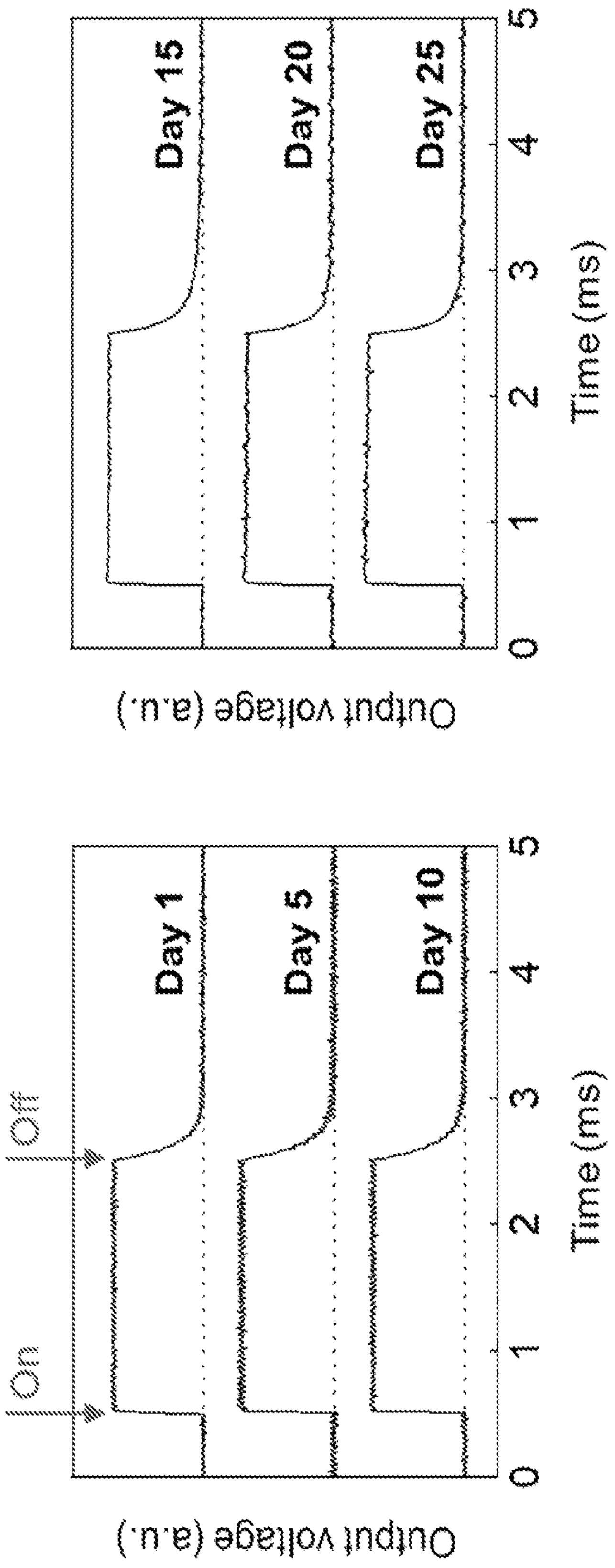
FIG. 25 shows functional lifetime of the bioresorbable cardiac pacemaker with an encapsulating structure formed with a polyanhydride (PBTPA) material, according to embodiments of the invention. During immersion in bovine serum at 37° C. over the course of several weeks, the output voltage of the encapsulated bioresorbable pacemaker during wireless operation remains consistent.

The encapsulation materials and their thickness define the functional lifetime of the devices. Although bioresorbable wax (Candelilla wax) can be considered, its poor mechanical properties and the relatively high melting temperature (~70° C.) needed for dip-coating-based encapsulation process limit its feasibility for use with bioresorbable electrical stimulators. A hydrophobic polyanhydride (polybuthanedithiol 1,3, 5-triallyl-1,3,5-triazine-2,4,6(1H,3H,5H)-trione pentenoic anhydride, PBTPA) can serve as an attractive alternative for an advanced encapsulation structure to allow for long functional lifetimes. The encapsulation process involves placing the device on a partially cured layer of PBTPA and subsequently UV-curing after applying a liquid mixture of precursors on the top. The result is a conformal encapsulation structure with a thickness of approximately 300 μm. This UV-based photocuring process does not damage the bioresorbable devices because it occurs at room temperature, well below the glass transition temperature of the PLGA. FIG. 24 shows the mechanical reliability of bioresorbable cardiac pacemaker with wax or PBTPA encapsulations before and after mechanical bending. Many cracks occur on the wax-encapsulated extension electrode after bending (bend radius=10 mm) due to the mechanical rigidity of the Candelilla wax, and wax encapsulation is delaminated by bending (bend radius=5 mm). In contrast, PBTPA encapsulations maintain their structure before and after mechanical deformation. FIG. 25 shows results of benchtop tests of the water-barrier properties of this encapsulating structure, as demonstrated by the functional lifetime of the wireless, bioresorbable cardiac pacemaker. Soak testing in bovine serum at 37° C. for 25 days reveals stable operation throughout due to the water barrier properties of the hydrophobic chains of the PBTPA. The barrier characteristics can be further enhanced by increasing the thickness of the PBTPA.

In sum, the disclosure presents, among other things, a fully bioresorbable, implantable, leadless cardiac pacemaker that operates in a battery-free fashion and is externally controlled and programmable. The device relies exclusively on materials that resorb when exposed to biofluids in a time-controlled manner via metabolic action and hydrolysis. The materials and design choices create a thin, flexible, and lightweight form that maintain excellent biocompatibility and stable function throughout a desired period of use. Over a subsequent timeframe following the completion of therapy, the devices disappear completely through natural biological processes. Wireless energy transfer via resonant inductive coupling delivers power to the system in a manner that eliminates the need for batteries and allows for externalized control without transcutaneous leads. These characteristics and a miniaturized geometry facilitate full implantation into the body to eliminate the need for percutaneous hardware, which thereby minimizes the risk of device-associated infections and dislodgement.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

LIST OF REFERENCES

[1]. Waldo, A. L., Wells, J. L. J., Cooper, T. B. & MacLean, W. A. Temporary cardiac pacing: applications and techniques in the treatment of cardiac arrhythmias. *Prog. Cardiovasc. Dis.* 23, 451-474 (1981).

[2]. Zoll, P. M. et al. External noninvasive temporary cardiac pacing: Clinical trials. *Circulation* 71, 937-944 (1985).

[3]. Curtis, J. J. et al. A critical look at temporary ventricular pacing following cardiac surgery. *Surgery* 82, 888-893 (1977).

[4]. Wilhelm, M. J. et al. Cardiac pacemaker infection: Surgical management with and without extracorporeal circulation. *Ann. Thorac. Surg.* 64, 1707-1712 (1997).

[5]. Choo, M. H. et al. Permanent pacemaker infections: Characterization and management. *Am. J. Cardiol.* 48, 559-564 (1981).

[6]. Imparato, A. M. & Kim, G. E. Electrode Complications in Patients With Permanent Cardiac Pacemakers. *Arch. Surg.* 105, 705 (1972).

[7]. Bernstein, V., Rotem, C. E. & Peretz, D. I. Permanent pacemakers: 8-year follow-up study. Incidence and management of congestive cardiac failure and perforations. *Ann. Intern. Med.* 74, 361-369 (1971).

[8]. Hartstein, A. I., Jackson, J. & Gilbert, D. N. Prophylactic antibiotics and the insertion of permanent transvenous cardiac pacemakers. *J. Thorac. Cardiovasc. Surg.* 75, 219-223 (1978).

[9]. Austin, J. L., Preis, L. K., Crampton, R. S., Beller, G. A. & Martin, R. P. Analysis of pacemaker malfunction and complications of temporary pacing in the coronary care unit. *Am. J. Cardiol.* 49, 301-306 (1982).

[10]. Lumia, F. J. & Rios, J. C. Temporary transvenous pacemaker therapy: an analysis of complications. *Chest* 64, 604-608 (1973).

[11]. Donovan, K. D. & Lee, K. Y. Indications for and complications of temporary transvenous cardiac pacing. *Anaesth. Intensive Care* 13, 63-70 (1985).

[12]. Braun, M. U. et al. Percutaneous lead implantation connected to an external device in stimulation-dependent patients with systemic infection—A prospective and controlled study. *PACE—Pacing Clin. Electrophysiol.* 29, 875-879 (2006).

[13]. Del Nido, P. & Goldman, B. S. Temporary epicardial pacing after open heart surgery: complications and prevention. *J. Card. Surg.* 4, 99-103 (1989).

[14]. Elmistekawy, E. Safety of temporary pacemaker wires. *Asian Cardiovasc. Thorac. Ann.* 27, 341-346 (2019).

[15]. Gutruf, P. et al. Wireless, battery-free, fully implantable multimodal and multisite pacemakers for applications in small animal models. *Nat. Commun.* 10, 5742 (2019).

[16]. Koo, J. et al. Wireless bioresorbable electronic system enables sustained nonpharmacological neuroregenerative therapy. *Nat. Med.* 24, 1830-1836 (2018).

[17]. Won, S. M. et al. Natural Wax for Transient Electronics. *Adv. Funct. Mater.* 28, 1801819 (2018).

[18]. Choi, Y. S., Koo, J. & Rogers, J. A. Inorganic materials for transient electronics in biomedical applications. *MRS Bull.* 45, 103-112 (2020).

[19]. Makadia, H. K. & Siegel, S. J. Poly Lactic-co-Glycolic Acid (PLGA) as Biodegradable Controlled Drug Delivery Carrier. *Polymers* (*Basel*). 3, 1377-1397 (2011).

[20]. Hwang, S. W. et al. Dissolution chemistry and biocompatibility of single-crystalline silicon nanomembranes and associated materials for transient electronics. *ACS Nano* 8, 5843-5851 (2014).

[21]. Yin, L. et al. Mechanisms for Hydrolysis of Silicon Nanomembranes as Used in Bioresorbable Electronics. *Adv. Mater.* 27, 1857-1864 (2015).

[22]. Yin, L. et al. Dissolvable metals for transient electronics. *Adv. Funct. Mater.* 24, 645-658 (2014).

[23]. Length, F. Chemical and structural characterization of Candelilla (*Euphorbia antisyphilitica* Zucc.). *J. Med. Plants Res.* 7, 702-705 (2013).

[24]. Winter, K. F., Hartmann, R. & Klinke, R. A stimulator with wireless power and signal transmission for implantation in animal experiments and other applications. *J. Neurosci. Methods* 79, 79-85 (1998).

[25]. Dinis, H., Colmiais, I. & Mendes, P. M. Extending the limits of wireless power transfer to miniaturized implantable electronic devices. *Micromachines* 8, 359 (2017).

[26]. Kang, S. K. et al. Bioresorbable silicon electronic sensors for the brain. *Nature* 530, 71-76 (2016).

[27]. Shreiner, D. P., Weisfeldt, M. L. & Shock, N. W. Effects of age, sex, and breeding status on the rat heart. *Am. J. Physiol. Content* 217, 176-180 (1969).

[28]. Mačianskienė, R. et al. Evaluation of Excitation Propagation in the Rabbit Heart: Optical Mapping and Transmural Microelectrode Recordings. *PLoS One* 10, e0123050 (2015).

[29]. T., L. P. et al. Left Ventricular Wall Thickness and the Presence of Asymmetric Hypertrophy in Healthy Young Army Recruits. *Circ. Cardiovasc. Imaging* 6, 262-267 (2013).

[30]. Schwartzman, D., Chang, I., Michele, J. J., Mirotznik, M. S. & Foster, K. R. Electrical Impedance Properties of Normal and Chronically Infarcted Left Ventricular Myocardium. *J. Interv. Card. Electrophysiol.* 3, 213-224 (1999).

[31]. Salazar, Y., Bragos, R., Casas, O., Cinca, J. & Rosell, J. Transmural versus nontransmural in situ electrical impedance spectrum for healthy, ischemic, and healed myocardium. *IEEE Trans. Biomed. Eng.* 51, 1421-1427 (2004).

[32]. Clauss, S. et al. Animal models of arrhythmia: classic electrophysiology to genetically modified large animals. *Nat. Rev. Cardiol.* 16, 457-475 (2019).

[33]. Pichorim, S. F. Design of circular solenoid coils for maximum mutual inductance. in *Proceedings of the* 14*th International Symposium on Biotelemetry* 71-77 (1998).

[34]. Kurs, A. et al. Wireless Power Transfer via Strongly Coupled Magnetic Resonances. *Science* 317, 83 LP-86 (2007).

[35]. Rahko, P. S. Evaluation of the Skin-To-Heart Distance in the Standing Adult by Two-Dimensional Echocardiography. *J. Am. Soc. Echocardiogr.* 21, 761-764 (2008).

[36]. IEEE Standard for Safety Levels with Respect to Human Exposure to Radio Frequency Electromagnetic Fields, 3 kHz to 300 GHz. *IEEE Std C*95.1-2005 (*Revision of IEEE Std C*95.1-1991) 1-238 (2006) doi:10.1109/IEEESTD.2006.99501.

[37]. Choi, Y. S. et al. Biodegradable Polyanhydrides as Encapsulation Layers for Transient Electronics. *Adv. Funct. Mater.* 30, 2000941 (2020).

[38]. Choi, Y. S. et al. Stretchable, dynamic covalent polymers for soft, long-lived bioresorbable electronic stimulators designed to facilitate neuromuscular regeneration. *Nat. Commun.* 11, 5990 (2020).

[39]. Koo, J. et al. Wirelessly controlled, bioresorbable drug delivery devices with active valves that exploit electrochemically triggered crevice corrosion. *Sci. Adv.* 6, eabb 1093 (2020).

[40]. Katsura, M., Sato, J., Akahane, M., Kunimatsu, A. & Abe, O. Current and Novel Techniques for Metal Artifact Reduction at CT: Practical Guide for Radiologists. *RadioGraphics* 38, 450-461 (2018).

[41]. Lee, Y. K. et al. Dissolution of Monocrystalline Silicon Nanomembranes and Their Use as Encapsulation Layers and Electrical Interfaces in Water-Soluble Electronics. *ACS Nano* 11, 12562-12572 (2017).

[42]. Sofia, S. J., Premnath, V. & Merrill, E. W. Poly (ethylene oxide) Grafted to Silicon Surfaces: Grafting Density and Protein Adsorption. *Macromolecules* 31, 5059-5070 (1998).

[43]. Nakanishi, K., Sakiyama, T. & Imamura, K. On the adsorption of proteins on solid surfaces, a common but very complicated phenomenon. *J. Biosci. Bioeng.* 91, 233-244 (2001).

[44]. Lee, G., Choi, Y. S., Yoon, H.-J. & Rogers, J. A. Advances in Physicochemically Stimuli-Responsive Materials for On-Demand Transient Electronic Systems. *Matter* 3, 1031-1052 (2020).

[45]. Sperelakis, N. & Hoshiko, T. Electrical impedance of cardiac muscle. *Circ. Res.* 9, 1280-1283 (1961).

[46]. Fry, C. H. et al. Cytoplasm resistivity of mammalian atrial myocardium determined by dielectrophoresis and impedance methods. *Biophys. J.* 103, 2287-2294 (2012).

[47]. Gabriel, S., Lau, R. W. & Gabriel, C. The dielectric properties of biological tissues: II. Measurements in the frequency range 10 Hz to 20 GHz. *Phys. Med. Biol.* 41, 2251-2269 (1996).

[48]. Rong, C. et al. Analysis of wireless power transfer based on metamaterial using equivalent circuit. *J. Eng.* 2019, 2032-2035 (2019).

[49]. AU—George, S. A., AU—Brennan, J. A. & AU—Efimov, I. R. Preclinical Cardiac Electrophysiology Assessment by Dual Voltage and Calcium Optical Mapping of Human Organotypic Cardiac Slices. *JoVE* e60781 (2020) doi:doi:10.3791/60781.

[50]. Caverly, R. H. & Hiller, G. The frequency-dependent impedance of p-i-n diodes. *IEEE Trans. Microw. Theory Tech.* 37, 787-790 (1989).

[51]. Youbok Lee. Antenna Circuit Design for RFID Applications. in *microID® 13.56 MHz RFID System Design Guide* 210 (Microchip, 2004).

[52]. Lau, E. W. *Leads and Electrodes for Cardiac Implantable Electronic Devices. Clinical Cardiac Pacing, Defibrillation and Resynchronization Therapy* (Elsevier Inc., 2017). doi:10.1016/b978-0-323-37804-8.00011-0.

[53]. Iravanian, S., Herndon, C., Langberg, J. J. & Fenton, F. H. Theoretical Modeling and Experimental Detection of the Extracellular Phasic Impedance Modulation in Rabbit Hearts. *Front. Physiol.* 10, 883 (2019).

[54]. Fallert, M. A. et al. Myocardial electrical impedance mapping of ischemic sheep hearts and healing aneurysms. *Circulation* 87, 199-207 (1993).

[55]. Schwartzman, D., Chang, I., Michele, J. J., Mirotznik, M. S. & Foster, K. R. Electrical Impedance Properties of Normal and Chronically Infarcted Left Ventricular Myocardium. *J. Interv. Card. Electrophysiol.* 3, 213-224 (1999).

[56]. Rong, C. et al. Analysis of wireless power transfer based on metamaterial using equivalent circuit. *J. Eng.* 2019, 2032-2035 (2019).

[57]. Koo, J. et al. Wireless bioresorbable electronic system enables sustained nonpharmacological neuroregenerative therapy. *Nat. Med.* 24, 1830-1836 (2018).

[58]. Choi, Y. S. et al. Biodegradable Polyanhydrides as Encapsulation Layers for Transient Electronics. *Adv. Funct. Mater.* 30, 2000941 (2020).

What is claimed is:

1. A device implantable on a target of interest of a subject for pacemaker, neuromodulator, and/or defibrillator therapy, comprising:

a wireless power harvesting unit configured to deliver power via resonant inductive coupling to the target of interest for stimulation in a manner that eliminates need for batteries and capacitors and allows for externalized control without transcutaneous leads.

2. The device of claim 1, wherein the wireless power harvesting unit comprises a wireless receiver including one or more inductive coils, a radiofrequency (RF) PIN diode, and a dielectric interlayer that acts as a power harvester and control interface.

3. The device of claim 2, wherein in operation, electrical waveform is generated by an external waveform generator and transferred to the wireless receiver of the device, and the received waveform is transformed into a direct current output via the RF PIN diode to stimulate tissue of the target of interest.

4. The device of claim 2, wherein each of the one or more inductive coils is formed of a metallic conductive material comprising magnesium (Mg), tungsten (W), molybdenum (Mo), iron (Fe), and/or zinc (Zn) in a single-layered structure or a multiple-layered structure, or an alloy thereof.

5. The device of claim 2, wherein the RF PIN diode comprises a doped polycrystalline or monocrystalline semiconductor material, or a two-dimensional semiconductor material, or a combination of them.

6. The device of claim 5, wherein the two-dimensional semiconductor material comprises transition metal dichalcogenides, and/or hexagonal boron nitride.

7. The device of claim 5, wherein the doped polycrystalline or monocrystalline semiconductor material comprises silicon (Si), gallium (Ga), gallium arsenide (GaAs), and/or zinc oxide (ZnO).

8. The device of claim 7, wherein the RF PIN diode comprises a doped monocrystalline silicon nanomembrane (Si NM).

9. The device of claim 2, further comprising interconnections electrically connecting the one or more inductive coils to the RF PIN diode.

10. The device of claim 9, wherein the interconnections are formed of a composite paste comprising conductive particles including W and/or Mo, or a two-dimensional conductive material (MXenes), or a combination of them.

11. The device of claim 9, further comprising a pair of flexible extension electrodes electrically connecting to the one or more inductive coils and the RF PIN diode, respectively.

12. The device of claim 11, wherein each of the pair of flexible extension electrodes is formed of a metallic conductive material comprising magnesium (Mg), tungsten (W), molybdenum (Mo), iron (Fe), and/or zinc (Zn) in a single-layered structure or a multiple-layered structure, or an alloy thereof.

13. The device of claim 11, wherein each of the pair of flexible extension electrodes is provided with a contact pad at its distal end to the one or more inductive coils or the RF PIN diode for interfacing with tissue of the target of interest.

14. The device of claim 13, further comprising an encapsulation structure surrounding the device, excluding the contact pad.

15. The device of claim 14, wherein the encapsulation structure comprises one or more of top and bottom layers formed of PLGA, polyurethane, polyanhydride, and/or PDMS.

16. The device of claim 11, being flexible such that device dimensions are alterable by adjusting a length of the extension electrodes to meet requirements for a target application.

17. The device of claim 16, having a miniaturized geometry that facilitates full implantation into the target of interest of the subject to eliminate the need for percutaneous hardware, thereby minimizing the risk of device-associated infections and dislodgement.

18. The device of claim 16, being capable of effectively capturing and sustaining cardiac rhythms across different species and platforms.

19. The device of claim 16, being eliminable completely from the target of interest of the subject through natural chemical/biochemical processes of hydrolysis and/or metabolic actions, over a subsequent timeframe following completion of therapy.

20. The device of claim 16, being fully bioresorbable, implantable, leadless cardiac pacemaker operating in a battery-free fashion and being externally controllable and programmable.

21. A device implantable on a target of interest of a subject for pacemaker, neuromodulator, and/or defibrillator therapy, comprising:

a wireless power harvesting unit comprising an antenna configured to receive wirelessly transmitted electrical waveform via resonant inductive coupling, and a RF PIN diode electrically coupled to the antenna and configured to perform capacitor-free rectification of the received electrical waveform; and a pair of electrodes configured to deliver electrical stimuli of the rectified electrical waveform to the target of interest, each electrode having a first end electrically connecting to the wireless power harvesting unit and a second end attachable to the target of interest, wherein the device is capacitor free.

22. The device of claim 21, wherein the antenna comprises a loop antenna having at least one coil.

23. The device of claim 22, wherein the loop antenna is in a bilayer, dual-coil configuration having two coils electrically connected to one another in series and a dielectric interlayer positioned between the two coils.

24. The device of claim 23, wherein the dielectric interlayer comprises one or more of poly(lactide-co-glycolide) (PLGA), polyurethane, polyanhydride, and poly(dimethyl siloxane) (PDMS).

25. The device of claim 24, wherein the dielectric interlayer has a thickness in a range of about 1-800 μm.

26. The device of claim 23, wherein each of the two coils is formed of a metallic conductive material comprising magnesium (Mg), tungsten (W), molybdenum (Mo), iron (Fe), and/or zinc (Zn) in a single-layered structure or a multiple-layered structure, or an alloy thereof.

27. The device of claim 26, wherein each of the two coils comprises a two-layered structure of tungsten-coated magnesium (W/Mg).

28. The device of claim 23, wherein the two coils have a width in a range of about 200 nm-500 μm, and a thickness in a range of about 1-800 μm.

29. The device of claim 21, wherein the RF PIN diode comprises a doped polycrystalline or monocrystalline semiconductor material, or a two-dimensional semiconductor material, or a combination of them.

30. The device of claim 29, wherein the two-dimensional semiconductor material comprises transition metal dichalcogenides, and/or hexagonal boron nitride.

31. The device of claim 29, wherein the doped polycrystalline or monocrystalline semiconductor material comprises silicon (Si), gallium (Ga), gallium arsenide (GaAs), and/or zinc oxide (ZnO).

32. The device of claim 31, wherein the RF PIN diode comprises a doped monocrystalline silicon nanomembrane (Si NM) having a thickness in a range of about 20-1000 nm.

33. The device of claim 21, wherein the wireless power harvesting unit further comprises interconnections electrically connecting the RF PIN diode to the antenna and said electrode.

34. The device of claim 33, wherein the interconnections are formed of a composite paste comprising conductive particles including W and/or Mo, or a two-dimensional conductive material (MXenes), or a combination of them.

35. The device of claim 21, wherein the pair of electrodes is spatially apart from each other to define an electrode spacing that is in a range of about 0.5-10 mm.

36. The device of claim 21, wherein the pair of electrodes is flexible, such that the electrode length and/or the distance between the pair of electrodes are adjustable.

37. The device of claim 21, wherein the second end of each electrode includes a contact pad for attaching said electrode to the target of interest.

38. The device of claim 21, wherein the pair of electrodes is formed of a metallic conductive material comprising magnesium (Mg), tungsten (W), molybdenum (Mo), iron (Fe), and/or zinc (Zn) in a single-layered structure or a multiple-layered structure, or an alloy thereof.

39. The device of claim 37, further comprising an encapsulation structure surrounding the device.

40. The device of claim 39, wherein the encapsulation structure comprises one or more of top and bottom layers formed of PLGA, polyurethane, polyanhydride, and/or PDMS.

41. The device of claim 39, wherein the encapsulation structure has a thickness in a range of about 50-500 μm.

42. The device of claim 39, wherein the contact pad is at least partially exposed from the encapsulation structure, so that when sutured, said electrode is in contact with the target of interest.

43. The device of claim 21, being configured to be eliminable completely from the target of interest of the subject through natural chemical/biochemical processes of hydrolysis and/or metabolic actions, over a subsequent timeframe following completion of therapy.

44. The device of claim 21, being compatible with computed tomography (CT) for non-invasive monitoring of the bioresorption process.

45. The device of claim 21, being configured to be a thin, lightweight, flexible, bioresorbable, implantable, leadless cardiac pacemaker and/or defibrillator operating in a battery-free fashion and being externally controllable and programmable.

46. A method of transcutaneous pacing a target of interest of a subject for pacemaker, neuromodulator, and/or defibrillator therapy, comprising:

implanting a device in the target of interest, wherein the device is according to claim 1; and wirelessly transmitting the electrical stimuli to the antenna, wherein the electrical stimuli are delivered by the implanted device to pace the target of interest at frequency, rate, stimulation strength, and/or time period that are adjustable based on the need of the pacemaker, neuromodulator, and/or defibrillator therapy.

47. The method of claim 46, wherein the electrical stimuli are adapted such that the implanted device operates at a minimum power that can pace the target of interest in order to minimize voltage-induced electroporation damage to the target of interest and to limit electrochemical degradation of the electrodes.

48. The method of claim 47, wherein said transmitting the electrical stimuli is performed by an external transmitter antenna that is placed at a distance from the antenna of the implanted device.

49. The method of claim 48, wherein the distance between the external transmitter antenna and the receiver antenna of the implanted device is up to about 50 cm.

50. The method of claim 48, wherein the external transmitter antenna and the antenna are optimized for operation at a fixed input frequency in a range of about 10-15 MHz, preferably about 13.56 MHz.

51. The method of claim 46, wherein the device is eliminable completely from the target of interest of the subject through natural chemical/biochemical processes of hydrolysis and/or metabolic actions, over a subsequent timeframe following completion of therapy.

52. The method of claim 46, wherein the device is fully bioresorbable, implantable, leadless cardiac pacemaker operating in a battery-free fashion and being externally controllable and programmable.

53. A method of making a leadless and battery-free cardiac pacemaker and/or defibrillator, comprising forming a wireless receiver;

forming a radiofrequency (RF) PIN diode electrically coupled to the wireless receiver;

forming a pair of flexible electrodes electrically connecting the wireless receiver and the RF PIN diode, respectively; and assembling the wireless receiver, the RF PIN diode and the flexible electrodes on a bioresorbable encapsulation structure comprising one or more of top and bottom layers formed of poly(lactide-co-glycolide) (PLGA), polyurethane, polyanhydride, and poly(dimethyl siloxane) (PDMS), wherein the leadless and battery-free cardiac pacemaker and/or defibrillator is capacitor free.

54. The method of claim 53, wherein the wireless receiver comprises a loop antenna in a bilayer, dual-coil configuration having two inductive coils electrically connected to one another in series and a dielectric interlayer positioned between the two coils.

55. The method of claim 54, wherein each of the two inductive coils is formed of a metallic conductive material comprising magnesium (Mg), tungsten (W), molybdenum (Mo), iron (Fe), and/or zinc (Zn) in a single-layered structure or a multiple-layered structure, or an alloy thereof.

56. The method of claim 55, wherein the dielectric interlayer comprises one or more of poly(lactide-co-glycolide) (PLGA), polyurethane, polyanhydride, and poly (dimethyl siloxane) (PDMS).

57. The method of claim 56, wherein said forming the wireless receiver comprises:

defining magnesium (Mg) coil structures on a temporary substrate;

depositing tungsten (W) on the Mg coil structures to form double-layered W/Mg coils; and transferring the double-layered W/Mg coils onto the dielectric interlayer to serve as the loop antenna for power harvesting.

58. The method of claim 57, wherein said defining the Mg coil structures is performed by laser-cutting, and said depositing W on the Mg coil structures is performed by sputter coating.

59. The method of claim 53, wherein the RF PIN diode is formed of a doped polycrystalline or monocrystalline semiconductor material, or a two-dimensional semiconductor material, or a combination of them.

60. The method of claim 59, wherein the two-dimensional semiconductor material comprises transition metal dichalcogenides, and/or hexagonal boron nitride.

61. The method of claim 59, wherein the doped polycrystalline or monocrystalline semiconductor material comprises silicon (Si), gallium (Ga), gallium arsenide (GaAs), and/or zinc oxide (ZnO).

62. The method of claim 61, wherein said forming the RF PIN diode comprises solid-state diffusion of boron and phosphorus through a photolithographically defined mask of $SiO_2$ to yield the PIN RF diode with monocrystalline Si nanomembranes (Si NMs) derived from a Si-on-insulator wafer.

63. The method of claim 57, wherein said forming the RF PIN diode further comprises:

removing buried oxide by immersion in hydrofluoric acid to release and transfer printing of the Si NMs onto a sacrificial layer of diluted poly(pyromellitic dianhydride co-4,4'-oxydianiline) (DPI) on a film of poly (methyl methacrylate) on the silicon wafer;

photolithographic patterning and reactive ion etching to determine the lateral dimensions of the doped Si NMs for integration into the PIN diode;

lift-off procedures applied with Mg deposited by electron beam evaporation to define electrical contacts; and spin casting an overcoat of DPI and dry etching through the underlying DPI and poly(methyl methacrylate) to define an open mesh layout, followed by immersion in acetone, to release the PIN diode for its transfer on the PLGA substrate.

64. The method of claim 63, further comprising oxygen reactive ion etching to remove the DPI layer during/after the transfer printing.

65. The method of claim 53, wherein said forming electrodes comprises laser-cutting a piece of Mg foil into the electrodes.

* * * * *